(12) United States Patent
Ding et al.

(10) Patent No.: US 10,183,099 B2
(45) Date of Patent: Jan. 22, 2019

(54) ANTIMICROBIAL AND ANTIFOULING CATECHOL-CONTAINING POLYCARBONATES FOR MEDICAL APPLICATIONS

(71) Applicants: International Business Machines Corporation, Armonk, NY (US); Agency For Science, Technology and Research, Singapore (SG)

(72) Inventors: Xin Ding, Singapore (SG); James L. Hedrick, Pleasanton, CA (US); Chuan Yang, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 199 days.

(21) Appl. No.: 14/047,056

(22) Filed: Oct. 7, 2013

(65) Prior Publication Data

US 2015/0098976 A1 Apr. 9, 2015

(51) Int. Cl.
 *A61L 29/08* (2006.01)
 *A61L 29/16* (2006.01)

(52) U.S. Cl.
 CPC ............. *A61L 29/085* (2013.01); *A61L 29/16* (2013.01); *A61L 2300/404* (2013.01)

(58) Field of Classification Search
 None
 See application file for complete search history.

(56) References Cited

U.S. PATENT DOCUMENTS

| | | |
|---|---|---|
| 3,223,678 A | 12/1965 | Bolgiano |
| 4,443,593 A | 4/1984 | Collins |
| 8,420,069 B2 | 4/2013 | Stofko, Jr. et al. |
| 2005/0100687 A1 | 5/2005 | Dutton et al. |
| 2008/0149566 A1 | 6/2008 | Messersmith et al. |
| 2010/0330025 A1 | 12/2010 | Messersmith et al. |
| 2011/0305872 A1 | 12/2011 | Li et al. |
| 2013/0017332 A1 | 1/2013 | Messersmith et al. |

FOREIGN PATENT DOCUMENTS

CN 102702539 A * 10/2012 ............. C08B 37/08

OTHER PUBLICATIONS

Updated Machine translation, CN102702539, Oct. 3, 2012.*
Pratt et al. Chem. Comm., 2008, 114-116.*
Blencowe, et al., "Core cross-linked star polymers via controlled radical polymerisation," Polymer 50 (2009) 5-32; Available online Oct. 4, 2008.
Curtis, et al., "A Comparative Assessment of Three Common Catheter Materials," Dow Corning publication, retrieved from the web May 17, 2013 at http://www1.dowcorning.com/content/publishedlit/52/1116.pdf
Ding, et al., "Antibacterial and antifouling catheter coatings using surface grafted PEG-b-cationic polycarbonate diblock copolymers," Biomaterials 33 (2012) 6593-6603; Available online Jun. 27, 2012.
Dreyer, et al., "Elucidating the Structure of Poly(dopamine)," Langmuir 2012, 28, 6428-6435; Published: Apr. 4, 2012.
Han, et al., "Immobilization of Amphiphilic Polycations by Catechol Functionality for Antimicrobial Coatings," Langmuir, Apr. 5, 2011; 27(7): 4010-4019.
Hong, et al., "Non-Covalent Self-Assembly and Covalent Polymerization Co-Contribute to Polydopamine Formation," Adv. Funct. Mater. 2012, 22, 4711-4717.
Khan, et al., "Biomimetic Design of Amphiphilic Polycations and Surface Grafting onto Polycarbonate Urethane Film as Effective Antibacterial Agents with Controlled Hemocompatibility," Journal of Polymer Science, Part A: Polymer Chemistry 2013, 51, 3166-3176; published online Apr. 22, 2013.
Ku, et al., "General functionalization route for cell adhesion on non-wetting surfaces," Biomaterials 31 (2010) 2535-2541; Available online Jan. 12, 2010.
Lee, et al., "Mussel-Inspired Surface Chemistry for Multifunctional Coatings," Science 318, 426 (2007); published Oct. 19, 2007.
Liu, et al., "Antimicrobial and Antifouling Hydrogels Formed In Situ from Polycarbonate and Poly(ethylene glycol) via Michael Addition," Adv. Mater. 2012, 24, 6484-6489; Published online: Sep. 27, 2012.
Pratt, et al., "Exploration, Optimization, and Application of Supramolecular Thiourea-Amine Catalysts for the Synthesis of Lactide (Co)polymers," Macromolecules 2006, 39, 7863-7871.
Pratt, et al., "Tagging alcohols with cyclic carbonate: a versatile equivalent of (meth)acrylate for ring-opening polymerization", Chem. Commun., (2008), 114-116, Royal Society of Chemistry, UK, first published Oct. 25, 2007 on web.
Shalev, et al., "Non-leaching antimicrobial surfaces through polydopamine bio-inspired coating of quaternary ammonium salts or an ultrashort antimicrobial lipopeptide," J. Mater. Chem., 2012, 22, 2026-2032.
Sileika, et al., "Antibacterial Performance of Polydopamine-Modified Polymer Surfaces Containing Passive and Active Components," ACS Appl. Mater. Interfaces 2011, 3, 4602-4610; Published: Nov. 1, 2011.
Yang, et al., "Stainless steel surfaces with thiol-terminated hyperbranched polymers for functionalization via thiol-based chemistry," Polym. Chem., 2013, 4, 3105-3115.
Gandhi, et al., "The Structure of Glycosaminoglycans and their Interactions with Proteins", Chem Biol Drug Des 2008; 72: 455-482.

* cited by examiner

*Primary Examiner* — Mina Haghighatian
*Assistant Examiner* — Erin E Hirt
(74) *Attorney, Agent, or Firm* — Michael R. Roberts

(57) ABSTRACT

Catechol-bearing polycarbonates (catechol polymers) were prepared comprising i) a catechol repeat unit comprising a side chain catechol group, ii) a cationic repeat unit comprising a side chain cationic group selected from the group consisting of quaternary amine groups, quaternary phosphine groups, and combinations thereof, and iii) a PEG repeat unit comprising a side chain poly(ethylene oxide) group having a degree of polymerization of about 5 to about 30. The catechol polymers form antimicrobial and antifouling films on a variety of substrate surfaces, in particular silicone rubber.

34 Claims, 16 Drawing Sheets

ANTIMICROBIAL AND ANTIFOULING CATECHOL-CONTAINING POLYCARBONATES FOR MEDICAL APPLICATIONS

PARTIES TO A JOINT RESEARCH AGREEMENT

This invention was made under a joint research agreement between International Business Machines Corporation and the Agency For Science, Technology and Research.

BACKGROUND

The present invention relates to antimicrobial and antifouling catechol-containing polycarbonates for medical applications, and more specifically, to silicone catheter materials having antimicrobial and antifouling surface layers.

Nosocomial infections are one of the leading causes of death in the USA. Infections caused by medical devices, especially intravascular and urinary catheters, are major challenges in hospitals. Various catheter coating methods have been studied to prevent catheter-associated infections. However, it is difficult to obtain an effective and facile coating without elevating the toxicity of the catheter surfaces. For example, the coating of silver nanoparticles on catheters was reported to inhibit the adhesion of *Staphylococcus aureus* (*S. aureus*), while accelerating coagulation of contacted blood. As another example, hydrophobic drugs were applied to catheter surfaces using layer-by-layer techniques to generate antibacterial and antifouling catheter surfaces. Coatings of hydrophilic polyacrylamide and cationic 3-(trimethoxysilyl)-propyldimethyloctadecylammonium chloride on silicone rubber were also reported to prevent bacterial fouling. However, these techniques usually require multiple steps (e.g., surface hydrophilization, aminosilanization, chemical grafting, and/or polymerization) that increase production cost.

Poly(ethylene glycol) (PEG) has been of great interest in the development of antifouling coatings due to its hydrophilicity and nontoxicity. However, antifouling performance of PEG coatings decrease over time because PEG does not kill bacteria.

Recently, a two-step antibacterial and antifouling coating on a catheter surface was prepared by 1) forming a reactive polydopamine layer on the catheter surface and 2) reacting a diblock copolymer containing a thiol-functionalized PEG and cationic amphiphilic polycarbonate with the polydopamine layer via the thiol group on the distal end of the PEG chain. This coating successfully eradicated *Staphylococcus aureus* (*S. aureus*) in solution, prevented bacterial fouling on the catheter surface, and exhibited blood compatibility. However, this coating failed to kill and prevent fouling of Gram-negative bacteria such as *Escherichia coli* (*E. coli*), which often cause intravascular and urinary catheters-associated infections.

Therefore, a pressing need exists to develop more effective antimicrobial and antifouling coatings on silicone rubber materials for the prevention of CAIs.

SUMMARY

Accordingly, a polycarbonate is disclosed, comprising:
a catechol repeat unit comprising i) an aliphatic carbonate backbone portion and ii) a side chain linked to the backbone portion, the side chain comprising a catechol group of formula (A-1):

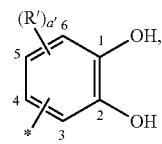

wherein
a' is an integer of 0 to 3, and
each R' is an independent monovalent radical selected from the group consisting of halogens, methyl, and ethyl.

Also disclosed is a polycarbonate, comprising:
a catechol repeat unit comprising i) an aliphatic carbonate backbone portion and ii) a side chain linked to the backbone portion, the side chain comprising a catechol group of formula (A-1):

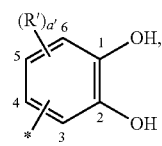

wherein a' is an integer of 0 to 3, and each R' is an independent monovalent radical selected from the group consisting of halogens, methyl, and ethyl;
a cationic repeat unit comprising i) an aliphatic carbonate backbone portion and ii) a side chain linked to the carbonate backbone, the side chain comprising a cationic group selected from the group consisting of quaternary amine groups, quaternary phosphine groups, and combinations thereof; and
a PEG repeat unit comprising i) an aliphatic carbonate backbone portion and ii) a side chain linked to the carbonate backbone portion, the side chain comprising a poly(ethylene oxide) chain (PEG chain) having a degree of polymerization of about 5 to about 30;
wherein
the catechol repeat unit, the cationic repeat unit, and the PEG repeat unit are bound in a polycarbonate chain.

Further disclosed is a method of forming a catechol polymer, comprising:
forming by an organocatalyzed ring opening polymerization of one or more cyclic carbonate monomers a first polycarbonate comprising an electrophilic repeat unit, wherein the electrophilic repeat unit comprises i) a carbonate backbone portion and ii) a side chain linked to the carbonate backbone portion, the side chain comprising a leaving group capable of displacement by a nucleophilic group; and
treating a mixture of the first polycarbonate in a solvent with a catechol compound comprising the nucleophilic group, thereby forming the catechol polymer.

Another method is disclosed, comprising:
forming by an organocatalyzed ring opening polymerization of one or more cyclic carbonate monomers a first polycarbonate comprising an electrophilic repeat unit, wherein the electrophilic repeat unit comprises i) a carbonate backbone portion and ii) a side chain portion linked to the carbonate backbone portion, the side chain comprising a leaving group capable of displacement by a nucleophilic group; and treating the first polycarbonate with a mixture comprising i) a solvent, ii) a first compound comprising a first nucleophilic group and a catechol group, and iii) a second compound comprising a second nucleophilic group, the second nucleophilic group capable of forming a quaternary amine group and/or a quaternary phosphine group, thereby forming an antimicrobial cationic polycarbonate;

wherein the antimicrobial cationic polycarbonate comprises i) a first carbonate repeat unit (catechol repeat unit) comprising a first carbonate backbone portion and a first side chain portion linked to the first carbonate backbone portion, the first side chain portion comprising a catechol group and ii) a second carbonate repeat unit (cationic repeat unit) comprising a second carbonate backbone portion and a second side chain portion linked to the second carbonate backbone portion, the second side chain portion comprising the quaternary amine group and/or the quaternary phosphine group, and the catechol repeat unit and the cationic repeat unit are derived from the electrophilic repeat unit.

Another method is disclosed, comprising:

disposing on a surface of a substrate a mixture comprising a solvent and a catechol polymer, thereby forming an initial film layer, wherein the catechol polymer comprises i) a first carbonate repeat unit (catechol repeat unit) comprising an aliphatic carbonate backbone portion and a side chain catechol group, ii) a second carbonate repeat unit (cationic repeat unit) comprising an aliphatic carbonate backbone portion and a side chain cationic group selected from the group consisting quaternary amines, quaternary phosphines, and combinations thereof, and iii) a third carbonate repeat unit (PEG repeat unit) comprising an aliphatic carbonate backbone portion and a side chain poly(ethylene oxide) group; and removing the solvent from the initial film layer, thereby forming a treated substrate comprising a catechol layer, the catechol layer comprising the catechol polymer disposed on the surface of the substrate;

wherein the catechol layer is antimicrobial and/or antifouling with respect to at least one Gram-negative and/or Gram-Positive microbe.

Also disclosed is an antimicrobial and/or antifouling silicone rubber, comprising:

a catechol layer disposed on a surface of a silicone rubber substrate, the catechol layer comprising an above-described polycarbonate.

The above-described and other features and advantages of the present invention will be appreciated and understood by those skilled in the art from the following detailed description, drawings, and appended claims.

DETAILED DESCRIPTION

Figure 1:
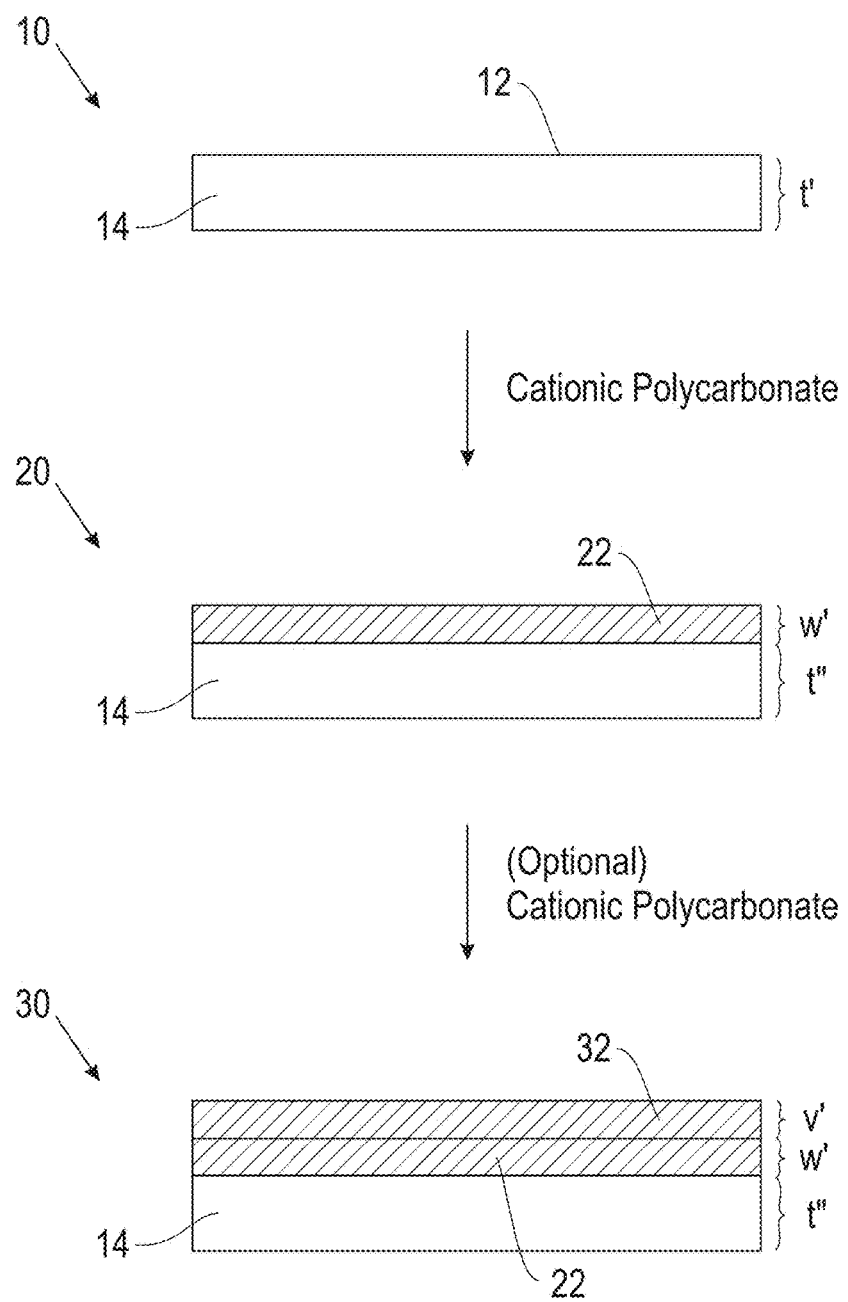
FIG. 1 is a series of cross-sectional layer diagrams illustrating a process of forming an antimicrobial silicone rubber.

Disclosed are catechol-bearing polycarbonates, referred to herein simply as "catechol polymers", for forming polycarbonate surface layers ("catechol layers") disposed on a variety of substrate surfaces, in particular the surfaces of silicone rubber substrates. The catechol polymers can be used singularly or in combination to form a given catechol layer. The catechol groups of catechol layer can be in the form of a catechol, an oxidized derivative of the catechol (i.e., quinone), a polymerized byproduct of any of the foregoing, or combinations thereof. Typically, the catechol layer is colored (e.g., brown), adheres strongly to the substrate surface, and is insoluble in water and organic solvents, indicating the presence of oxidized and/or polymerized catechol groups in the dried catechol layer.

In an embodiment, the catechol polymer comprises a cationic side chain group, and the catechol layer is antimicrobial, capable of killing Gram-positive and/or Gram-negative bacteria. In another embodiment, the catechol polymer comprises a side chain oligomeric poly(ethylene oxide) group, and the catechol layer is anti-fouling, capable of preventing bacterial fouling of the treated surface. In another embodiment, the catechol polymer comprises a side chain cationic group and a side chain oligomeric poly(ethylene oxide) group, and the catechol layer possesses potent antimicrobial and anti-fouling properties. The catechol layers can also exhibit hemolytic compatibility, making them attractive for medical applications (e.g., forming antimicrobial and anti-fouling surface layers on medical devices such as catheters).

Catechol Repeat Units

Herein, a catechol group has a structure according to formula (A-1):

wherein a' is an integer of 0 to 3, and each R' is an independent monovalent radical selected from the group consisting of halogens, methyl, and ethyl. The starred bond of the catechol group is linked to another portion of the first carbonate repeat unit. The starred bond can be attached to position 3, 4, 5, or 6 of the aromatic ring of the catechol group. Each aromatic carbon labeled 3, 4, 5, and 6 that is not bonded to an R' group or a starred bond has a hydrogen substituent.

The catechol polymers comprise a first carbonate repeat unit having a catechol group. These repeat units are referred to as "catechol repeat units". The catechol repeat units have a structure in accordance with formula (A-2):

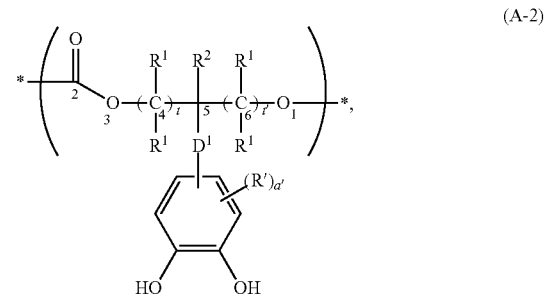

wherein
$D^1$ is a divalent linking group comprising at least 1 carbon,
each $R^1$ is an independent monovalent radical selected from the group consisting of hydrogen, halogens, methyl, and ethyl,
$R^2$ is a monovalent radical selected from the group consisting of hydrogen, halogens, and alkyl groups comprising 1 to 6 carbons,
each R' is an independent monovalent radical selected from the group consisting of halogens, methyl, and ethyl, a' is an integer of 0 to 3, t is a positive integer having a value of 0 to 2, t' is a positive integer having a value of 0 to 2, and t and t' cannot both be zero.

The starred bonds of formula (A-2) represent attachment points to other portions of the polymer backbone. The polymer backbone atoms of the catechol repeat unit are labeled 1 to 6 in formula (A-2) with the catechol-bearing side chain group linked to backbone carbon 5 of the repeat unit. In an embodiment, t and t' are both 1, each $R^1$ is hydrogen, and $R^2$ is methyl or ethyl.

More specific catechol repeat units have a structure in accordance with formula (A-3):

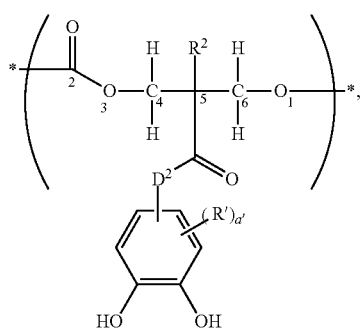

(A-3)

wherein $D^2$ is a divalent linking group comprising at least 1 carbon, each R' is an independent monovalent radical selected from the group consisting of halogens, methyl, and ethyl, a' is an integer of 0 to 3, and $R^2$ is a monovalent radical selected from the group consisting of hydrogen, halogens, and alkyl groups comprising 1 to 6 carbons.

The backbone atoms are numbered in formula (A-3).

Other more specific catechol repeat units have a structure in accordance with formula (A-4):

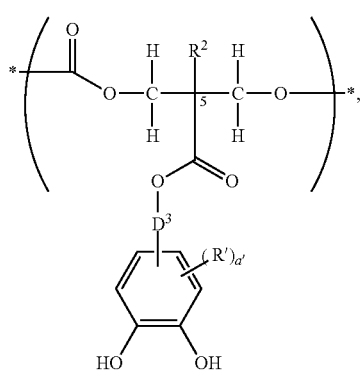

(A-4)

wherein $D^3$ is a divalent linking group comprising at least 1 carbon, each R' is an independent monovalent radical selected from the group consisting of halogens, methyl, and ethyl, a' is an integer of 0 to 3, and $R^2$ is a monovalent radical selected from the group consisting of hydrogen, halogens, and alkyl groups comprising 1 to 6 carbons.

In this instance, the linking group C(=O)O-$D^3$ corresponds to divalent linking group $D^1$ of formula (A-2), and the catechol-bearing side chain is linked to backbone carbon labeled 5.

Other more specific catechol repeat units have a structure in accordance with formula (A-5):

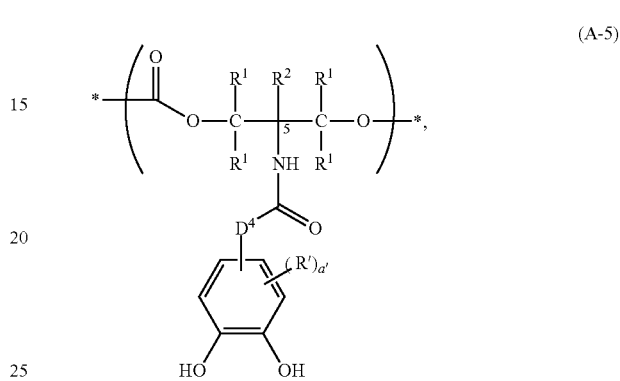

(A-5)

wherein $D^4$ is a divalent linking group comprising at least 1 carbon, each R' is an independent monovalent radical selected from the group consisting of halogens, methyl, and ethyl, each $R^1$ is an independent monovalent radical selected from the group consisting of hydrogen, halogens, methyl, and ethyl, a' is an integer of 0 to 3, and $R^2$ is a monovalent radical selected from the group consisting of hydrogen, halogens, and alkyl groups comprising 1 to 6 carbons.

In this instance, the linking group NHC(=O)$D^4$ corresponds to divalent linking group $D^1$ of formula (A-2), and the catechol-bearing side chain is linked to backbone carbon labeled 5. Serinol and/or threoninol provide useful starting materials for the formation of repeat units of formula (A-5).

Other catechol repeat units have a structure in accordance with formula (A-6):

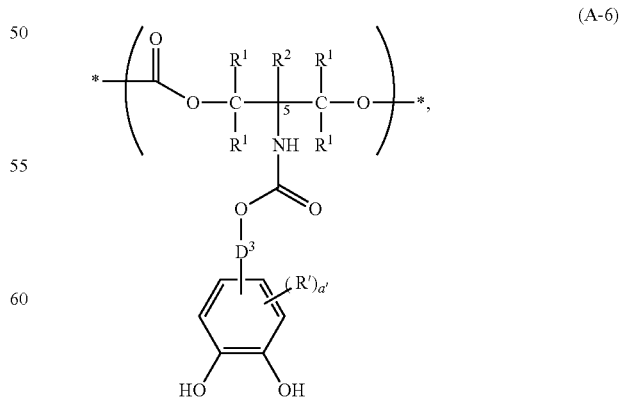

(A-6)

wherein $D^5$ is a divalent linking group comprising at least 1 carbon, each R' is an independent monovalent radical selected from the group consisting of halogens, methyl, and ethyl, each $R^1$ is an independent monovalent radical selected from the group consisting of hydrogen, halogens, methyl, and ethyl, a' is an integer of 0 to 3, and $R^2$ is a monovalent radical selected from the group consisting of hydrogen, halogens, and alkyl groups comprising 1 to 6 carbons.

In this instance the linking group N(H)C(=O)O-$D^5$ corresponds to divalent linking group $D^1$ of formula (A-2).

The catechol repeat units can comprise a catecholamine moiety such as, for example, a moiety derived from dopamine, epinephrine, norepinephrine, and/or L-dihydroxyphenylalanine (L-DOPA), derivatives of any of the foregoing, and combinations thereof. These catechol repeat units are referred to as "catecholamine repeat units" and have a structure according to formula (A-7):

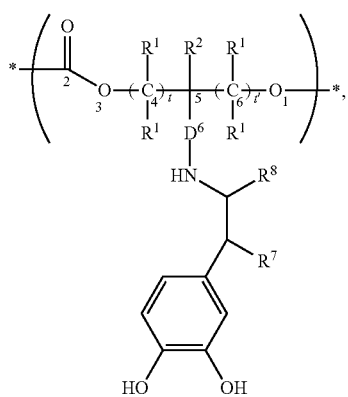

(A-7)

wherein $D^6$ is a divalent linking group comprising at least 1 carbon, each $R^1$ is an independent monovalent radical selected from the group consisting of hydrogen, halogens, methyl, and ethyl, $R^2$ is a monovalent radical selected from the group consisting of hydrogen, halogens, and alkyl groups comprising 1 to 6 carbons.

$R^7$ is a monovalent radical selected from the group consisting of hydrogen and hydroxyl (OH), $R^8$ is a monovalent radical selected from the group consisting of hydrogen and carboxyl (COOH), t is a positive integer having a value of 0 to 2, t' is a positive integer having a value of 0 to 2, and t and t' cannot both be zero.

Exemplary $D^6$ linking groups include:

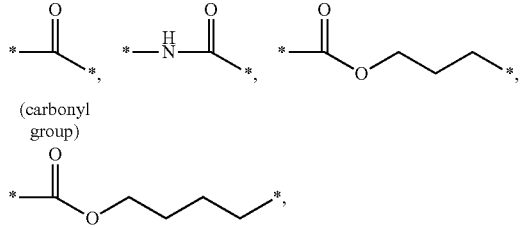
(carbonyl group)

-continued

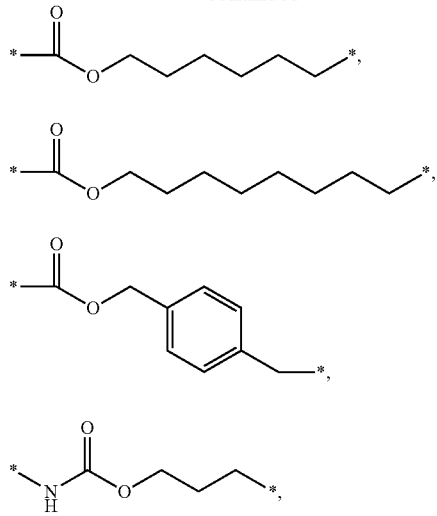

and combinations thereof. In the above examples, the left starred bond in the structure is linked to the polycarbonate backbone (e.g., the backbone carbon labeled 5 in the above cationic carbonate repeat units), and the right starred bond is linked to the nitrogen of the catecholamine moiety of formula (A-7).

More specific catecholamine repeat units have a structure according to formula (A-8):

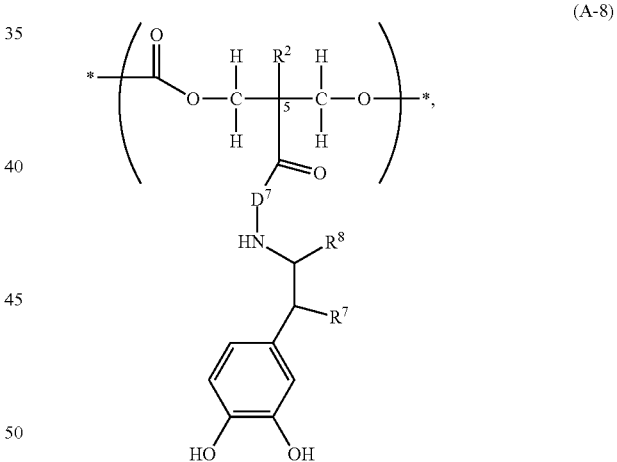

(A-8)

wherein $D^7$ is a single bond or a divalent linking group comprising at least 1 carbon, $R^2$ is a monovalent radical selected from the group consisting of hydrogen, halogens, and alkyl groups comprising 1 to 6 carbons.

$R^7$ is a monovalent radical selected from the group consisting of hydrogen and hydroxyl (OH), and $R^8$ is a monovalent radical selected from the group consisting of hydrogen and carboxyl (COOH).

Other more specific catecholamine repeat units have a structure according to formula (A-9):

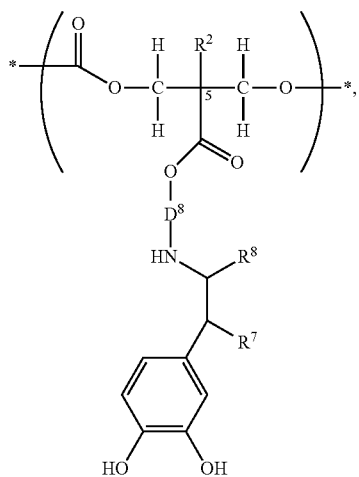

(A-9)

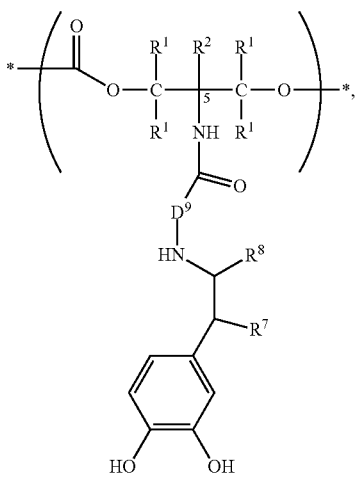

(A-10)

wherein
- $D^8$ is a divalent linking group comprising at least 1 carbon,
- $R^2$ is a monovalent radical selected from the group consisting of hydrogen, halogens, and alkyl groups comprising 1 to 6 carbons.
- $R^7$ is a monovalent radical selected from the group consisting of hydrogen and hydroxyl (OH), and
- $R^8$ is a monovalent radical selected from the group consisting of hydrogen and carboxyl (COOH).

In an embodiment, the catechol repeat unit has the formula (A-9), $R^2$ is methyl, $R^7$ and $R^8$ are hydrogen, $D^8$ is

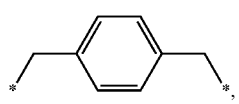

and the catechol repeat unit has the structure

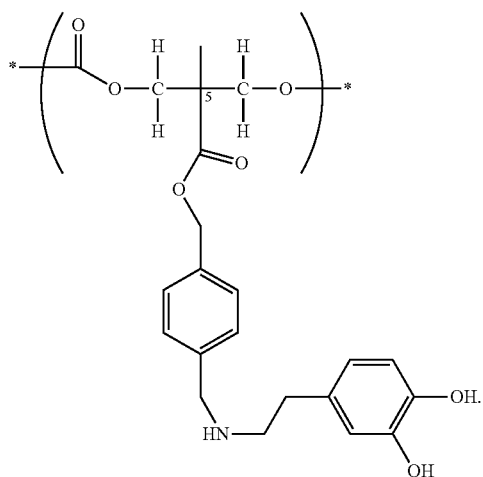

Other more specific catecholamine repeat units have a structure according to formula (A-10):

wherein
- $D^9$ is a divalent linking group comprising at least 1 carbon,
- each $R^1$ is an independent monovalent radical selected from the group consisting of hydrogen, halogens, methyl, and ethyl,
- $R^2$ is a monovalent radical selected from the group consisting of hydrogen, halogens, and alkyl groups comprising 1 to 6 carbons.
- $R^7$ is a monovalent radical selected from the group consisting of hydrogen and hydroxyl (OH), and
- $R^8$ is a monovalent radical selected from the group consisting of hydrogen and carboxyl (COOH).

Other more specific catecholamine repeat units have a structure according to formula (A-11):

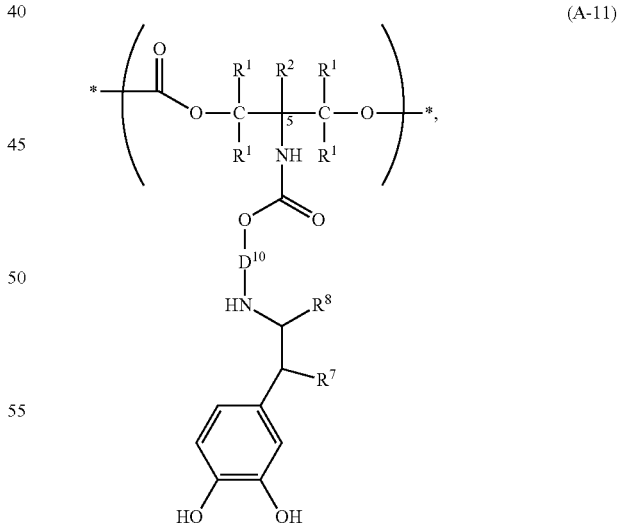

(A-11)

wherein
- $D^{10}$ is a divalent linking group comprising at least 1 carbon,
- each $R^1$ is an independent monovalent radical selected from the group consisting of hydrogen, halogens, methyl, and ethyl, $R^2$ is a monovalent radical selected from the group consisting of hydrogen, halogens, and alkyl groups comprising 1 to 6 carbons.

$R^7$ is a monovalent radical selected from the group consisting of hydrogen and hydroxyl (OH), and $R^8$ is a monovalent radical selected from the group consisting of hydrogen and carboxyl (COOH).

Cationic Carbonate Repeat Units

For antimicrobial applications, the catechol polymers are preferably random copolymers comprising a second carbonate repeat unit that comprises a side chain cationic group. These repeat units are referred to herein as "cationic repeat units". The cationic repeat units comprise an aliphatic carbonate backbone portion and a cationic side chain linked to the backbone portion. The cationic side chain comprises a cationic group selected from the group consisting of quaternary amine groups, quaternary phosphonium groups, and combinations thereof The cationic repeat units can have a structure according to formula (B-1):

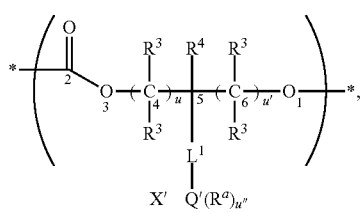
(B-1)

wherein $L^1$-$Q'(R^a)_{u''}$ is a $C_6$-$C_{25}$ cationic side chain comprising a quaternary ammonium group and/or quaternary phosphonium group, wherein $L^1$ is a divalent linking group comprising at least 3 carbons, Q' is a tetravalent positive-charged nitrogen or phosphorus, u" has a value of 1 to 3, each $R^a$ is an independent radical having a valency of 1 to 3, and each $R^a$ comprises at least 1 carbon, each $R^3$ is an independent monovalent radical selected from the group consisting of hydrogen, halogens, methyl, and ethyl, $R^4$ is a monovalent radical selected from the group consisting of hydrogen, halogens, and alkyl groups comprising 1 to 6 carbons, u is a positive integer having a value of 0 to 2, u' is a positive integer having a value of 0 to 2, u and u' cannot both be zero, and X' is a negative-charged ion.

The starred bonds of formula (B-1) are attachment points to other portions of the polymer structure. The polymer backbone atoms of the cationic repeat unit are labeled 1 to 6 in formula (B-1). In this instance, the cationic side chain group is linked to backbone carbon 5 of the cationic repeat unit. In an embodiment, t and t' are both 1, each $R^3$ is hydrogen, and $R^4$ is methyl or ethyl.

Exemplary non-limiting $L^1$ linking groups, include:

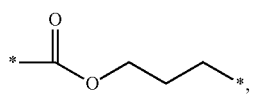

-continued

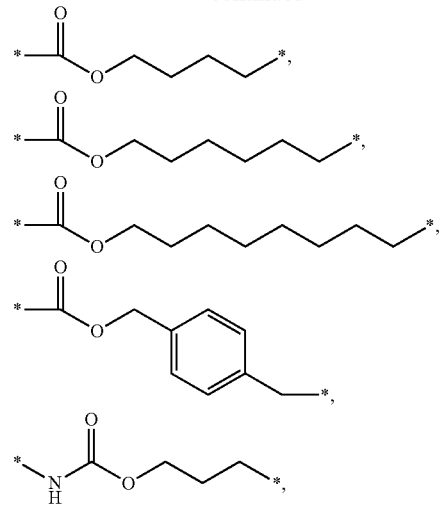

and combinations thereof. In the above examples, the starred bonds of the carbonyl and carbamate nitrogen are linked to the polycarbonate backbone (e.g., the backbone carbon labeled 5 in the above cationic carbonate repeat units), and the starred bonds of the methylene groups are linked to Q'.

Together, $L^1$ and $Q'(R^a)_{u''}$ form a quaternary ammonium group or a quaternary phosphonium group, meaning the positive-charged heteroatom Q' is bonded to a carbon of $L^1$ and up to three independent $R^a$ groups.

Each $R^a$ comprises at least one carbon. Each $R^a$ can be a monovalent hydrocarbon substituent (e.g., methyl, ethyl, etc.), in which case u" is 3.

An $R^a$ can form a ring with Q', in which case the $R^a$ of the ring has a valency of 2. For example, $Q'(R^a)_{u''}$ can be:

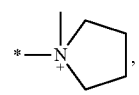

wherein the starred bond is linked to $L^1$, Q' is nitrogen, and u" is 2. In this example, a first $R^a$ is a divalent butylene group (*—$(CH_2)_4$—*), and a second $R^a$ is methyl.

$R^a$ can form a multi-cyclic moiety with Q'. For example $Q'(R^a)_{u''}$ can be:

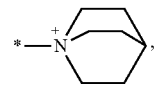

wherein the starred bond is linked to $L^1$, Q' is nitrogen, u' is 1, and $R^a$ is the fragment

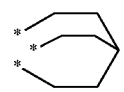

having a valency of 3.

The $R^a$ groups can also independently comprise oxygen, nitrogen, sulfur, and/or another heteroatom. In an embodiment, each $R^a$ is an independent monovalent branched or unbranched hydrocarbon substituent.

Exemplary non-limiting $R^a$ groups include methyl, ethyl, n-propyl, iso-propyl, n-butyl, iso-butyl, n-pentyl, n-hexyl, n-heptyl, n-octyl, and benzyl. The $R^a$ groups can be used in combination.

Exemplary non-limiting $Q'(R^a)_{u''}$ groups include:

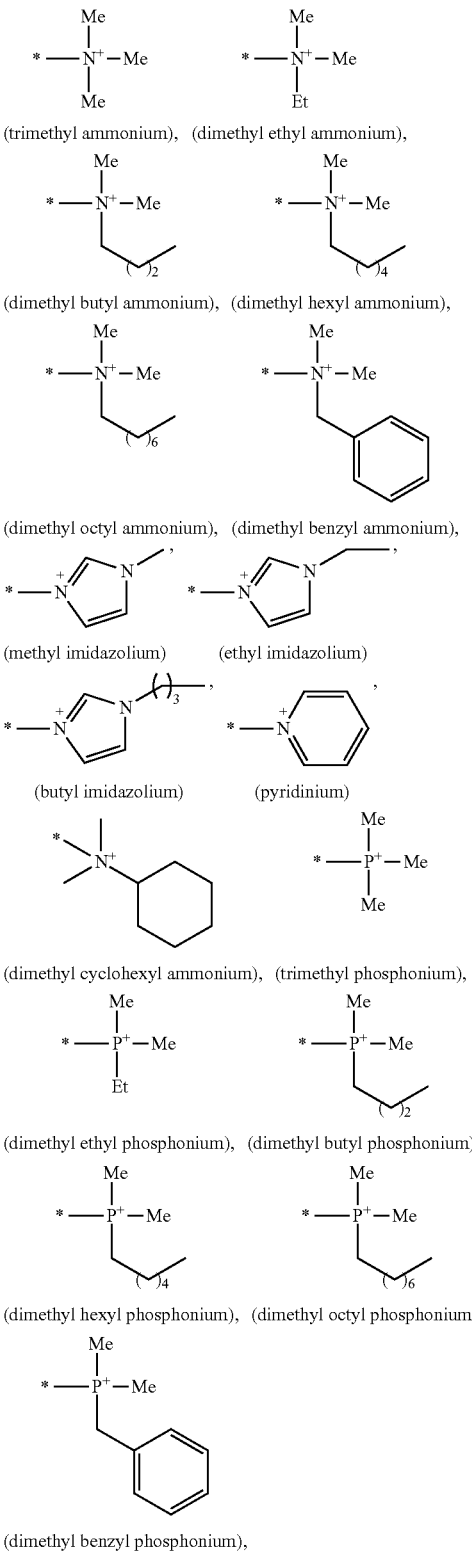

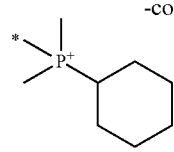

(dimethyl cyclohexyl phosphonium), and combinations thereof.

In the foregoing examples, it should be understood that the positive-charged nitrogen and phosphorus are tetravalent, and the starred bond is linked to a carbon of $L^1$. The Q' groups can be present in the cationic polymer singularly or in combination.

Exemplary negative-charged ions X' include halides (e.g., chloride, bromide, and iodide), carboxylates (e.g., acetate and benzoate), and/or sulfonates (e.g., tosylate). The X' ions can be present singularly or in combination.

More specific cationic repeat units have a structure in accordance with formula (B-2):

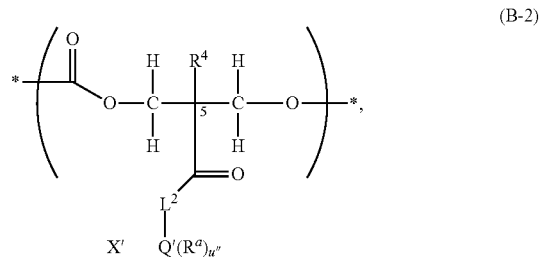

wherein $L^2\text{-}Q'(R^a)_{u''}$ is a $C_5$-$C_{24}$ cationic moiety comprising a quaternary ammonium group and/or quaternary phosphonium group, wherein $L^2$ is a divalent linking group comprising at least 2 carbons, Q' is a tetravalent positive-charged nitrogen or phosphorus, u'' has a value of 1 to 3, each $R^a$ is an independent radical having a valency of 1 to 3, and each $R^a$ comprises at least 1 carbon, $R^4$ is a monovalent radical selected from the group consisting of hydrogen, halogens, and alkyl groups comprising 1 to 6 carbons, and X' is a negative-charged ion.

In this instance, the cationic side chain group is $C(=O)\text{-}L^2\text{-}Q'(R^a)_{u''}$ and $C(=O)L^2$ corresponds to divalent linking group $L^1$ of formula (B-1). The cationic side chain is linked to backbone carbon labeled 5. Together, $L^2$ and $Q'(R^a)_{u''}$ form a quaternary ammonium group or a quaternary phosphonium group, meaning the positive-charged heteroatom Q' is bonded to a carbon of $L^2$ and up to three independent $R^a$ groups.

Other more specific cationic repeat units have a structure in accordance with formula (B-3):

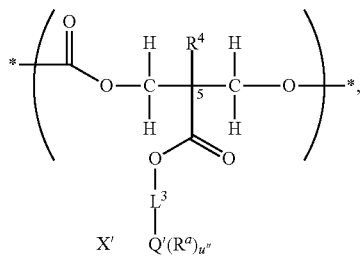

(B-3)

wherein
$L^3\text{-}Q'(R^a)_{u''}$ is a $C_5\text{-}C_{24}$ cationic moiety comprising a quaternary ammonium group and/or quaternary phosphonium group, wherein $L^3$ is a divalent linking group comprising at least 2 carbons, $Q'$ is a tetravalent positive-charged nitrogen or phosphorus, u" has a value of 1 to 3, each $R^a$ is an independent radical having a valency of 1 to 3, and each $R^a$ comprises at least 1 carbon, $R^4$ is a monovalent radical selected from the group consisting of hydrogen, halogens, and alkyl groups comprising 1 to 6 carbons, and $X'$ is a negative-charged ion.

In this instance, the cationic side chain group is C(=O)O-$L^3$-$Q'(R^a)_{u''}$ and C(=O)O-$L^3$ corresponds to divalent linking group $L^1$ of formula (B-1). The cationic side chain is linked to backbone carbon labeled 5. Together, $L^3$ and $Q'(R^a)_{u''}$ form a quaternary ammonium group or a quaternary phosphonium group, meaning the positive-charged heteroatom $Q'$ is bonded to a carbon of $L^3$ and up to three independent $R^a$ groups.

Other more specific cationic repeat units have a structure in accordance with formula (B-4):

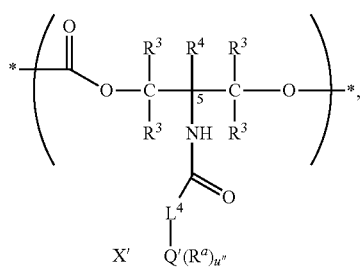

(B-4)

wherein
$L^4\text{-}Q'(R^a)_{u''}$ is a $C_5\text{-}C_{24}$ cationic moiety comprising a quaternary ammonium group and/or quaternary phosphonium group, wherein $L^4$ is a divalent linking group comprising at least 2 carbons, $Q'$ is a tetravalent positive-charged nitrogen or phosphorus, u" has a value of 1 to 3, and each $R^a$ is an independent radical having a valency of 1 to 3, wherein each $R^a$ comprises at least 1 carbon, each $R^3$ is an independent monovalent radical selected from the group consisting of hydrogen, halogens, methyl, and ethyl, $R^4$ is a monovalent radical selected from the group consisting of hydrogen, halogens, and alkyl groups comprising 1 to 6 carbons, and $X'$ is a negative-charged ion.

In this instance the cationic side chain is N(H)C(=O)$L^4$-$Q'(R^a)_{u''}$ and N(H)C(=O)$L^4$ corresponds to divalent linking group $L^1$ of formula (B-1). The cationic side chain is linked to backbone carbon labeled 5. Serinol and/or threoninol provide useful starting materials for the formation of repeat units of formula (B-2). Together, $L^4$ and $Q'(R^a)_{u''}$ form a quaternary ammonium group or a quaternary phosphonium group, meaning the positive-charged heteroatom $Q'$ is bonded to a carbon of $L^4$ and up to three independent $R^a$ groups.

Other more specific cationic repeat units have a structure in accordance with formula (B-5):

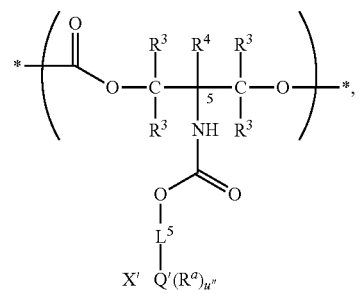

(B-5)

wherein
$L^5\text{-}Q'(R^a)_{u''}$ is a $C_5\text{-}C_{24}$ cationic moiety comprising a quaternary ammonium group and/or quaternary phosphonium group, wherein $L^5$ is a divalent linking group comprising at least 2 carbons, $Q'$ is a tetravalent positive-charged nitrogen or phosphorus, u" has a value of 1 to 3, and each $R^a$ is an independent radical having a valency of 1 to 3, wherein each $R^a$ comprises at least 1 carbon, each $R^3$ is an independent monovalent radical selected from the group consisting of hydrogen, halogens, methyl, and ethyl, $R^4$ is a monovalent radical selected from the group consisting of hydrogen, halogens, and alkyl groups comprising 1 to 6 carbons, and $X'$ is a negative-charged ion.

In this instance the cationic side chain is N(H)C(=O)O-$L^5$-$Q'(R^a)_{u''}$ and N(H)C(=O)O-$L^5$ corresponds to divalent linking group $L^1$ of formula (B-1). The cationic side chain is linked to backbone carbon labeled 5. Together, $L^5$ and $Q'(R^a)_{u''}$ form a quaternary ammonium group or a quaternary phosphonium group, meaning the positive-charged heteroatom $Q'$ is bonded to a carbon of $L^5$ and up to three independent $R^a$ groups.

Exemplary non-limiting cationic repeat units include the following:

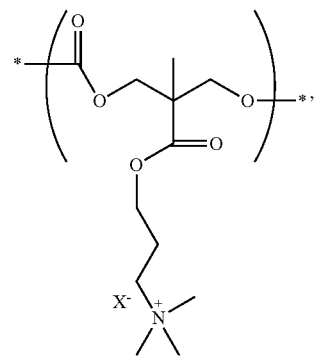

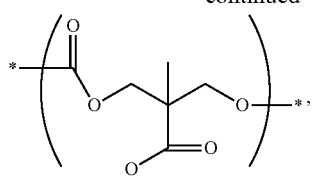
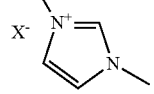
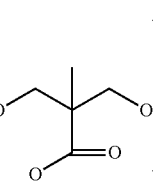
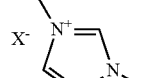
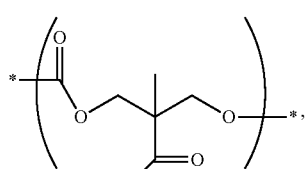
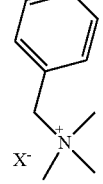
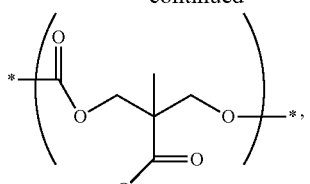
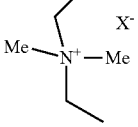
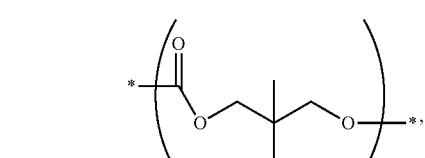
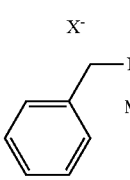
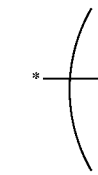
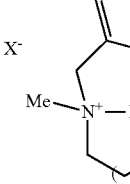

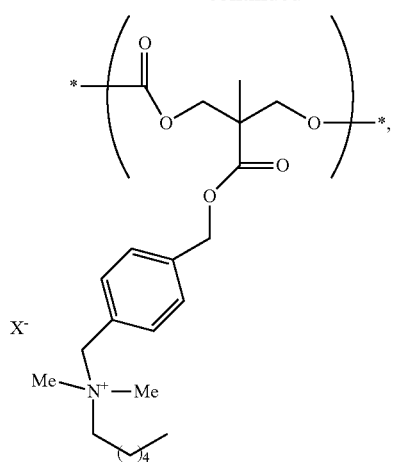
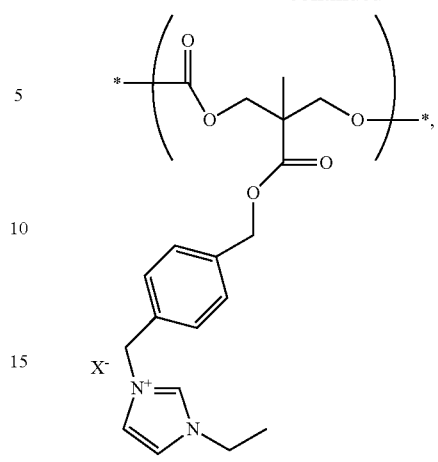
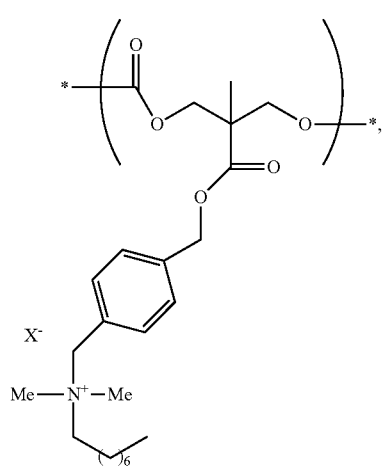
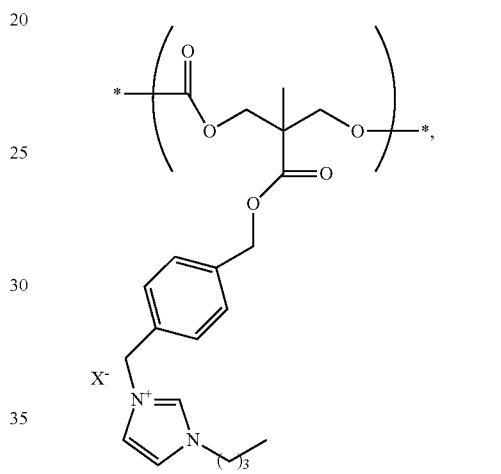
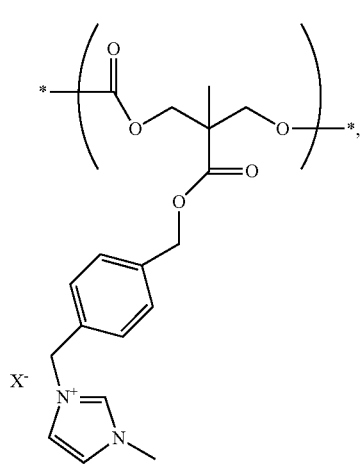
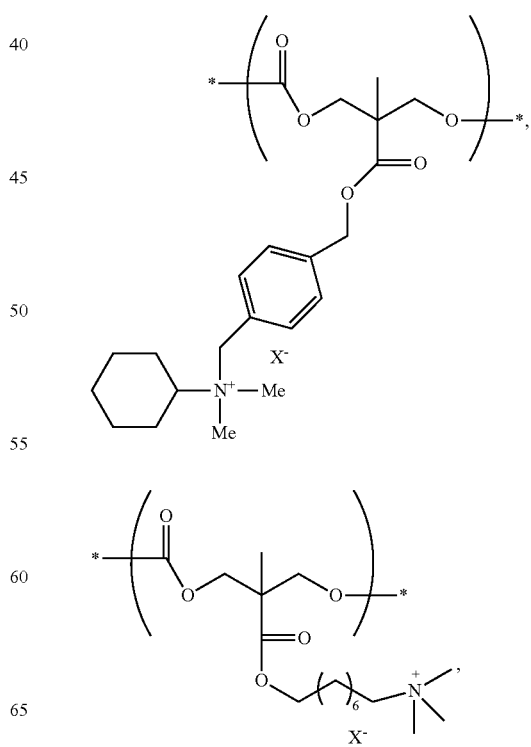

23
-continued
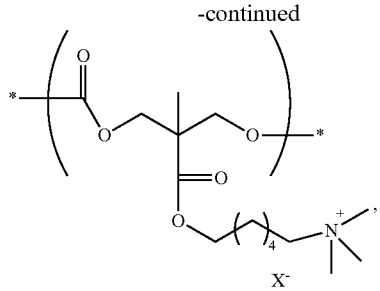
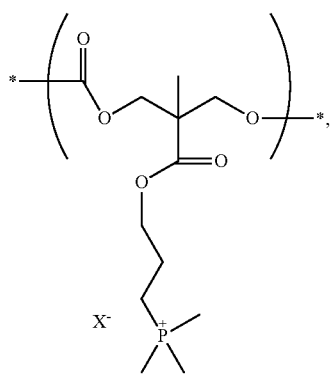
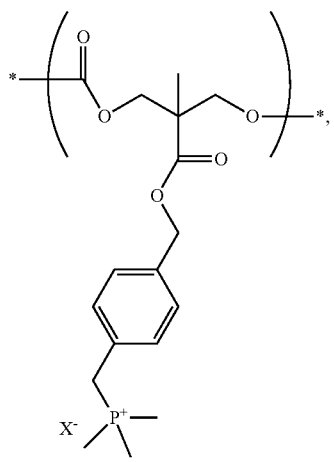
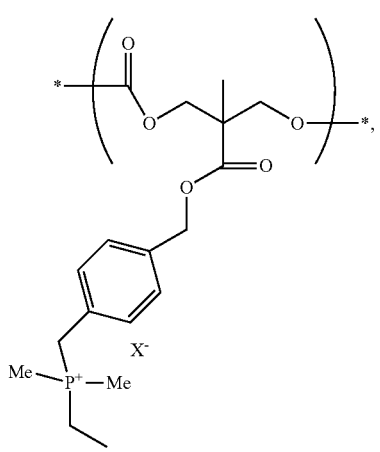
24
-continued
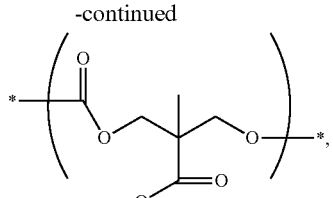
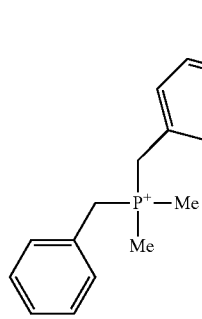
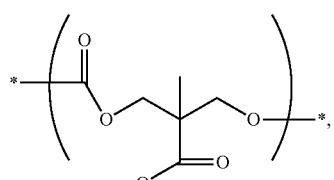
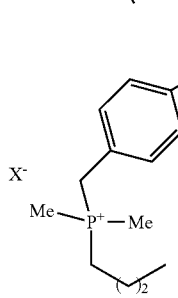
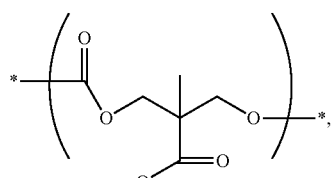
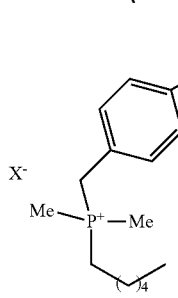

-continued

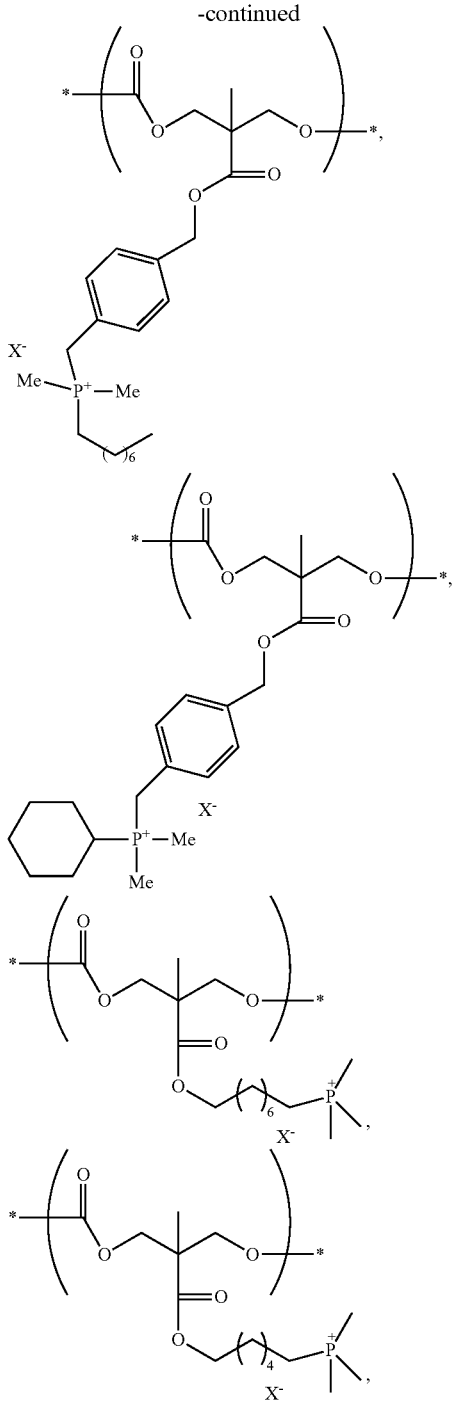

and combinations thereof, wherein $X^-$ is a negative-charged ion.

In general, antimicrobial activity of the catechol polymers is favored by spacing the positive-charged heteroatom Q' from the polycarbonate backbone in 25 mol % to 100 mol % of the cationic repeat units (designated first cationic repeat units) by the shortest path having 6 or more contiguously linked atomic centers from the polymer backbone. The shortest path is defined as the lowest number of contiguously linked atomic centers joining Q' to the polymer backbone. The contiguously linked atomic centers should be understood to be between the polycarbonate backbone and Q'. For example, if $L^1$-Q' is:

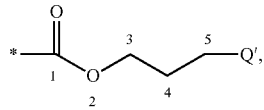

then the shortest path from the polymer backbone to Q' has 5 contiguously linked atomic centers, as numbered. The shortest path does not include the carbonyl oxygen. As another example, if $L^1$-Q' is

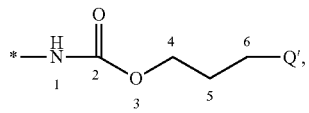

then the shortest path from the polymer backbone to Q' has 6 contiguously linked atomic centers, as numbered. The shortest path does not include the amide hydrogen and the carbonyl oxygen. As another example, if $L^1$-Q' is

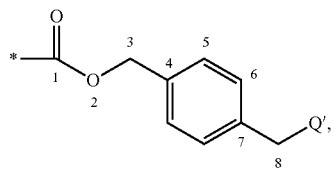

then the shortest path from the polymer backbone to Q' has 8 contiguously linked atomic centers, as numbered. The shortest path does not include two carbons of the aromatic ring and the carbonyl oxygen. As another example, if $L^1$-Q' is

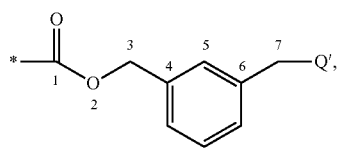

then the shortest path from the polymer backbone to Q' has 7 contiguously linked atomic centers, as numbered. The shortest path does not include three carbons of the aromatic ring and the carbonyl oxygen. Finally, as another example, if $L^1$-Q' is

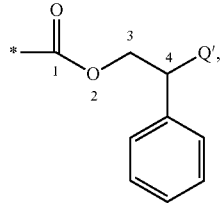

then the shortest path from the polymer backbone to Q' has 4 contiguously linked atomic centers, as numbered. The shortest path does not include the aromatic ring and the carbonyl oxygen.

Preferably, Q' of the first cationic repeat units is spaced from the polymer backbone by a shortest path having 6 to about 18 contiguously linked atomic centers, and more preferably 8 to about 15 contiguously linked atomic centers.

In an embodiment, about 25% to 100% of all the cationic repeat units of the catechol polymer, designated first cationic repeat units, have a cationic side chain comprising 10 to about 25 carbons, and 0% to about 75% of the cationic repeat units of the catechol polymer, designated second cationic repeat units, have a cationic side chain comprising 6 to 9 carbons. For example, $L^1$ and $Q'(R^a)_{u''}$ of the first cationic repeat units can individually have 3 to about 22 carbons, with the proviso that $L^1$-$Q'(R^a)_{u''}$ has a total of 10 to about 25 carbons. In an embodiment, the first cationic repeat units have a cationic side chain $L^1$-$Q'(R^a)_{u''}$ comprising 13 to about 25 carbons, and the second cationic repeat units have a cationic side chain $L^1$-$Q'(R^a)_{u''}$ comprising 6 to 12 carbons.

In another embodiment, the positive-charged heteroatom Q' of the first cationic repeat units is spaced from the backbone portion by a shortest path having 6 to about 15 contiguously linked atomic centers between Q' and the backbone portion.

Oligomeric Poly(Ethylene Oxide)-Containing Carbonate Repeat Units

For anti-fouling applications, the catechol polymers preferably comprise a third carbonate repeat unit comprising an oligomeric poly(ethylene oxide) group. This repeat unit can be prepared from a poly(ethylene glycol) (PEG), and is therefore referred to as a "PEG repeat unit". The PEG repeat unit comprises an aliphatic carbonate backbone portion and a side chain linked to the backbone portion that contains a poly(ethylene oxide) chain (PEG chain). The PEG chain can have a degree of polymerization of about 5 to about 30, more specifically about 10 to about 25, and even more specifically about 10 to about 20 in ethylene oxide subunits. The PEG chain can be endcapped or non-endcapped (i.e., have a terminal hydroxy group at the end of the PEG chain farthest from the carbonate backbone portion).

The PEG repeat units have a structure according to formula (C-1):

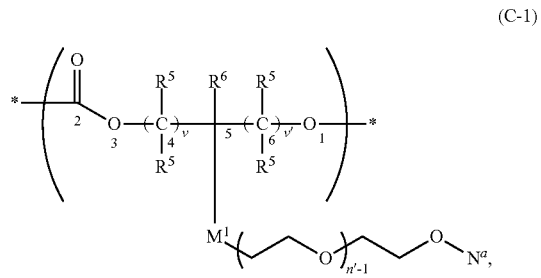

wherein
n' is an integer of about 5 to about 30,
$M^1$ is a divalent linking group comprising at least 1 carbon,
$N^a$ is a monovalent end group selected from the group consisting of hydrogen and radicals comprising at least 1 carbon,
each $R^5$ is an independent monovalent radical selected from the group consisting of hydrogen, halogens, methyl, and ethyl,
$R^6$ is a monovalent radical selected from the group consisting of hydrogen, halogens, and alkyl groups comprising 1 to 6 carbons,
v is a positive integer having a value of 0 to 2,
v' is a positive integer having a value of 0 to 2, and
v and v' cannot both be zero.

The starred bonds of formula (C-1) are attachment points to other portions of the polymer structure. The atoms of the carbonate backbone portion of the PEG repeat unit are labeled 1 to 6 in formula (C-1). In an embodiment, v and v' are both 1, each $R^5$ is hydrogen, and $R^6$ is methyl or ethyl.

More specific PEG repeat units can have a structure in accordance with formula (C-2):

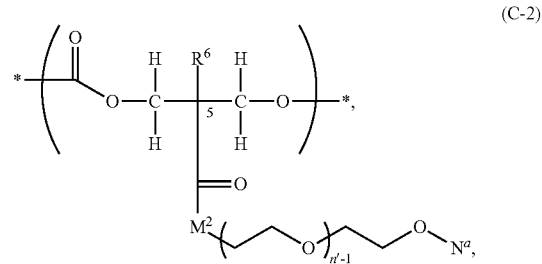

wherein
n' is an integer of about 5 to about 30,
$M^2$ is a divalent linking group,
$N^a$ is a monovalent radical selected from the group consisting of hydrogen and groups comprising at least 1 carbon, and
$R^6$ is a monovalent radical selected from the group consisting of hydrogen, halogens, and alkyl groups comprising 1 to 6 carbons.

In this instance, the PEG side chain group is C(=O)$M^2$-(CH$_2$CH$_2$O) CH$_2$CH$_2$ON$^a$ and C(=O)$M^2$ corresponds to divalent linking group $M^1$ of formula (C-1). In this instance, the side chain is linked to backbone carbon labeled 5.

In an embodiment, $M^2$ is a divalent radical selected from the group consisting of O, NH, NR', S, and combinations thereof, wherein R' is a monovalent radical comprising 1 to 6 carbons.

Other specific PEG repeat units have a structure in accordance with formula (C-3):

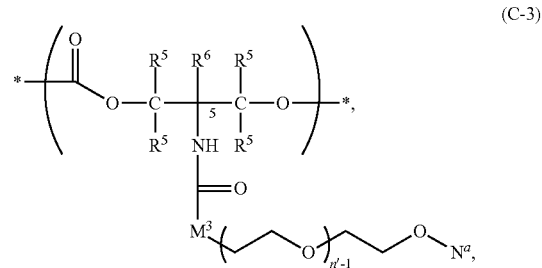

wherein
n' is an integer of about 5 to about 30,
$M^3$ is a divalent linking group,
each $R^5$ is an independent monovalent radical selected from the group consisting of hydrogen, halogens, methyl, and ethyl,
$R^6$ is a monovalent radical selected from the group consisting of hydrogen, halogens, and alkyl groups comprising 1 to 6 carbons, and
X' is a negative-charged ion.

In this instance the PEG side chain is N(H)C(=O)$M^3$-(CH$_2$CH$_2$O)$_{n-1}$ CH$_2$CH$_2$ON$^a$ and N(H)C(=O)$M^3$ corresponds to divalent linking group $M^1$ of formula (C-1). The cationic side chain is linked to backbone carbon labeled 5. Serinol and/or threoninol provide useful starting materials for the formation of repeat units of formula (C-3).

The catechol polymer can be a homopolymer, random copolymer, block copolymer, or a mixture thereof. Preferably, the catechol polymer is a linear random copolymer, and more specifically, a linear polymer comprising one polycarbonate chain (one-armed catechol polymer) or two polycarbonate chains (two-armed catechol polymer).

In an embodiment, $M^3$ is a divalent radical selected from the group consisting of O, NH, NR', S, and combinations thereof, wherein R' is a monovalent radical comprising 1 to 6 carbons.

The foregoing catechol repeat units, cationic repeat units, and/or PEG repeat units can be present in the catechol polymer in stereospecific or non-stereospecific form.

Catechol Polymers Having One Polymer Chain (One-Armed)

One-armed catechol polymers have a structure in accordance with formula (D-1):

$$Z'—P'—Z'' \quad (D-1),$$

wherein
- Z' is a monovalent first end group, wherein Z' comprises at least 1 carbon and a heteroatom selected from the group consisting of N, O, and S, wherein the heteroatom is linked to a backbone carbonyl group of P',
- Z'' is a monovalent second end group selected from the group consisting of hydrogen and moieties comprising at least 1 carbon, and
- P' is a polycarbonate chain comprising a catechol repeat unit, wherein i) P' has a degree of polymerization (DP) of 1 or more, ii) the catechol repeat unit comprises a carbonate backbone portion and a side chain linked to the carbonate backbone portion, and iii) the side chain comprises a catechol group.

Using the catechol repeat unit of formula (A-2), a catechol polymer can have a structure in accordance with formula (D-2):

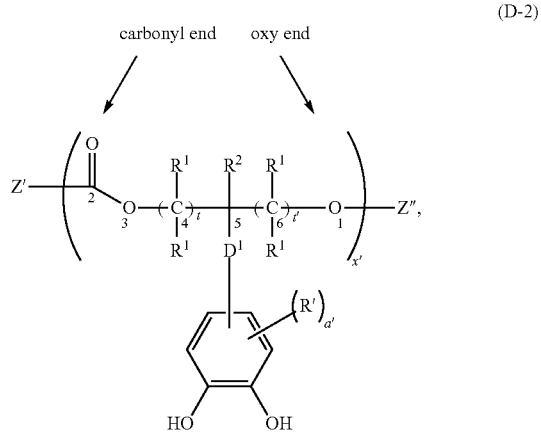

wherein:
- Z' is a monovalent first end group comprising at least 1 carbon and a heteroatom selected from the group consisting of N, O, and S, wherein the heteroatom is linked to a backbone carbonyl group of the catechol polymer,
- Z'' is a monovalent second end group selected from the group consisting of hydrogen and moieties comprising at least 1 carbon,
- x' represents the number of catechol repeat units, wherein x' has a value of 1 or more, each $D^1$ is an independent divalent linking group comprising at least 1 carbon, each $R^1$ is an independent monovalent radical selected from the group consisting of hydrogen, halogens, methyl, and ethyl, each $R^2$ is an independent monovalent radical selected from the group consisting of hydrogen, halogens, and alkyl groups comprising 1 to 6 carbons, each R' is an independent monovalent radical selected from the group consisting of halogens, methyl, and ethyl, each a' is an independent integer of 0 to 3, each t is an independent positive integer having a value of 0 to 2, each t' is an independent positive integer having a value of 0 to 2, and no catechol repeat unit has t=0 and t'=0.

As shown in formula (D-2), the polymer chain comprises a backbone portion comprising an oxycarbonyl group at a first end of the chain (referred to as the "carbonyl end"), and a backbone oxygen at a second end of the chain (referred to as the "oxy end"). The backbone atoms of the cationic carbonate repeat unit are shown numbered 1 to 6.

Using the catechol repeat unit of formula (A-2), the cationic repeat unit of formula (B-1) and the PEG repeat unit of formula (C-1), an antimicrobial and/or antifouling one-armed catechol polymer can have a structure in accordance with formula (D-3):

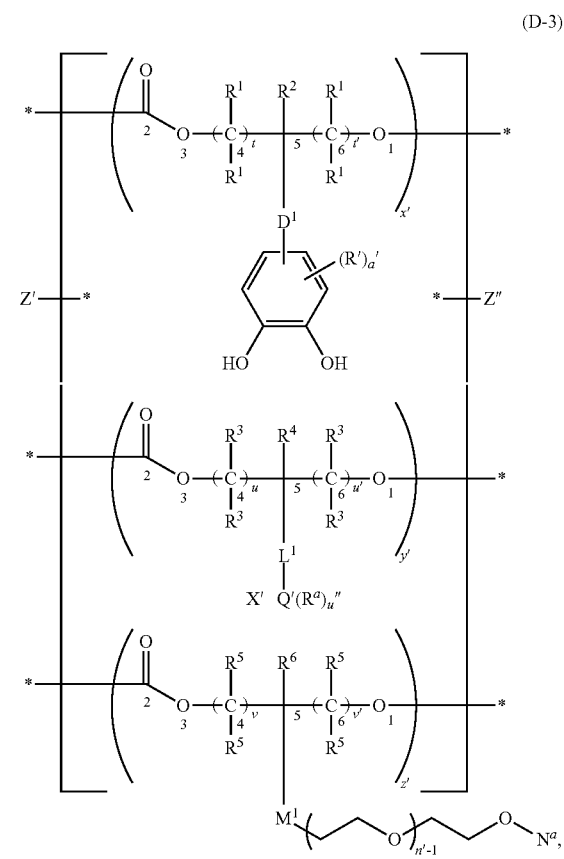

wherein
1) Z' is a monovalent first end group, wherein Z' comprises at least 1 carbon and a heteroatom selected from the group consisting of N, O, and S, wherein the heteroatom is linked to a backbone carbonyl group of the catechol polymer, 2) Z" is a monovalent second end group selected from the group consisting of hydrogen and moieties comprising at least 1 carbon, 3) with respect to catechol repeat units comprising linking group $D^1$:

x' is a positive number having a value of 1 or more, each $D^1$ is an independent divalent linking group comprising at least 1 carbon, each $R^1$ is an independent monovalent radical selected from the group consisting of hydrogen, halogens, methyl, and ethyl, each $R^2$ is an independent monovalent radical selected from the group consisting of hydrogen, halogens, and alkyl groups comprising 1 to 6 carbons, each R' is an independent monovalent radical selected from the group consisting of halogens, methyl, and ethyl, a' is an integer of 0 to 3, each t is an independent positive integer having a value of 0 to 2, each t' is an independent positive integer having a value of 0 to 2, and t and t' cannot both be zero in any catechol repeat unit, 4) with respect to cationic repeat units:

y' is a number having a value greater than or equal to 1, each $L^1$-$Q'(R^a)_{u''}$ is an independent $C_6$-$C_{25}$ cationic side chain comprising a quaternary ammonium group and/or quaternary phosphonium group, wherein $L^1$ is an independent divalent linking group comprising at least 3 carbons, Q' is a tetravalent positive-charged nitrogen or phosphorus, u" has a value of 1 to 3, each $R^a$ is an independent radical having a valency of 1 to 3, and each $R^a$ comprises at least 1 carbon, each $R^3$ is an independent monovalent radical selected from the group consisting of hydrogen, halogens, methyl, and ethyl, each $R^4$ is an independent monovalent radical selected from the group consisting of hydrogen, halogens, and alkyl groups comprising 1 to 6 carbons, each u is an independent positive integer having a value of 0 to 2, each u' is an independent positive integer having a value of 0 to 2, u and u' cannot both be zero in any cationic repeat unit, and each X' is an independent negative-charged ion, and 5) with respect to PEG repeat units:

z' is a number having a value greater than or equal to 1, n' is a positive integer of about 5 to about 30, each $M^1$ is an independent divalent linking group comprising at least 1 carbon, each $N^a$ is an independent monovalent radical selected from the group consisting of hydrogen and groups comprising at least 1 carbon, each $R^5$ is an independent monovalent radical selected from the group consisting of hydrogen, halogens, methyl, and ethyl, each $R^6$ is an independent monovalent radical selected from the group consisting of hydrogen, halogens, and alkyl groups comprising 1 to 6 carbons, each v is an independent positive integer having a value of 0 to 2, each v' is an independent positive integer having a value of 0 to 2, and v and v' cannot both be zero in any PEG repeat unit.

The vertical stacking of the repeat units within the square brackets of formula (D-3) represents random distribution of the repeat units enclosed by the brackets. Thus, the P' chain is a random copolymer chain of the repeat units shown in the brackets. Any one of the repeat units within the brackets can be linked to Z' and/or Z" in a given polycarbonate chain. The subscripts x', y', and z' represent numbers of the respective repeat units in a polycarbonate chain. In an embodiment, a' is 0, each of t, t', u, u', v, and v' is 1, each of $R^2$, $R^4$, and $R^6$ is methyl, and each of $R^1$, $R^3$, $R^5$ and Z" is hydrogen. In another embodiment, the cationic repeat units have a side chain group $L^1$-$Q'(R^a)_{u''}$ comprising 15 to about 25 carbons.

In a specific embodiment, the catechol polymer is a one-armed random copolymer having the formula (D-4):

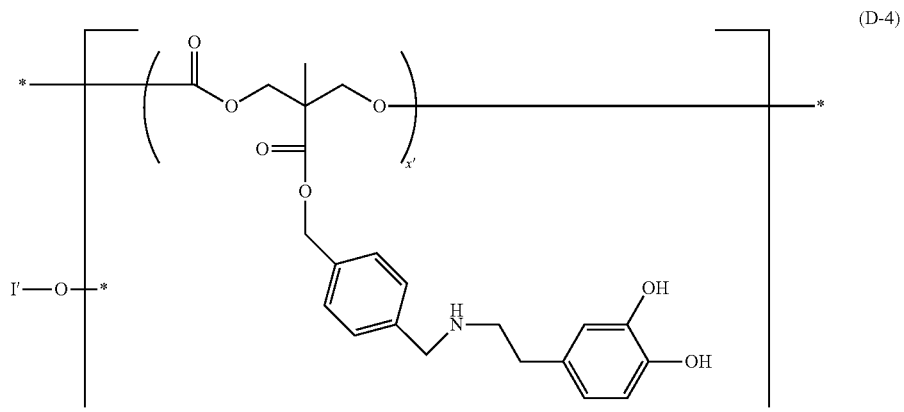

(D-4)

-continued

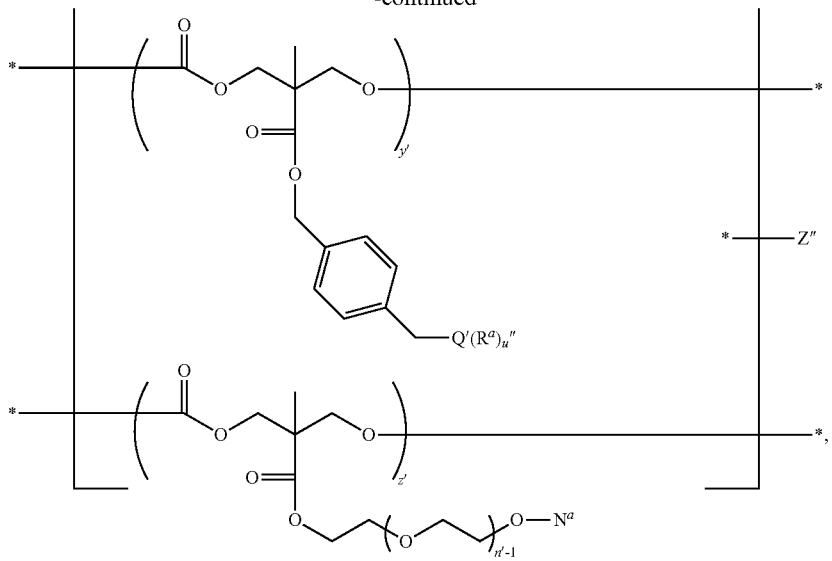

wherein
I'—O is a monovalent first end group, wherein I' comprises at least 1 carbon,
each Q' is an independent tetravalent positive-charged nitrogen or phosphorus,
each u" is an independent positive integer having a value of 1 to 3,
each $R^a$ is an independent radical having a valency of 1 to 3, wherein each $R^a$ comprises at least 1 carbon,
Z" is a monovalent second end group selected from the group consisting of hydrogen and moieties comprising at least 1 carbon,
each $N^a$ is an independent monovalent radical selected from the group consisting of hydrogen and groups comprising at least 1 carbon,
R is a monovalent radical having at least 1 carbon,
x' is a positive number having a value of 1 or more,
y' is a positive number having a value of 1 or more,
z' is a positive number having a value of 1 or more.
n' is a positive number of about 5 to about 30, and
$X^-$ is a negative charged ion.

Subscript x' of formula (D-3) represents the number of catechol repeat units, and x' preferably has a value of 2 to 20, 2 to 10, or most preferably 2 to 8. Subscript y' of formula (D-3) represents the number of cationic repeat units, and y' preferably has a value of 1 to 100, 20 to 80, or more preferably 40 to 60. Subscript z' of formula (D-3) represents the number of PEG repeat units, and z' preferably has a value of 1 to 30, 2 to 15, or more preferably 5 to 15.

Catechol Polymers Having Two Polymer Chains (Two-Armed)

The catechol polymers can comprise two polycarbonate chains extending from a central core. These two-armed catechol polymers have a structure in accordance with formula (D-4):

$$Z^a—P^a—C'—P^b—Z^b \quad (D\text{-}4),$$

wherein
$P^a$ is a first polycarbonate chain comprising a first catechol repeat unit, wherein i) $P^a$ comprises 2 or more catechol repeat units, ii) each of the catechol repeat units comprises a carbonate backbone portion and a side chain linked to the backbone portion, and iii) the side chain comprises a catechol group,
$P^b$ is a second polycarbonate chain comprising a second catechol repeat unit, wherein $P^b$ comprises 2 or more catechol repeat units and each of the second catechol repeat units comprises a carbonate backbone portion and a side chain linked to the backbone portion, wherein the side chain comprises a catechol group,
C' is a divalent linking group joining $P^a$ and $P^b$, wherein C' comprises i) 2 or more carbons, ii) a first heteroatom selected from the group consisting of nitrogen, oxygen, and sulfur, wherein the first heteroatom is linked to $P^a$, and iii) a second heteroatom selected from the group consisting of nitrogen, oxygen, and sulfur linked to $P^b$, wherein the second heteroatom is linked to $P^b$,
$Z^a$ is a monovalent end group selected from the group consisting of hydrogen and moieties comprising at least 1 carbon, and
$Z^b$ is a monovalent end group selected from the group consisting of hydrogen and moieties comprising at least 1 carbon.

Using the catechol repeat unit of formula (A-2), the cationic repeat unit of formula (B-1) and the PEG repeat unit of formula (C-1), an antimicrobial and/or antifouling two-armed catechol polymer can have a structure in accordance with formula (D-5):

(D-5)

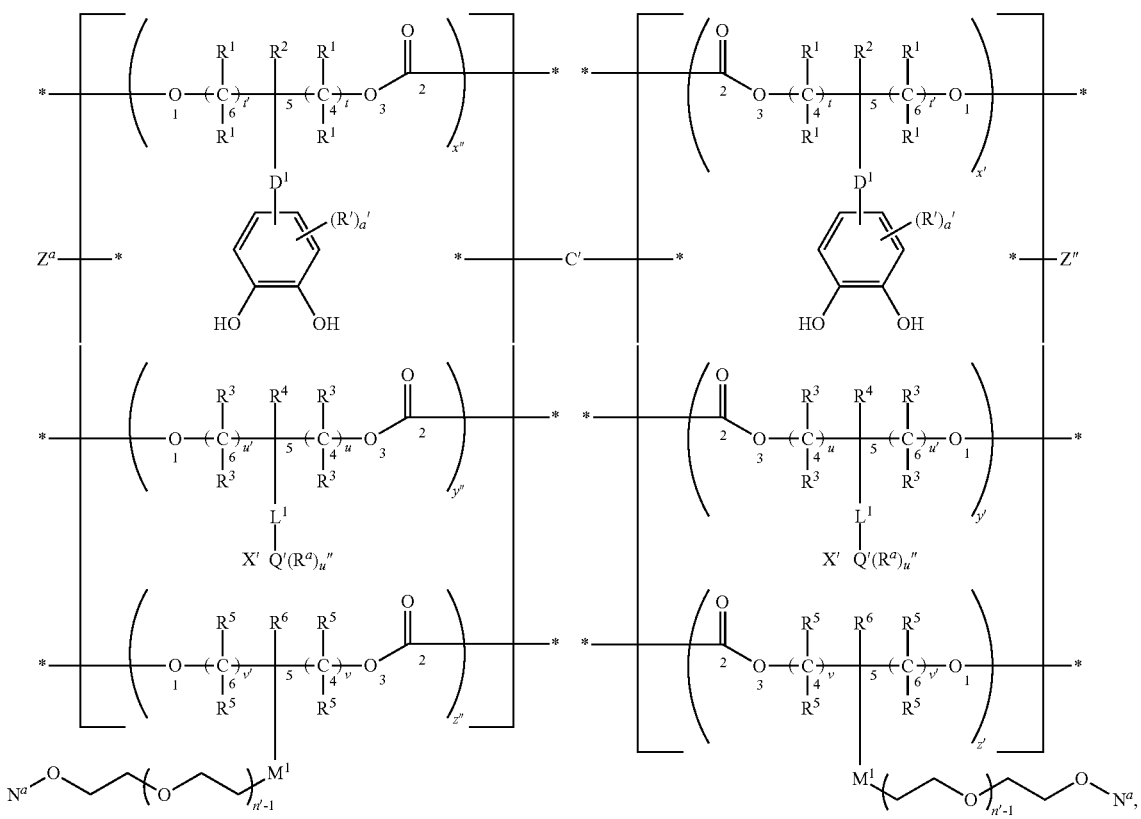

wherein
1) C' is a divalent radical comprising 2 or more carbons, a first heteroatom selected from the group consisting of N, O, and S, wherein the first heteroatom is linked to a backbone carbonyl group of a first polycarbonate chain $P^a$, and a second heteroatom selected from the group consisting of N, O, and S, wherein the second heteroatom is linked to a backbone carbonyl group of a second polycarbonate chain $P^b$,
2) $Z^a$ is a monovalent first end group selected from the group consisting of hydrogen and moieties comprising at least 1 carbon,
3) $Z^b$ is a monovalent first second group selected from the group consisting of hydrogen and moieties comprising at least 1 carbon,
4) with respect to catechol repeat units:
   x' is a positive number greater than or equal to 1,
   x" is a positive number greater than or equal to 1,
   each $D^1$ is an independent divalent linking group comprising at least 1 carbon,
   each $R^1$ is an independent monovalent radical selected from the group consisting of hydrogen, halogens, methyl, and ethyl,
   each $R^2$ is an independent monovalent radical selected from the group consisting of hydrogen, halogens, and alkyl groups comprising 1 to 6 carbons,
   each R' is an independent monovalent radical selected from the group consisting of halogens, methyl, and ethyl,
   each a' is an independent integer of 0 to 3,
   each t is an independent positive integer having a value of 0 to 2,
   each t' is an independent positive integer having a value of 0 to 2, and
   t and t' cannot both be zero in any catechol repeat unit,
5) with respect to cationic repeat units:
   y' is a positive number greater than or equal to 0,
   y" is a positive number greater than or equal to 0,
   each $L^1\text{-}Q'(R^a)_{u''}$ is an independent $C_6\text{-}C_{25}$ cationic side chain comprising a quaternary ammonium group and/or quaternary phosphonium group, wherein $L^1$ is a divalent linking group comprising at least 3 carbons, Q' is a tetravalent positive-charged nitrogen or phosphorus, u" has a value of 1 to 3, each $R^a$ is an independent radical having a valency of 1 to 3, and each $R^a$ comprises at least 1 carbon,
   each $R^3$ is an independent monovalent radical selected from the group consisting of hydrogen, halogens, methyl, and ethyl,
   each $R^4$ is an independent monovalent radical selected from the group consisting of hydrogen, halogens, and alkyl groups comprising 1 to 6 carbons,
   each u is an independent positive integer having a value of 0 to 2,
   each u' is an independent positive integer having a value of 0 to 2,
   u and u' cannot both be zero in any cationic repeat unit, and
   each X' is an independent negative-charged ion, and
6) with respect to PEG repeat units:
   z' is a positive number greater than or equal to 0,
   z" is a positive number greater than or equal to 0,
   n' is an integer of about 5 to about 30, each $M^1$ is an independent divalent linking group comprising at least 1 carbon, each $N^a$ is an independent monovalent radical selected from the group consisting of hydrogen and groups comprising at least 1 carbon, each $R^5$ is an independent monovalent radical selected from the group consisting of hydrogen, halogens, methyl, and ethyl, each $R^6$ is an independent monovalent radical selected from the group consisting of hydrogen, halogens, and alkyl groups comprising 1 to 6 carbons, each v is an independent positive integer having a value of 0 to 2, each v' is an independent positive integer having a value of 0 to 2, and v and v' cannot both be zero in any PEG repeat unit.

C' can be a residue of an initiator comprising two nucleophilic initiating sites for a ring opening polymerization.

It should be understood that the above-described catechol polymers can include additional carbonate repeat units to control hydrophilic-hydrophobic balance, film-forming properties, antimicrobial properties, antifouling properties, and other polymer properties.

Electrophilic Cyclic Carbonate Monomers

A preferred method of preparing the disclosed catechol polymers utilizes a cyclic carbonate monomer comprising an electrophilic group E' comprising a leaving group capable of reacting in a nucleophilic substitution reaction after ring open polymerization of the cyclic carbonate monomer. These monomers are referred to herein as "E-monomers". The E-monomers form an initial polycarbonate comprising carbonate repeat units bearing an E' group, referred to as "electrophilic repeat units". The electrophilic repeat units comprise a carbonate backbone portion and a side chain linked to the backbone portion, wherein the side chain comprises an E' group. It was found that a catecholamine such as dopamine, which bears a reactive primary amine group, can react preferentially with an E' group without significant degradation of the polycarbonate backbone or crosslinking of the resulting catechol polymer. When an excess of E' groups is present, the remaining electrophilic repeat units can then be treated with tertiary amines and tertiary phosphines to form cationic repeat units comprising quaternary amine groups and/or quaternary phosphonium groups. Thus, the catechol repeat units and cationic repeat units of the catechol polymer can be prepared from a common electrophilic repeat unit.

The E-monomers can have the formula (E-1):

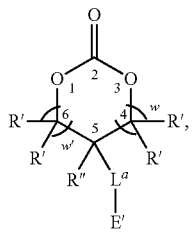

(E-1)

wherein the ring atoms are shown numbered 1 to 6, $L^a$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, w is a positive integer having a value of 0 to 2, w' is a positive integer having a value of 0 to 2, and w and w' cannot both be zero.

The ring substituent $L^a$-E' becomes a side chain of the initial polycarbonate formed in the ring opening polymerization of the E-monomer. In an embodiment, w and w' of formula (E-1) are each 1, each R' at carbon 4 is hydrogen, each R' at carbon 6 is hydrogen, and R" at carbon 5 is selected from the group consisting of hydrogen, methyl, and ethyl. The E-monomers can be stereospecific or non-stereospecific.

Ring opening polymerization of E-monomers of formula (E-1) produces an initial polycarbonate having a repeat unit according to formula (E-2):

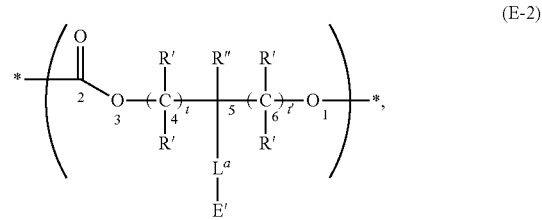

(E-2)

wherein backbone atoms are shown numbered 1 to 6, $L^a$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, t is a positive integer having a value of 0 to 2, t' is a positive integer having a value of 0 to 2, and t and t' cannot both be zero.

More specific E-monomers have the formula (E-3):

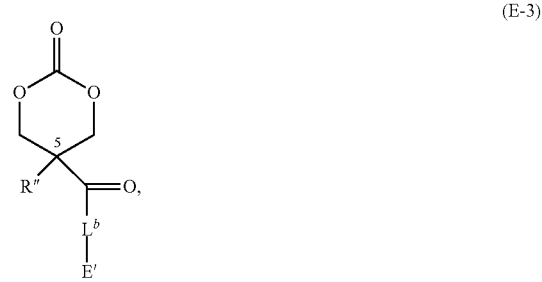

(E-3)

wherein ring atom 5 is labeled, $L^b$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, R" is a monovalent radical selected from the group consisting of hydrogen, halogens, and alkyl groups comprising 1 to 6 carbons.

Ring opening polymerization of cation-forming monomers of formula (E-3) produces a polycarbonate having a repeat unit according to formula (E-4):

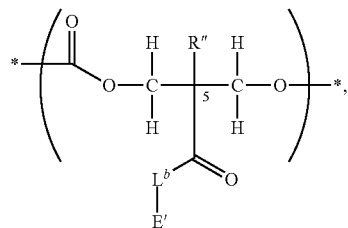

(E-4)

wherein backbone atom 5 is labeled, $L^b$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, R" is a monovalent radical selected from the group consisting of hydrogen, halogens, and alkyl groups comprising 1 to 6 carbons.

Other more specific E-monomers have the formula (E-5):

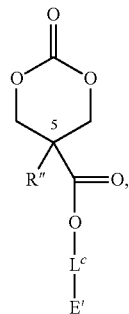

(E-5)

wherein ring atom 5 is labeled, $L^c$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, R" is a monovalent radical selected from the group consisting of hydrogen, halogens, and alkyl groups comprising 1 to 6 carbons.

Ring opening polymerization of cation-forming monomers of formula (E-5) produces a polycarbonate having a repeat unit according to formula (E-6):

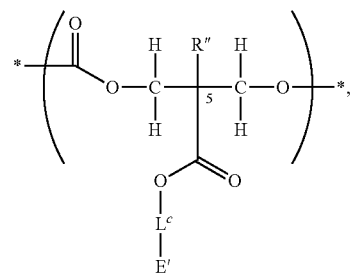

(E-6)

wherein backbone atom 5 is labeled, $L^c$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, R" is a monovalent radical selected from the group consisting of hydrogen, halogens, and alkyl groups comprising 1 to 6 carbons.

The E-monomers can have the formula (E-7):

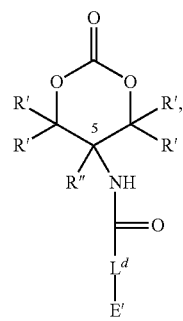

(E-7)

wherein ring atom 5 is labeled, $L^d$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, each R' is an independent monovalent radical selected from the group consisting of hydrogen, halogens, methyl, and ethyl, and R" is a monovalent radical selected from the group consisting of hydrogen, halogens, and alkyl groups comprising 1 to 6 carbons.

Ring opening polymerization of E-monomers of formula (E-7) produces an initial polycarbonate having an electrophilic repeat unit according to formula (E-8):

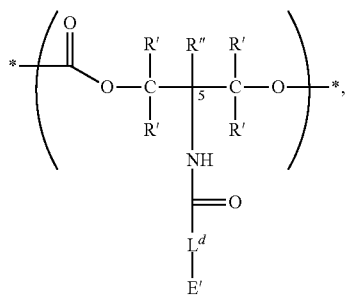

(E-8)

wherein
backbone atom 5 is labeled,
$L^d$ is a divalent linking group comprising at least 2 carbons,
E' is an electrophilic group capable of reacting with a nucleophile to form a moiety comprising a member of the group consisting of quaternary amine groups, quaternary phosphonium groups, and catechol groups,
each R' is an independent monovalent radical selected from the group consisting of hydrogen, halogens, methyl, and ethyl, and
R" is a monovalent radical selected from the group consisting of hydrogen, halogens, and alkyl groups comprising 1 to 6 carbons.

It will be apparent to those skilled in the art that linking groups $L^a$, $L^b$, $L^c$, and $L^d$ can be one or more of the above-described linking groups for the catechol repeat units and cationic repeat units.

E' groups include leaving groups (e.g., chloride, bromide, iodide, sulfonate ester, and the like), which are capable of undergoing a nucleophilic displacement reaction with a Lewis base (e.g., dopamine, tertiary amine, trialkyl phosphine) to form a moiety comprising a catechol group, a quaternary ammonium group and/or a phosphonium group. In an embodiment, E' is chloride, bromide, and/or iodide. In another embodiment, the cyclic carbonate monomer is a compound of formula (E-1) and the initial polycarbonate comprises an electrophilic repeat unit of formula (E-2). In another embodiment, the cyclic carbonate monomer is a compound of formula (E-5) and the initial polycarbonate comprises an electrophilic repeat unit of formula (E-6).

Other E' groups include active esters such as, for example, pentafluorophenyl esters, p-nitrophenyl esters, pentachlorophenyl esters, which can undergo displacement by a primary amine or an alcohol to form an amide or an ester, respectively.

Exemplary E-monomers include the cyclic carbonate monomers of Table 1. A particularly preferred E-monomer is MTC-BnCl.

TABLE 1

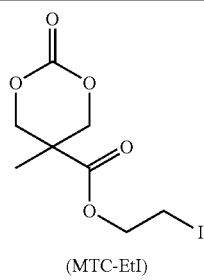

(MTC-EtI)

TABLE 1-continued

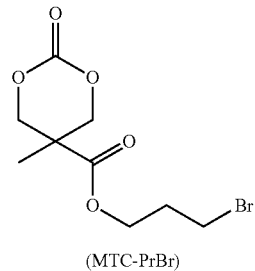

(MTC-PrBr)

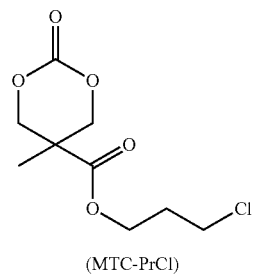

(MTC-PrCl)

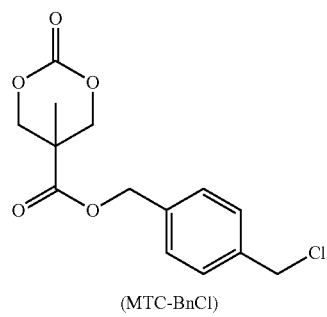

(MTC-BnCl)

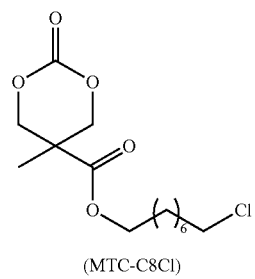

(MTC-C8Cl)

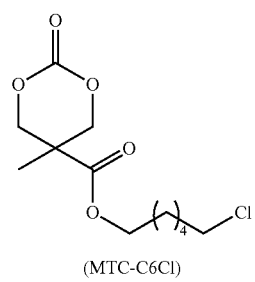

(MTC-C6Cl)

TABLE 1-continued

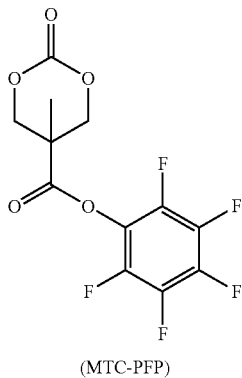

(MTC-PFP)

Oligomeric PEG Monomers

Cyclic carbonate monomers bearing a PEG substituent are known in the art, and can be prepared according to the reaction illustrated in Example 2 further below. The PEG starting material used in the reaction can have a number average molecular weight (Mn) of about 200 to about 5000, preferably about 200 to about 1500, and a DP of about 5 to about 30 in ethylene oxide units.

Mononucleophilic Initiators for One-Armed Catechol Polymers

Nucleophilic initiators for ROP generally include alcohols, amines, and/or thiols.

ROP initiators capable of forming ring opened polymers having one polymer chain (one-armed ROP polymers) are mono-nucleophilic initiators (e.g., ethanol, n-butanol, benzyl alcohol, and the like). Herein, a mono-nucleophilic initiator can include more than one nucleophilic group (e.g., thioethanol), but only one nucleophilic group of the initiator initiates the ROP under the conditions used to perform the polymerization.

ROP initiators capable of forming ring opened polymers having two polymer chains (two-armed ROP polymers) are di-nucleophilic initiators. Herein, a di-nucleophilic initiator can include more than two nucleophilic groups (e.g., 2-mercapto-1,3-propanediol), but only two nucleophilic groups of the initiator initiate the ROP under the conditions used to perform the polymerization. Exemplary di-nucleophilic ROP initiators include ethylene glycol, butanediol, 1,4-benzenedimethanol, and Bn-MPA:

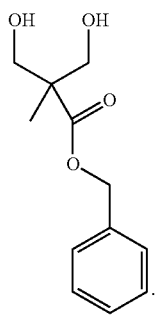 [SMILES: CC(CO)(CO)C(=O)OCc1ccccc1]

Preferably, the ROP initiator used in the formation of the disclosed catechol polymers comprises one or two primary alcohol groups for initiating ROP.

The ROP initiator can be used singularly or in combination with a different ROP initiator. The ROP initiator can be stereospecific or non-stereospecific.

ROP Polymerization

Using a cyclic carbonate monomer of formula (E-1) to illustrate a method of making the disclosed catechol polymers, a reaction mixture is formed which comprises a cyclic carbonate monomer of formula (E-1), a catalyst, an optional accelerator, a mono-nucleophilic ROP initiator (optionally comprising a thiol group that does not participate in the ROP), and a solvent. Agitating the reaction mixture forms an initial polycarbonate.

Optionally, the initial polycarbonate can be endcapped to form an endcapped initial polycarbonate. The resulting polymer has a structure according to formula (F-1):

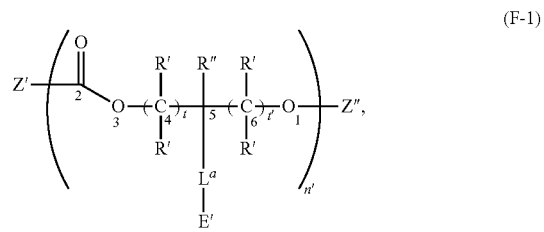

wherein n' represents the number of electrophilic repeat units, wherein n' has a value greater than or equal to 1, Z' is a monovalent first end group comprising 1 or more carbons and a heteroatom selected from the group consisting of N, O, and S, wherein the heteroatom is linked to a backbone carbonyl group of the initial polymer, Z" is a monovalent second end group selected from the group consisting of hydrogen and groups comprising 1 or more carbons, $L^a$ is a divalent linking group comprising at least 1 carbon, E' is an electrophilic group capable of reacting with a nucleophile to form a moiety comprising a member of the group consisting of quaternary amine groups, quaternary phosphonium groups, and catechol groups, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, and no electrophilic repeat unit has t=0 and t'=0.

In this instance, each repeat unit of the initial polycarbonate is an electrophilic repeat unit comprising a side chain E' group.

Z' can be a residue of the ROP initiator. In an embodiment, Z' is an oxy residue of the mono-alcohol initiator comprising 1 to 15 carbons.

The living end (oxy end) of the initial polymer formed by the ROP has a reactive hydroxy group (second end group Z"=H), which is capable of initiating another ROP. The living end can be treated with an endcap agent, thereby forming a second end group (Z" contains at least one carbon), which is capable of preventing further chain growth and stabilizing the polymer against unwanted side reactions such as chain scission. The polymerization and endcapping can occur in the same pot without isolating the initial polymer. Endcap agents include, for example, materials for converting terminal hydroxy groups to esters, such as carboxylic acid anhydrides, carboxylic acid chlorides, and reactive esters (e.g., p-nitrophenyl esters). In an embodiment, the endcap agent is an acylating agent, and the second end group Z" is an acyl group. In another embodiment the acylating agent is acetic anhydride, and the second end group Z" is an acetyl group.

The initial polycarbonate and/or the endcapped initial polycarbonate can be treated with a nucleophilic form of a catechol (e.g., dopamine) to convert E' to a moiety comprising a catechol group. Subsequently, any remaining E' groups of the initial polycarbonate can be treated with a tertiary amine and/or a tertiary phosphine to form cationic repeat units comprising a positive-charged $Q'(R^a)_{u''}$ group.

Exemplary non-limiting tertiary amines for forming quaternary amines by a nucleophilic substitution reaction with electrophilic E' groups include trimethylamine, triethylamine, tri-n-propylamine, tri-iso-propylamine, tri-n-butylamine, tri-n-pentylamine, dimethylethylamine, dimethylpropylamine, dimethyl-iso-propylamine, dimethylbutylamine, dimethylpentylamine, dimethylbenzylamine, diethylmethylamine, diethylpentylamine, diethylbutylamine, N,N-dimethylcyclohexylamine, N-methylimidazole, N-ethylimidazole, N-(n-propyl)imidazole, N-isopropylimidazole, N-(n-butyl) imidazole, N,N-diethylcyclohexylamine, N,N-dimethylaniline, N,N-diethylaniline, pyridine, and combinations thereof.

Exemplary non-limiting tertiary phosphines for forming quaternary phosphonium groups by a nucleophilic substitution reaction with electrophilic E' groups include trimethylphosphine, triethylphosphine, tripropylphosphine, tributylphosphine, ethyldimethylphosphine, propyldimethylphosphine, butyldimethylphosphine, pentyldimethylphosphine, hexyldimethylphosphine, heptyldimethylphosphine, octyldimethylphosphine, methyldiethylphosphine, propyldiethylphosphine, butyldiethylphosphine, pentyldiethylphosphine, hexyldiethylphosphine, heptyldiethylphosphine, octyldiethylphosphine, pentyldipropylphosphine, pentyldibutylphosphine, dipentylmethylphosphine, dipentylethylphosphine, dipentylpropylphosphine, dipentylbutylphosphine, tripentylphosphine, hexyldipropylphosphine, hexyldibutylphosphine, cyclohexyl-dimethylphosphine, cyclohexyldiethylphosphine, dihexylmethylphosphine, dihexyl-ethylphosphine, dihexylpropylphosphine, benzyldimethylphosphine, and combinations thereof The ring-opening polymerization can be performed at a temperature that is about ambient temperature or higher, more specifically 15° C. to 200° C., and even more specifically 20° C. to 80° C. Preferably, the ROP is performed at ambient temperature. Reaction times vary with solvent, temperature, agitation rate, pressure, and equipment, but in general the polymerizations are complete within 1 to 100 hours.

The ROP reaction is preferably performed with a solvent. Non-limiting solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerization is conducted under an inert dry atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

Preferably, the chemical formula of the catalyst used for the ring opening polymerization does not include an ionic or nonionic form of a metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferred catalysts are organocatalysts whose chemical formulas contain none of the above metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

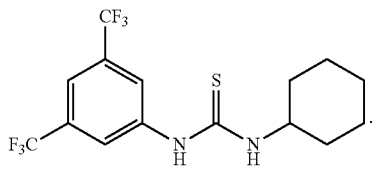

Other ROP organocatalysts comprise at least one 1,1,1,3,3,3-hexafluoropropan-2-ol-2-yl (HFP) group. Singly-donating hydrogen bond catalysts have the formula (G-1):

 (G-1), wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 2.

TABLE 2

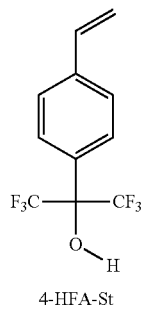 [SMILES: C=Cc1ccc(C(O)(C(F)(F)F)C(F)(F)F)cc1]

4-HFA-St

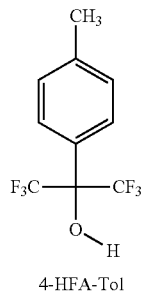 [SMILES: Cc1ccc(C(O)(C(F)(F)F)C(F)(F)F)cc1]

4-HFA-Tol

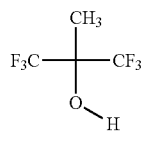

HFTB

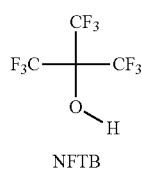

NFTB

TABLE 2-continued

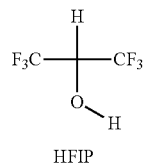

HFIP

Doubly-donating hydrogen bonding catalysts have two HFP groups, represented by the formula (20):

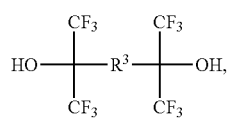 (G-2)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (G-2) include those listed in Table 3. In a specific embodiment, $R^2$ is an arylene or substituted arylene group, and the HFP groups occupy positions meta to each other on the aromatic ring.

TABLE 3

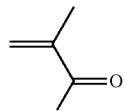

3,5-HFA-MA

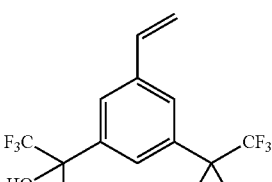

3,5-HFA-St

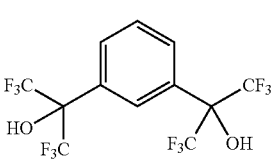

1,3-HFAB

TABLE 3-continued

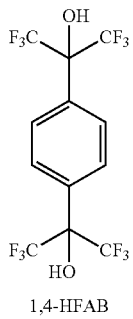

1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (–)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl)imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 4.

TABLE 4

Pyridine
(Py)

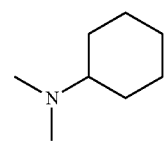

N,N-Dimethylaminocyclohexane
(Me$_2$NCy)

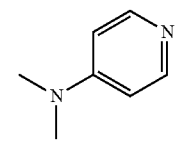

4-N,N-Dimethylaminopyridine
(DMAP)

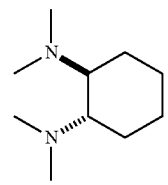

trans 1,2-Bis(dimethylamino)cyclohexane
(TMCHD)

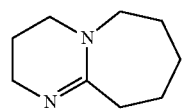

1,8-Diazabicyclo[5.4.0]undec-7-ene
(DBU)

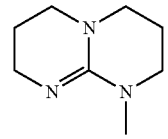

7-Methyl-1,5,7-triazabicyclo[4.4.0]dec-5-ene
(MTBD)

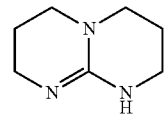

1,5,7-Triazabicyclo[4.4.0]dec-5-ene
(TBD)

TABLE 4-continued

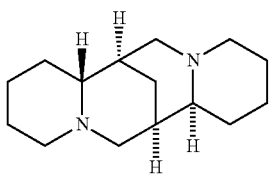

(−)-Sparteine
(Sp)

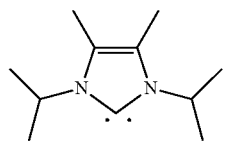

1,3-Bis(2-propyl)-4,5-dimethylimidazol-2-ylidene
(Im-1)

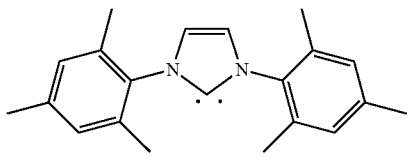

1,3-Bis(2,4,6-trimethylphenyl)imidazol-2-ylidene
(Im-2)

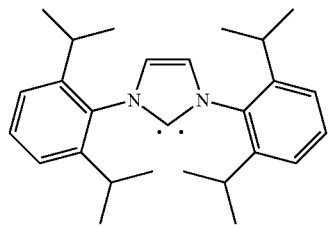

1,3-Bis(2,6-di-i-propylphenyl)imidazol-2-ylidene
(Im-3)

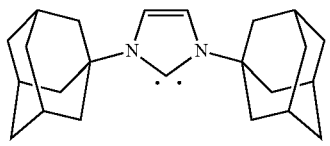

1,3-Bis(1-adamantyl)imidazol-2-yliden)
(Im-4)

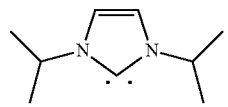

1,3-Di-i-propylimidazol-2-ylidene
(Im-5)

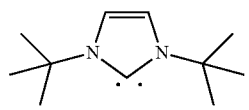

1,3-Di-t-butylimidazol-2-ylidene
(Im-6)

TABLE 4-continued

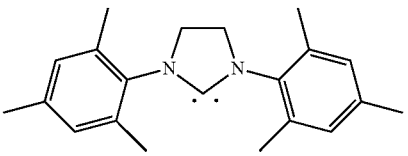

1,3-Bis(2,4,6-trimethylphenyl)-4,5-
dihydroimidazol-2-ylidene
(Im-7)

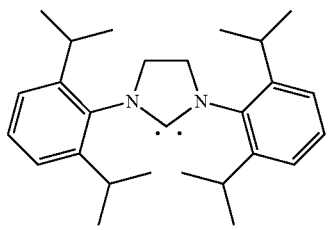

1,3-Bis(2,6-di-i-propylphenyl)-4,5-
dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The initiator groups are preferably present in an amount of 0.001 to 10.0 mol %, 0.1 to 2.5 mol %, 0.1 to 1.0 mol %, or 0.2 to 0.5 mol %, based on total moles of cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on total moles of cyclic carbonate monomer.

The catalysts can be removed by selective precipitation or, in the case of the solid supported catalysts, by filtration. The catalyst can be present in an amount of 0 wt % (weight percent) to about 20 wt %, preferably 0 wt % (weight percent) to about 0.5 wt % based on the total weight of the cationic polymer and the residual catalyst. The cationic polymer preferably comprises no residual catalyst.

Average Molecular Weight.

The catechol polymers preferably have a number average molecular weight (Mn) as determined by size exclusion chromatography of about 1500 to about 50,000, more specifically about 1500 to about 30,000. The initial polycarbonate precursor to the catechol polymer preferably has a polydispersity index (PDI) of 1.01 to about 1.5, more particularly 1.01 to 1.30, and even more particularly 1.01 to 1.25.

The catechol polymer is preferably formed by an organo-catalyzed ring opening polymerization. The ring opening polymerization is preferably initiated by an monol and or a diol.

In some instances the catechol polymers can self-assemble into nanoparticulate micelles in de-ionized water. The catechol polymers can have a critical micelle concentration (CMC) of about 15 mg/L to about 250 mg/L.

Catechol Polymer Films

An initial film layer comprising a catechol polymer disposed on a surface of substrate can be prepared by contacting the surface with a solution containing the catechol polymer and a suitable solvent, preferably water. The solution can be applied to the surface using well known coating techniques that include but are not limited to dip coating, spray coating, and the like. Removal of the solvent from the initial film layer results in a treated substrate comprising a surface film of the catechol polymer disposed on the substrate surface. The surface film can comprise a polymerized form of the pendant catechol group, a quinone derivative thereof, polymeric derivatives thereof, and combinations of any of the foregoing. After drying, the films can be colored (e.g., brown), can adhere strongly to the substrate surface, and can be highly resistant to solvent stripping. The high antimicrobial and antifouling activity of the films, coupled with red blood cell compatibility of the films makes these catechol polymers highly attractive for medical applications, such as forming antimicrobial and antifouling films on silicone rubber catheters.

The substrate surface can be treated with one or more applications of catechol polymer. Contacting a given substrate with a solution containing a catechol polymer and a suitable solvent (e.g., by dip coating or spray coating) produces an initial film layer comprising the catechol polymer and the solvent disposed on the substrate surface. Removing the solvent from the initial film layer produces a treated substrate comprising a catechol layer disposed on the substrate surface. A catechol layer comprising two or more layers of catechol polymer is referred to herein as a composite catechol layer. Multiple layers of catechol polymer can be applied in a separate steps (e.g., separate immersion steps) to obtain a desired level of performance and/or thickness of the composite catechol layer. The composite catechol layers can have enhanced antimicrobial and/or antifouling properties. The catechol layers can comprise the same or different catechol polymer(s).

Substrates can include metals (e.g., titanium), metal alloys (e.g., stainless steel), metal oxides, silicon oxides, semiconductors, ceramics, polymers, silicones and combinations thereof. Exemplary polymer substrates include but are not limited to polystyrenes, polyethylenes, polycarbonates, poly (ethylene terephthalate), polyetheretherketones, polyurethanes, and combinations thereof.

Herein, silicone rubber materials are polymers consisting essentially of silicon, carbon, oxygen, and hydrogen. Each tetravalent silicon atom can be linked to $m=1$ to 4 oxygens and/or to $n=0$ to 3 carbons, wherein $m+n=4$. Thus, a silicone rubber can have a polymer backbone comprising subunits selected from the group consisting of $Si(R)_3(O-*)_1$, $Si(R)_2(O-*)_2$, $Si(R')(O-*)_3$, $Si(O-*)_4$, and combinations thereof, wherein each R' is an independent monovalent radical comprising at least one carbon, and the starred bonds represent attachment points to other subunits of the silicone rubber. In an embodiment, each R' is methyl. The silicone rubber materials can be crosslinked and/or branched polymers. In an embodiment, the silicone rubber material is a medical grade silicone rubber.

FIG. 1 is a series of cross-sectional layer diagrams illustrating an exemplary process of forming a treated substrate (e.g., a substrate comprising silicone rubber) comprising one or two catechol layers. Substrate 10, which comprises a surface 12 and core 14 of thickness t', is contacted with a first solution comprising a first catechol polymer dispersed in a first solvent. Contacting substrate 10 with the first solution can comprise, for example, immersing substrate 10 in the first solution for a period of time and at a temperature effective in forming an initial film layer (not shown) comprising the first catechol polymer and first solvent disposed on surface 12. Removal of the first solvent from the initial film layer results in first treated substrate 20, which comprises first catechol layer 22 of thickness w' and core 14 of thickness t". The catechol groups of the catechol polymer can be present in the first catechol layer 22 as catechol groups, quinone derivatives of the catechol groups, polymeric derivatives of the foregoing groups, or combinations of the foregoing. That is, first catechol layer 22 can be in the form of a self-crosslinked film layer derived from partial or exhaustive self-polymerization and/or oxidation of the catechol groups of the catechol polymer. The first catechol layer 22 can be bound to the substrate surface covalently and/or non-covalently. The foregoing process can be performed two or more times to form a composite catechol layer. FIG. 1 illustrates an optional second application of catechol polymer on first treated substrate 20. First treated substrate 20 is contacted (e.g., by immersion coating) with a second solution comprising a second catechol polymer dispersed in a second solvent, thereby forming a second initial film layer (not shown), which comprises the second cationic polymer and the second solvent disposed on the first catechol layer 22. Removing the second solvent results in second catechol layer 32 of thickness v' comprising the second catechol polymer disposed on the first catechol layer 22, having thickness w'. Second catechol layer 32 can be a self-crosslinked film derived from partial or exhaustive self-polymerization and or oxidation of the catechol groups of the second catechol polymer. Second catechol layer 32 can be covalently or non-covalently bound to first catechol layer 22. That is, the catechol groups of second catechol layer 32 can react with catechol groups of first catechol layer 22 to form a covalent linkages joining the layers. The thicknesses of first catechol layer 22, second catechol layer 32, and core 14 as drawn are for clarity purposes, and not meant to depict relative scale. No restriction is placed on the thicknesses of the first catechol layer 22, second catechol layer 32 and core 14.

First catechol layer 22 and second catechol layer 32 are not necessarily sharply bounded layers. That is, intermixing can occur between first catechol layer 22, second catechol layer 32, and/or core 14. Thus, the first catechol polymer and/or the second catechol polymer can potentially be in contact with and/or bound to core 14. The total thickness (i.e., v'+w') of the first catechol layer 22 and second catechol layer 32 can be about 2 nanometers to about 10 micrometers. In an embodiment the total thickness of the first catechol layer 22 and second catechol layer 32 is about 5 nm to about 10 nm.

Figure 2:
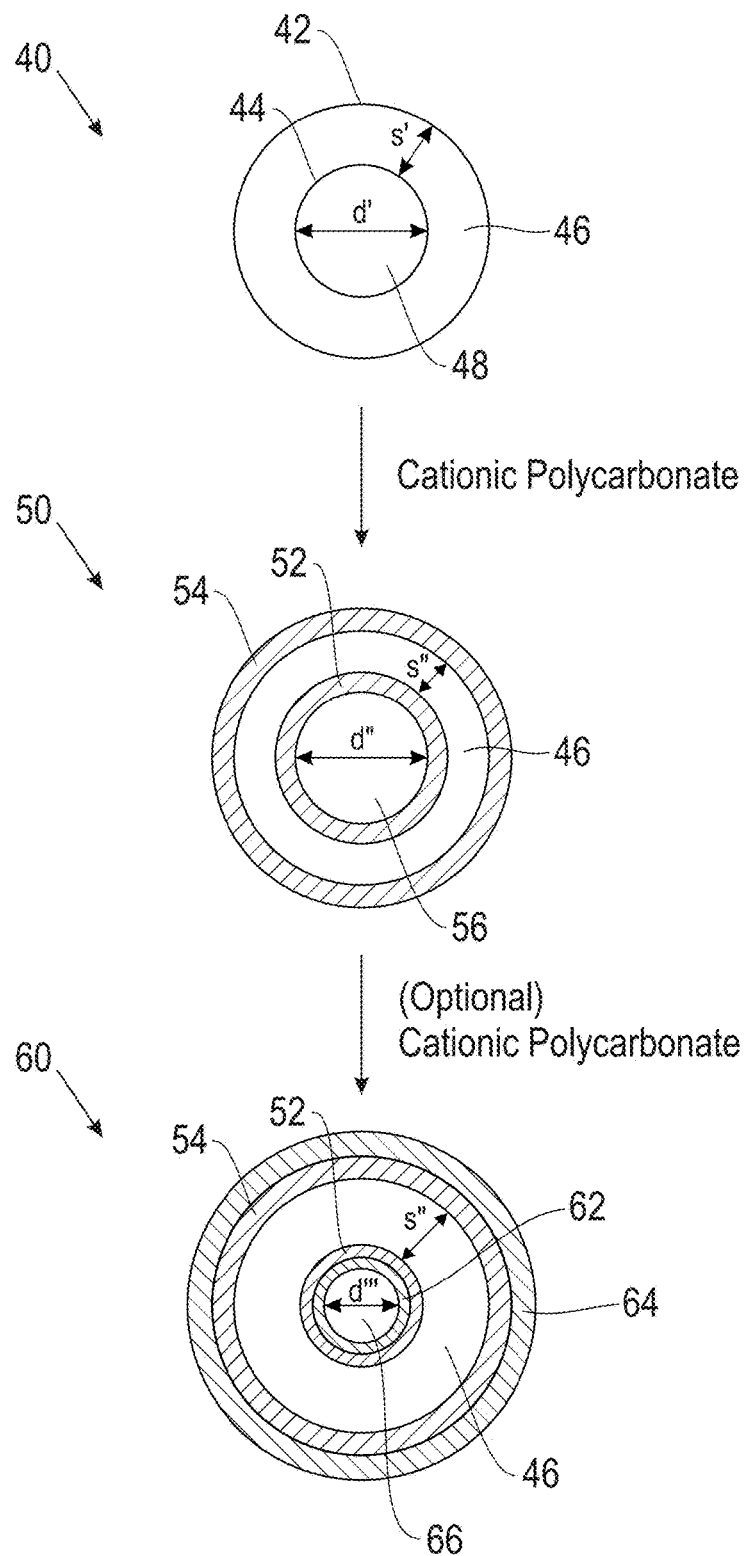
FIG. 2 is a series of cross-sectional layer diagrams illustrating a process of forming an antimicrobial silicone rubber tubing.

FIG. 2 illustrates the above-described process using a substrate in the form of tubing 40 (e.g., silicone rubber tubing). Tubing 40 comprises outer surface 42, inner surface 44, core 46 of thickness s', and spatial region 48 having a diameter d'. Tubing 40 is treated with a first solution comprising a first catechol polymer dispersed in a first solvent (e.g., by immersion coating), thereby forming an initial film layer (not shown) disposed on outer surface 42 and inner surface 44 of tubing 40. Removing the first solvent from the initial film layer results in a first treated tubing 50 comprising a inner first catechol layer 52 of thickness r' (not shown), outer first catechol layer 54 of thickness r" (not shown), core 46 of thickness s", and spatial region 56 having inner diameter d". The foregoing process can be performed one or more times. FIG. 2 illustrates a second application of catechol polymer on first treated tubing 50. First treated tubing 50 is contacted (e.g., by immersion coating) with a second solution comprising a second catechol polymer dispersed a second solvent, thereby forming a second initial film layer (not shown) disposed on inner first catechol layer 52 and outer first catechol layer 54 of first treated tubing 50. Removing the second solvent results in second tubing 60 comprising an inner second catechol layer 62 of thickness q' (not shown), outer second catechol layer 64 of thickness q" (not shown), inner first catechol layer 52 of thickness r' (not shown), outer first catechol layer 54 of thickness r" (not shown), core 46 of thickness s", and spatial region 66 having inner diameter d'". The thickness of the inner and outer catechol layers of first treated tubing 50 and second treated tubing 60 relative to core 46 are drawn for clarity purposes and are not to scale. The total thickness of the inner catechol layers (i.e., r'+q') and outer catechol layers (i.e., r"+q") can have a value of about 2 nanometers to about 10 micrometers. In an embodiment, the value r'+q' equals about 5 nm to about 10 nm and r"+q" is about 5 nm to about 10 nm.

Intermixing can occur between outer first catechol layer 54, outer second catechol layer 64, and/or core 46 can occur. Intermixing can occur between inner first catechol layer 54, inner second catechol layer 64, and/or core 46.

The catechol layers can be effective antimicrobial agents against a variety of microbes. Non-limiting microbes include Gram-positive *Staphylococcus epidermidis* (*S. epidermidis*), Gram-positive *Staphylococcus aureus* (*S. aureus*), Gram-negative *Escherichia coli* (*E. coli*), Gram-negative *Pseudomonas aeruginosa* (*P. aeruginosa*), Gram-positive fungus *Candida albicans* (*C. albicans*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), Gram-positive yeast *Cryptococcus neoformans* (*C. neoformans*), and Gram-negative *Klebsiella pneumoniae* (*K. pneumoniae*).

The following examples illustrate the formation of catechol polymers and an antimicrobial and antifouling films of these materials on silicone rubber.

EXAMPLES

Materials used in the following examples are listed in Table 5.

TABLE 5

| ABBREVIATION | DESCRIPTION | SUPPLIER |
| --- | --- | --- |
| DBU | 1,8-Diazabicyclo[5,4,0]undec-7-ene | Sigma-Aldrich |
| 4-CMBA | p-Chloromethyl Benzyl Alcohol | Sigma-Aldrich |
| TMA | Trimethylamine | Sigma-Aldrich |
| DCM | Dichloromethane | Sigma-Aldrich |
| TU | N-Bis(3,5-Trifluoromethyl)Phenyl-N'-Cyclohexylthiourea | Prepared as described below |

TABLE 5-continued

| ABBREVIATION | DESCRIPTION | SUPPLIER |
| --- | --- | --- |
| BnOH | Benzyl Alcohol, initiator for ROP | Sigma-Aldrich |
| 4-MBA | 4-Methyl Benzyl Alcohol, initiator for ROP | Sigma-Aldrich |
| MPEG-5k | Monomethyl Endcapped Poly(ethylene glycol); Mn 5000 g/mol, DP 117, PDI 1.03 | Polymer Source Inc., Canada |
| MPEG-1k | Monomethyl Endcapped Poly(ethylene glycol); Mn 750 g/mol, DP 17, PDI 1.03 | Polymer Source Inc., Canada |
| PBS | Phosphate Buffered Saline | 1st BASE |
| DMBA | Dimethylbenzylamine | Sigma-Aldrich |
| BSA | Bovine Serum Albumen | Sigma-Aldrich |

Herein, Mn is the number average molecular weight, Mw is the weight average molecular weight, and MW is the molecular weight of one molecule.

$CH_3O$-PEG-OH (also called MPEG-5k, Mn 5000 g/mol, PDI 1.03) was purchased from Polymer Source Inc., Canada. MPEG-5k was dried by azeotropic distillation using toluene and dried in vacuo prior to use. 1,8-Diazabicyclo[5,4,0]undec-7-ene (DBU) was stirred over $CaH_2$ and vacuum distilled before being transferred to a glove-box. All other chemical reagents such as dopamine hydrochloride and bovine serum albumin (BSA) were bought from Sigma-Aldrich and used as received unless otherwise mentioned. Silicone kit SYLGARD 184 was purchased from Dow Corning and used according to the suggested protocols. A LIVE/DEAD BacLight™ bacterial viability kit (L-7012) was purchased from Invitrogen. A commercial strain of *S. aureus* (ATCC No. 6538) and *E. coli* (ATCC No. 25922) was bought from ATCC (U.S.A). A silicone catheter was provided by Dr. Li Yang Hsu from National University Hospitals of Singapore.

N-bis(3,5-trifluoromethyl)phenyl-N'-cyclohexylthiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

Neutralization of Dopamine HCl

Dopamine.HCl (1.9 g, 0.01 mol) was dissolved in 10 mL of DI water and cooled down to 4° C., and 10 mL of 1 M cold NaOH solution was then added dropwise to the solution under stirring. The reaction solution was stirred for another 10 minutes before it was freeze-dried. The resulting solid was dissolved in 50 mL of MeOH, filtered, and the filtrate was concentrated to dryness and dried in vacuo, giving a light brown powder. $^1$H NMR (400 MHz, $D_2O$, 22° C.): delta 6.63 (d, 1H, PhH), 6.56 (d, 1H, PhH), 6.43 (d, 1H, PhH), 3.02 (t, 3H, -$PhCH_2$—), 2.66 (t, 3H, —$CH_2NH_2$).

Monomer Synthesis

The preparation of cyclic carbonates MTC-OH and MTC-Cl from 2,2-bis(methylol)propionic acid (bis-MPA) used in this study can be found in R. C. Pratt, et al., Chemical Communications, 2008, 114-116, shown in Scheme 1.

Scheme I.

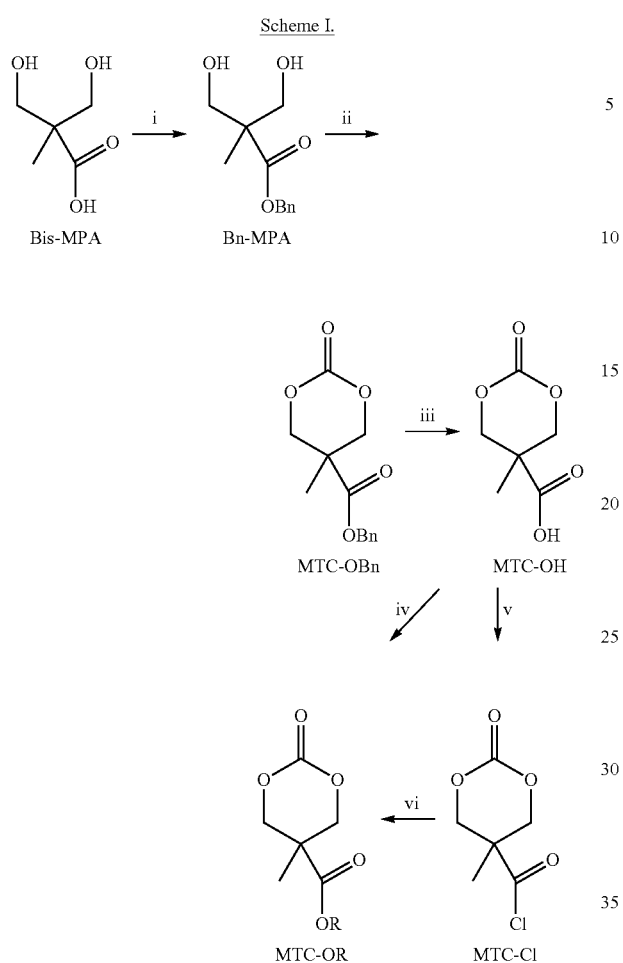

This approach has been demonstrated to create a wide selection of functional monomers capable of undergoing ring-opening polymerization. 2,2-Bis(methylol)propionic acid (bis-MPA) is first converted (i) to a benzyl ester Bn-MPA, followed by reaction (ii) of Bn-MPA with triphosgene to form a cyclic carbonyl monomer, MTC-OBn. MTC-OBn is debenzylated (iii) to produce the cyclic carbonyl carboxylic acid, MTC-OH. Two pathways are shown for forming an ester from MTC-OH. In the first pathway, (iv), MTC-OH is treated with a suitable carboxy activating agent, such as dicyclohexylcarbodiimide (DCC), which reacts with ROH to form MTC-OR in a single step. Alternatively, MTC-OH can be converted first (v) to the acid chloride MTC-Cl followed by treatment (vi) of MTC-Cl with ROH in the presence of a base to form MTC-OR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bis-MPA; (ii) triphosgene, pyridine, $CH_2Cl_2$, −78° C. to 0° C., 95% yield of MTC-OBn; (iii) Pd/C (10%), $H_2$ (3 atm), EtOAc, room temperature, 24 hours, 99% yield of MTC-OH; (iv) ROH, DCC, THF, room temperature, 1 to 24 hours; (v) $(COCl)_2$, THF, room temperature, 1 hour, 99% yield of MTC-Cl; (vi) ROH, $NEt_3$, RT, 3 hours yields MTC-OR.

Example 1

Synthesis of MTC-BnCl

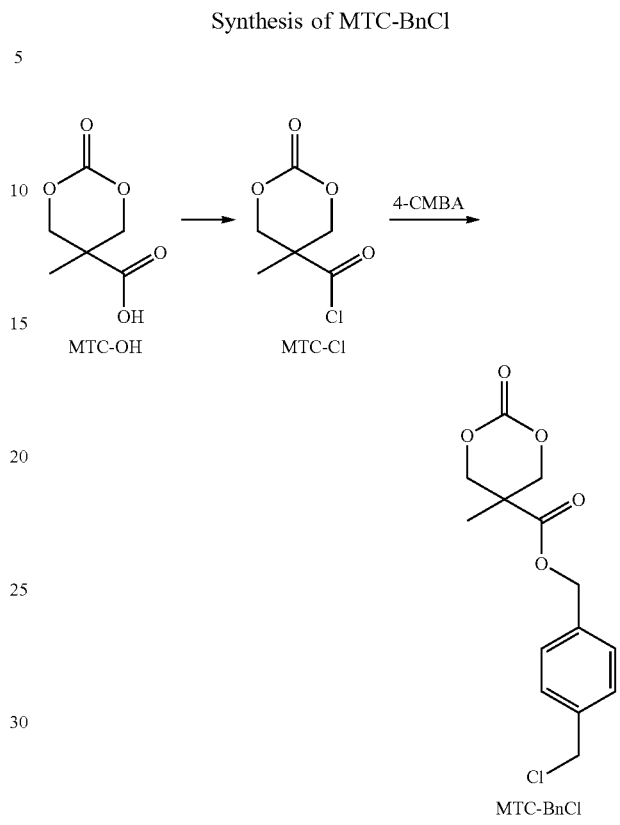

The synthesis of MTC-BnCl was performed in two steps as follows.

A) Preparation of MTC-Cl. Into a dry THF solution (100 mL) of MTC-OH (4.8 g, 30 mmol), a solution of oxalyl chloride (3.8 mL, 45 mmol) in dry THF (50 mL) was gently added over 20 minutes under nitrogen atmosphere after a catalytic amount (3 drops) of DMF was added. After the solution was stirred for 1 hour, it was bubbled with a nitrogen flow to remove volatiles, and was then evaporated under vacuum.

B) Preparation of MTC-BnCl. A mixture of 4-(chloromethyl)benzyl alcohol (4-CMBA, 4.35 g, 28 mmol) and pyridine (2.4 mL, 30 mmol) in dry tetrahydrofuran (THF, 50 mL) was added drop-wise to a dry THF solution (100 mL) of the above-prepared intermediate MTC-Cl over 30 minutes at 0° C. with ice bath. The reaction mixture was stirred 30 minutes, after which the ice bath was removed. The reaction mixture was stirred for 3 hours at room temperature. Dichloromethane (DCM) was then added and the solution was transferred to a separation funnel, washed with brine 3 times and dried over $MgSO_4$ overnight. The resulting reaction solution was filtered and concentrated to dryness. The crude product was purified by a silica gel column, eluting using a gradient mixture of ethyl acetate/hexane from 50/50 to 80/20 by volume to provide the product MTC-BnCl as a colorless oil that slowly solidified to a white solid (6.7 g, 80%). $^1$H NMR (400 MHz, $CDCl_3$, 22° C.): delta 7.36 (dd, 4H, PhH), 5.21 (s, 2H, —$OCH_2$Ph-), 4.69 (d, 2H, —$CH_2OCOO$—), 4.58 (s, 2H, -$PhCH_2Cl$), 4.20 (d, 2H, —$CH_2OCOO$—), 1.32 (s, 3H, —$CH_3$).

Example 2

Synthesis of MTC-PEG

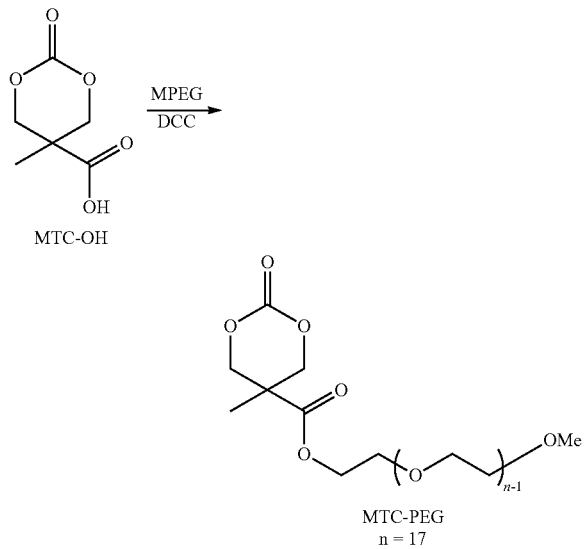

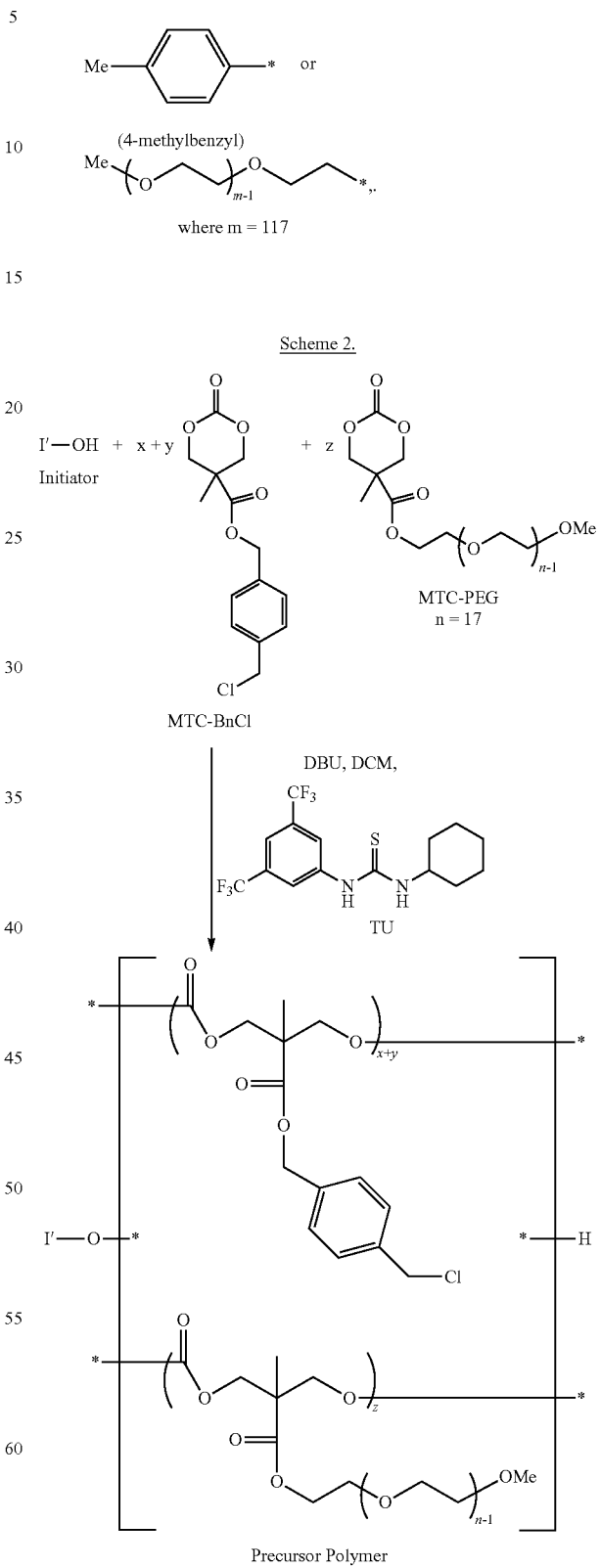

Oligomeric monomethoxy poly(ethylene glycol) (MPEG-1k, 4.5 g, Mn=750, PDI 1.03, 6 mmol) was charged in a 250 mL three-neck round bottom flask and heated to 82° C. in vacuo with stirring overnight and cooled to room temperature. A solution of MTC-OH (1.44 g, 9 mmol) in dry THF (50 mL) was added to the MPEG under nitrogen atmosphere, followed by gently adding a solution of dicyclohexylcarbodiimide (DCC) (2.48 g, 12 mmol) in dry THF (50 mL). The reaction solution was stirred for 48 hours, filtered, and concentrated to dryness. The resulting crude product was purified by column chromatography on a SEPHADEX LH-20 column with THF as eluent, giving pure MTC-PEG as a white viscous solid (4.6 g, 83%). $^1$H NMR (400 MHz, CDCl$_3$, 22° C.): delta 4.45 (dd, 4H, —CH$_2$OCOO—), 4.35 (d, 2H, —COOCH$_2$-MPEG), 3.65 (s, 68H, H of MPEG), 1.34 (s, 3H, —CH$_3$).

Polymer Characterization

Gel Permeation Chromatography (GPC)

GPC analysis of block copolymers was carried out with a Waters HPLC system equipped with a 2690D separation module, two Styragel HR1 and HR4E (THF) 5 micrometer columns (size: 300×7.8 mm) in series and a Waters 410 differential refractometer detector. The mobile phase used was THF with a flow rate of 1 mL/min. Number average molecular weights as well as polydispersity indices were calculated from a calibration curve using a series of polystyrene standards with molecular weight ranging from 1350 to 151700.

$^1$H NMR Analysis $^1$H NMR spectra of monomers and polymers were recorded on a Bruker Advance 400 NMR spectrometer at 400 MHz at room temperature. The $^1$H NMR measurements were carried out with an acquisition time of 3.2 seconds, a pulse repetition time of 2.0 seconds, a 30° pulse width, 5208-Hz spectral width, and 32 K data points. Chemical shifts were referred to the solvent peaks (delta=7.26 and 2.50 ppm for CDCl$_3$ and DMSO-d$_6$, respectively).

Polymer Synthesis

Precursor polymers (i.e., initial polycarbonates) for the catechol-containing cationic polymers were made according to Scheme 2 below, where I'—OH is 4-methylbenzyl alcohol or mono-methyl poly(ethylene glycol), MPEG-5k, Mn 5000, DP=117, and I' is The preparation of precursor polymers P-1 and P-2 are representative.

Example 3

The preparation of precursor polymer P-1, poly(MTC-BnCl), for theoretical degree of polymerization (DP) of 80. In a glovebox, 4-methylbenzyl alcohol (4-MBA, 2.24 mg, 0.018 mmol, initiator) and MTC-BnCl (0.43 g, 1.44 mmol, monomer) were added to the solution of TU (6 mg, 0.016 mmol, co-catalyst) in 1 mL of DCM, followed by adding DBU (2.4 microliters, 0.016 mmol, catalyst) to initiate the polymerization. The reaction mixture was stirred 20 minutes, followed by addition of a solution of TU (20.7 mg, 0.056 mmol) and DBU (8.4 microliters, 0.056 mmol) in 1 mL of DCM. The reaction mixture was stirred for another 1 hour before benzoic acid (about 10 mg) was added to quench the polymerization. Finally, the reaction solution was precipitated in cold MeOH, centrifuged and washed with cold MeOH twice. The resulting product was dried in vacuo, giving poly(MTC-BnCl), P-1, as a white viscous solid (0.40 g, 93%). PDI: 1.20. $^1$H NMR (400 MHz, CDCl3, 22° C.): delta 7.29 (m, 212H, PhH), 5.12 (s, 106H, —OCH2Ph- and —OCH2PhCH3), 4.54 (s, 104H, -PhCH2Cl), 4.27 (s, 208H, —CH2OCOO—), 2.23 (s, 3H, —CH3Ph of 4-MBA), 1.23 (s, 156H, —CH3). Degree of polymerization (DP) of MTC-BnCl is 52. The degree of polymerization was estimated by comparing the integral of methyl proton of 4-MBA (the initiator) at 2.23 ppm to that of methylene proton of benzyl chloride fragment at 4.54 ppm.

Example 4

Figure 3:
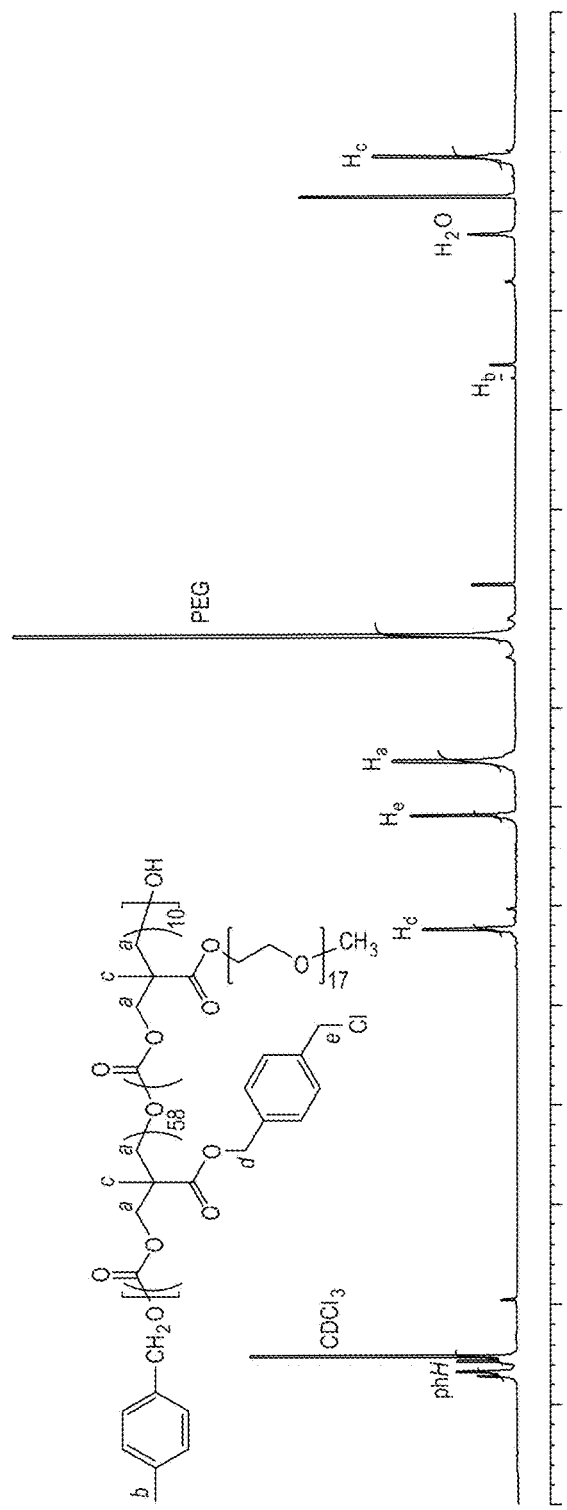
FIG. 3 is a $^1$H NMR spectrum of precursor polymer P-2 (labeled A).

Preparation of precursor polymer P-2, poly[(MTC-BnCl)$_x$-ran-(MTC-PEG)$_y$], for theoretical amounts x=80 and y=10. In a glovebox, 4-methylbenzyl alcohol (4-MBA, 2.24 mg, 0.018 mmol), MTC-PEG (0.201 g, 0.216 mmol) and MTC-BnCl (0.43 g, 1.44 mmol) were added to the solution of TU (6 mg, 0.016 mmol) in 1 mL of DCM, followed by adding DBU (2.4 microliters, 0.016 mmol) to initiate the polymerization. After 20 minutes, a solution of TU (20.7 mg, 0.056 mmol) and DBU (8.4 microliters, 0.056 mmol) in 1 mL of DCM was added to the reaction mixture, and the reaction mixture was stirred for 1 hour before benzoic acid (about 10 mg) was added to quench the polymerization. Finally, the reaction solution was concentrated to dryness, and the resulting crude product was purified by column chromatography on a SEPHADEX LH-20 column with THF as eluent, giving poly[(MTC-BnCl)$_{58}$-ran-(MTC-PEG)$_{10}$] as a white viscous solid (0.6 g, 95%). PDI: 1.20. $^1$H NMR (400 MHz, CDCl$_3$, 22° C.): delta 7.31 (m, 236H, PhH), 5.12 (s, 118H, $_O$CH2Ph- and —OC$_{H2}$PhCH3), 4.54 (s, 116H, -PhCH2Cl), 4.27 (s, 276H, —CH$^2$OCOO— and —COOCH2-MP$_E$G), 3.64 (s, 680H, H of MPEG), 2.24 (s, 3H, —CH3Ph of 4-MBA), 1.23 (s, 204H, —CH3). DP of MTC-BnCl and MTC-PEG is 58 and 10, respectively. The degree of polymerization was estimated by comparing the integral of methyl proton of 4-MBA (the initiator) at 2.24 ppm to that of methylene proton of the benzyl chloride fragment at 4.54 ppm as well as that of ethylene proton of MPEG at 3.64 ppm. FIG. 3 is a $^1$H NMR spectrum of P-2.

Precursor polymers are listed below in Table 6. Variables x+y (mmoles repeat unit containing the chlorobenzyl side chain), and z (mmoles of repeat unit containing the MPEG side chain) are shown in Scheme 2 above. 4-MBA is 4-methylbenzyl alcohol.

TABLE 6

| | | | Theoretical | | Analyzed | |
|---|---|---|---|---|---|---|
| Example | Name | I'—OH | x + y (chloro benzyl) | z (MPEG-1k) | x + y (chloro benzyl) | z (MPEG-1k) |
| 3 | P-1 | 4-MBA | 80 | 0 | 52 | 0 |
| 4 | P-2 | 4-MBA | 80 | 10 | 58 | 10 |
| 5 | P-3 | 4-MBA | 80 | 0 | 65 | 0 |
| 6 | P-4 | 4-MBA | 80 | 0 | 60 | 0 |
| 7 | P-5 | 4-MBA | 80 | 10 | 62 | 10 |
| 8 | P-6 | 4-MBA | 80 | 10 | 64 | 10 |
| 9 | P-7 | 4-MBA | 80 | 10 | 64 | 10 |
| 10 | P-9 | 4-MBA | 80 | 10 | 55 | 8 |
| 11 | P-10 | MPEG-5k | 80 | 0 | 68 | 0 |

The precursor polymers were treated step-wise with dopamine and either trimethylamine (TMA) or dimethyl benzyl amine (DMBA) to form cationic polymers bearing side chain catechol and side chain quaternary amine groups, as shown below in Scheme 3. I' is 4-methyl benzyl or MeO-(CH$_2$CH$_2$O)$_{n-1}$CH$_2$CH$_2$—*, where n=117.

Scheme 3.

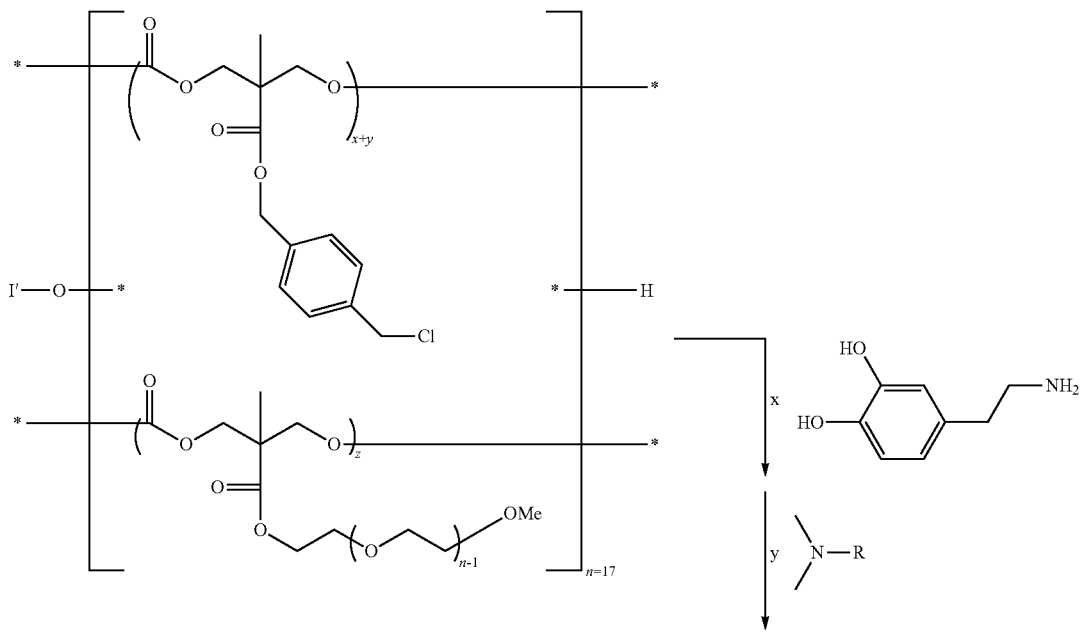

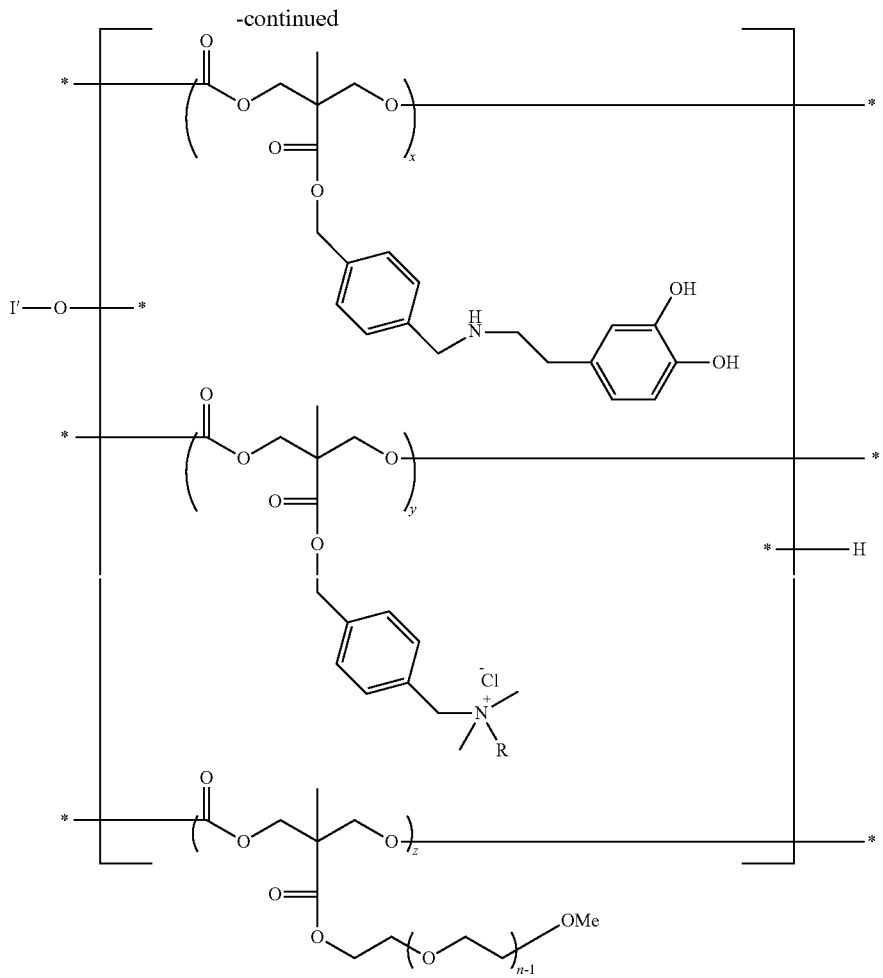

Example 12

The preparation of cationic polymer CP-1 is representative. The above precursor polymer P-1, poly(MTC-OBnCl)$_{52}$, (0.4 g) was dissolved in acetonitrile (20 mL) and under nitrogen gas the solution was transferred to a pressured vessel that was cooled with dry ice. Trimethylamine (TMA) was condensed into the vessel and the vessel was sealed. The reaction mixture was stirred overnight at room temperature and concentrated to dryness to remove acetonitrile and excess TMA. The crude product was purified by dialysis (molecular weight cutoff (MWCO) of dialysis membrane was 1,000) against a mixture of (acetonitrile:isopropanol=1:1) for 2 days. The resulting solution was concentrated to dryness and the resulting product was dried in vacuo to give cationic polycarbonate CP-1 as white viscous solid (0.42 g, 88%). $^1$H NMR (400 MHz, DMSO-d$_6$, 22° C.): delta 7.49 (m, 212H, PhH), 5.17 (s, 106H, —OCH2Ph- and —OCH2PhCH3), 4.69 (s, br, 104H, -PhCH2N$^\oplus$(CH3)3), 4.29 (s, 208H, —CH2OCOO—), 3.05 (s, 468H, -PhCH2N$^\oplus$(CH3)3), 2.27 (s, 3H, —CH3Ph of 4-MBA), 1.20 (s, 156H, —CH3). Quaternizing degree: ~100%.

Example 13

Figure 4:
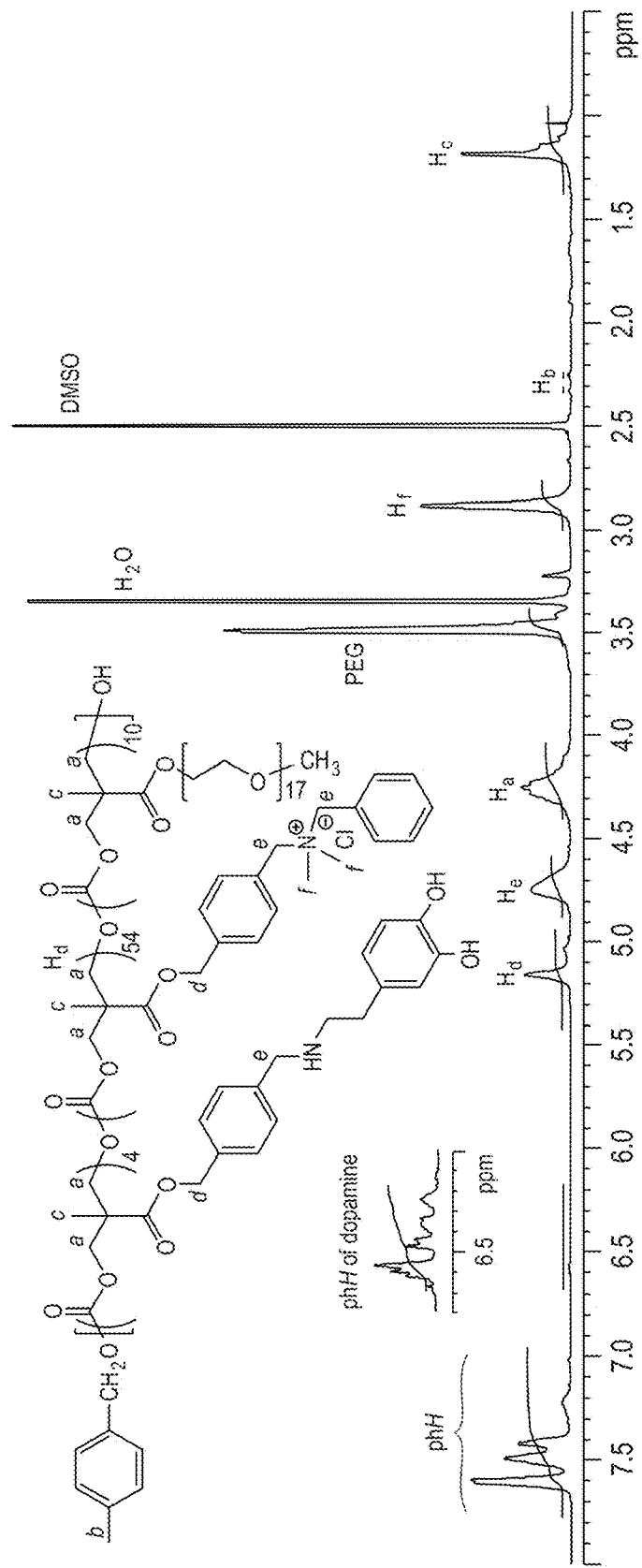
FIG. 4 is a $^1$H NMR spectrum of cationic polymer CP-2 (labeled B)

Preparation of dopamine-containing cationic polymer poly[(MTC-dopamine)$_x$-ran-(MTC-BnCl)$_y$-ran-(MTC-PEG)$_z$], CP-2. The details of the procedure for preparation of CP-2 represent a typical example of brush-like cationic polycarbonates containing dopamine and short PEG side chain groups. Under nitrogen atmosphere the above precursor polymer 4-MBA-Poly[(MTC-OBnCl)$_{58}$-ran-(MTC-PEG)$_{10}$] (P-2), (0.6 g, 0.021 mmol), was added to a dopamine solution (48 mg, 0.27 mmol) in a mixture of dimethylsulfoxide (DMSO, 10 mL), acetonitrile (10 mL) and isopropanol (10 mL). The reaction mixture was stirred for 10 hours at ambient temperature. N,N-dimethyl benzylamine (DMBA, 2.0 mL, 13.6 mmol) was added to the reaction solution, and the reaction mixture was stirred overnight. The reaction mixture was concentrated and dialyzed against a mixture of acetonitrile and isopropanol 1:1 by volume (MWCO of dialysis membrane: 1,000 Da) for 2 days. The solution was concentrated to dryness and the resulting product was dried in vacuo to give cationic polymer CP-2 as a brown viscous solid (0.62 g, 80%). $^1$H NMR (400 MHz, DMSO-d$_6$, 22° C.): delta 7.48 (m, 506H, PhH), 6.20-6.70 (m, 4H, PhH of dopamine), 5.16 (s, 118H, —OCH$_2$Ph- and —OCH$_2$PhCH$_3$), 4.75 (s, br, 224H, -PhCH$_2$N$^\oplus$(CH$_3$)$_2$(CH$_2$Ph) and -PhCH$_2$-dopamine), 4.26 (s, 292H, —CH$_2$OCOO— and —COOCH$_2$-MPEG), 3.50 (s, 680, H of MPEG), 2.89 (s, 324H, -PhCH$_2$N$^\oplus$(CH$_3$)$_2$(CH$_2$Ph)), 2.32 (s, 3H, —CH$_3$Ph of 4-MBA), 1.18 (s, 204H, —CH$_3$). The number of MTC-dopamine subunits and MTC-OBn-DMBA subunits in the cationic polymer is 4 and 54, respectively. The number of MTC-dopamine (i.e., carbonate repeat units containing the catechol side chain) was estimated by comparing the integral of ethylene proton of MPEG at 3.50 ppm to that of phenyl proton of dopamine at 6.20-6.70 ppm. The difference between the numbers of MTC-BnCl and MTC-dopamine is the number of MTC-OBn-DMBA (i.e., carbonate repeat units containing the quaternary dimethyl benzyl amine group on the side chain). FIG. 4 is a $^1$H NMR spectrum of CP-2.

Table 7 summarizes the cationic polymers formed. The subscripts x, y, and z are shown in Scheme 3 above.

TABLE 7

| Example | Name | Precursor Polymer | Dopamine (mmoles) | Tertiary Amine (mmoles) | Analyzed (mmoles) x (catechol) | y ($RN^+$) | z (PEG) | R |
|---|---|---|---|---|---|---|---|---|
| 12 | CP-1 | P-1 | | TMA | 0 | 52 | 0 | Methyl |
| 13 | CP-2 | P-2 | 0.27 | DMBA (13.6) | 4 | 54 | 10 | Benzyl |
| 14 | CP-3 | P-3 | 0.88 | TMA (45.4) | 18 | 47 | 0 | Methyl |
| 15 | CP-4 | P-4 | 0.49 | TMA (45.4) | 10 | 50 | 0 | Methyl |
| 16 | CP-5 | P-5 | 0.11 | TMA (45.4) | 2 | 60 | 10 | Methyl |
| 17 | CP-6 | P-6 | 0.22 | TMA (45.4) | 4 | 60 | 10 | Methyl |
| 18 | CP-7 | P-7 | 0.41 | TMA (45.4) | 10 | 54 | 10 | Methyl |
| 19 | CP-9 | P-9 | 0.26 | Dimethyl butyl amine (11.4) | 4 | 51 | 8 | Butyl |
| 20 | CP-10 | P-10 | 1.06 | TMA (45.4) | 20 | 48 | 0 | Methyl |

Preparation of Silicone Rubber Samples

Silicone rubber samples were prepared by mixing and curing components in the SYLGARD-184 kit. Base and curing agents in the kit were mixed thoroughly and cast on a glass slide (for LIVE/DEAD cell staining and confocal studies), in a 96-well plate (for XTT assay and hemolysis test) or a 48-well plate (for colony assay). After curing overnight at 70° C., the silicone rubber formed on the glass slide was cut into pieces of 0.5 cm×0.5 cm with thickness of about 1 mm. Then, the silicone rubbers were immersed in DI water and put in an ultrasonic bath for 2 minutes, followed by drying with a nitrogen flow to obtain clean rubber surfaces.

Polymer Coating on Silicone Rubber Surface

The cleaned silicone rubber surfaces and sterile catheter segments with length of about 1 cm were immersed in polymer solution (0.5 mM, 0.25 mM, and 0.1 mM in cationic polymer) in 10 mM Tris buffer (pH 8.5) for 24 hours at 70° C., and then rinsed with Tris buffer three times before usage. For example, a 0.5 mM polymer solution was prepared by dissolving 0.009 g CP-1 in 1 mL Tris buffer.

Figure 5:
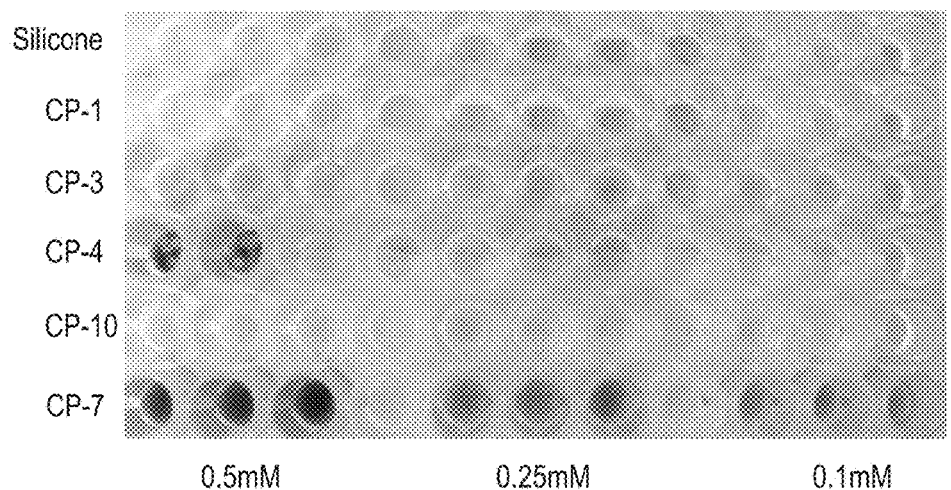
FIG. 5 is a black and white photograph of coatings of different polymers at various concentrations on silicone rubber that were formed in a 96-well plate (coatings were made in triplicate at each concentration 0.5 mM, 0.25 mM, and 0.1 mM). A successful coating is indicated by a brown film on the silicone rubber, appearing as darker gray in the black and white photograph.

FIG. 5 is a photograph of coatings with different polymers at various concentrations on the silicone rubber that was formed in a 96-well plate (coatings were made in triplicate at each concentration 0.5 mM, 0.25 mM, and 0.1 mM). Cationic polymer CP-7 formed a visible brown coating layer (appearing darker gray in the photograph) on the silicone at all concentrations tested. Homopolymer CP-1 without dopamine, the random copolymer CP-3 with dopamine but without PEG, as well as the diblock copolymer CP-10 with dopamine and PEG were unable to provide a visible coating even at the highest concentration of 0.5 mM. At 0.5 mM, the coating of the random copolymer CP-4 was visible, but it was not as densely colored as CP-7.

Test Procedures

Colony Assay for Solution Viability of Bacteria

The concentration of bacteria (*S. aureus, S. epidermidis* and *E. coli*) in Mueller Hinton Broth (MHB) was adjusted to the optical density (O.D.) reading of 0.07 at the wavelength of 600 nm on a microplate reader (TECAN, Switzerland), which corresponds to the concentration of about $10^8$ CFU/mL. Then, the bacterial solution was diluted by 1000 times to the concentration of $10^5$ CFU/mL. Bacterial solution (20 microliters) was added onto uncoated and polymer-coated silicone rubbers that were formed in a 48-well plate. After incubation at 35° C. for 24 hours, bacterial solution was taken out from the rubber surfaces and diluted with an appropriate dilution factor. The diluted bacterial solution was streaked onto agar plates (LB Agar from 1st Base), and the number of the colony-forming units (CFUs) was counted after incubation for 18 hours at 37° C. Each colony assay test was carried out in triplicate.

XTT Assay for Surface Fouling

A (2-methoxy-4-nitro-5-sulfo-phenyl)-2H-tetrazolium-5-carboxanilide (XTT) reduction assay was used to quantify the live *S. aureus* and *S. epidermidis* on the surface by measuring the mitochondrial enzyme activity in live cells. Mitochondrial dehydrogenases of the viable bacterial cells reduce XTT to an orange colored formazan derivative, and the optical density (OD) change was then recorded to analyze the viability of the cells. In this experiment, *S. aureus* (20 microliters, $10^5$ CFU/mL) or *S. epidermidis* (20 microliters, $10^5$ CFU/mL) were seeded onto the untreated and polymer-treated silicone rubber surfaces, and incubated for 24 hours. After the incubation, the rubber surfaces were washed three times with sterile PBS and then 100 microliters of PBS, 10 microliters of XTT (1 mg/mL) and 2 microliters of menadione (0.4 mM) were added onto the rubber surfaces. After incubation at 37° C. for 2 hours, the absorbance at a wavelength of 490 nm of the samples was measured using a microplate reader (TECAN, Sweden, 600 nm used as reference wavelength).

LIVE/DEAD Bacterial Viability Assay

To visualize the viable bacterial cells on the untreated and polymer-treated silicone rubber surfaces, a LIVE/DEAD BacLight™ bacterial viability kit (L-7012, Invitrogen) with two staining agents was used. The propidium iodide, a red-nucleic acid staining agent, was used to label dead bacterial cells by penetrating damaged cell membrane. Meanwhile, SYTO® 9, a green-fluorescent nucleic acid staining agent, was used to label all the bacterial cells by penetrating cells both with intact and damaged membranes. The bacteria ($10^5$ cells/mL, 10 microliters) were seeded on the untreated and polymer-treated silicone rubber surfaces, followed by incubation at 35° C. for 24 hours. After incubation, the silicone rubber surfaces were washed with PBS buffer for three times. Then they were soaked in a dye solution (5.01 micromolar in SYTO and 30 micromolar in propidium iodide in PBS) at room temperature in the dark for 15 min. The stained bacterial cells were observed using an oil immersed 63× objective lens of a Zeiss LSM 5 DUO laser scanning confocal microscope (Germany). The number of live and dead bacterial cells shown in green and red respectively in the images was analyzed by the open-source software ImageJ (Fiji).

Protein Adsorption Measurement by Quartz Crystal Microbalance with Dissipation (QCM-D)

QCM-D (Q-sense E4, Sweden) was used to determine the adsorption of a model protein bovine serum albumin BSA on polymer-coated surfaces. Gold-coated quartz crystals with oscillating frequency of 4.95 MHz were used as sensors and substrates for the experiments. The sensors were cleaned as the manufacturer suggested by 10 minutes of UV/Ozone treatment and followed by 5 minutes of piranha solution (ammonia, hydrogen peroxide and ultrapure water in a volume ratio of 1:1:5) at 75° C. The sensors were then rinsed with DI water, and dried with nitrogen gas. The cleaned sensors were immersed in polymer solution at 70° C. for 24 hours, and then rinsed with Tris buffer and dried with nitrogen flow. The polymer-coated sensors and uncoated sensors were placed in the QCM-D instrument and the change of sensors' frequency (f) and dissipation (D) were monitored. The tris buffer was flown over the sensors until stable frequency (f) and dissipation (D) baseline were obtained. After the equilibrium, BSA solution (50 μg/mL in PBS) was pumped into the sensor chambers at a flow rate of 10 microliters/minute until the frequency was stabilized. PBS was then pumped into the chambers to wash off loosely bound BSA molecules. The real-time frequency of the third overtone (f3) and dissipation (D3) was monitored and used to analyze BSA adsorption.

Results

Figure 6:
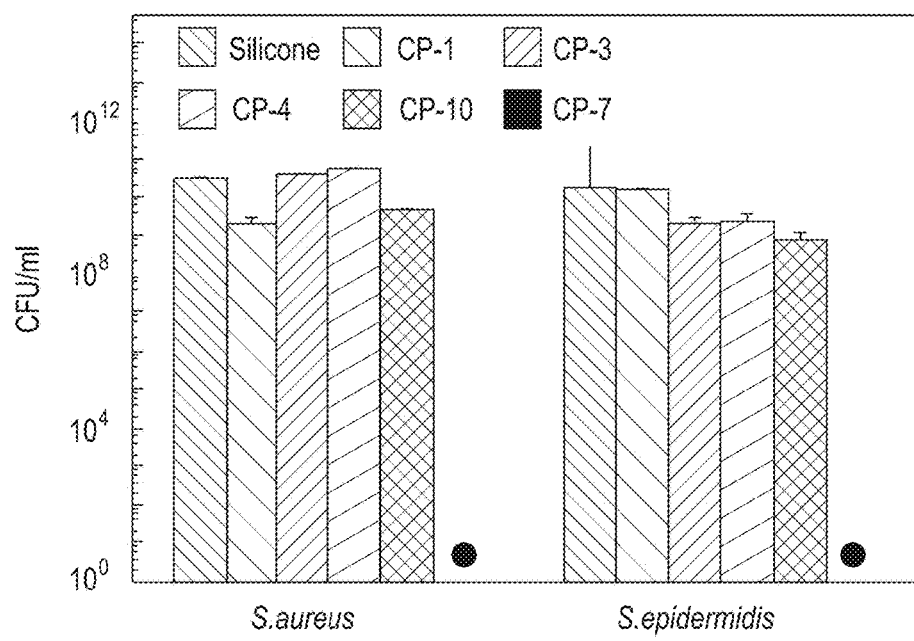
FIG. 6 is a bar graph showing colony forming units of *Staphylococcus aureus* (*S. aureus*) and *Staphylococcus epidermidis* (*S. epidermidis*) in solution after 24 hours contact with untreated and polymer-treated silicone rubber (polymer concentration: 0.5 mM). A solid circle indicates no colony found.
Figure 7:
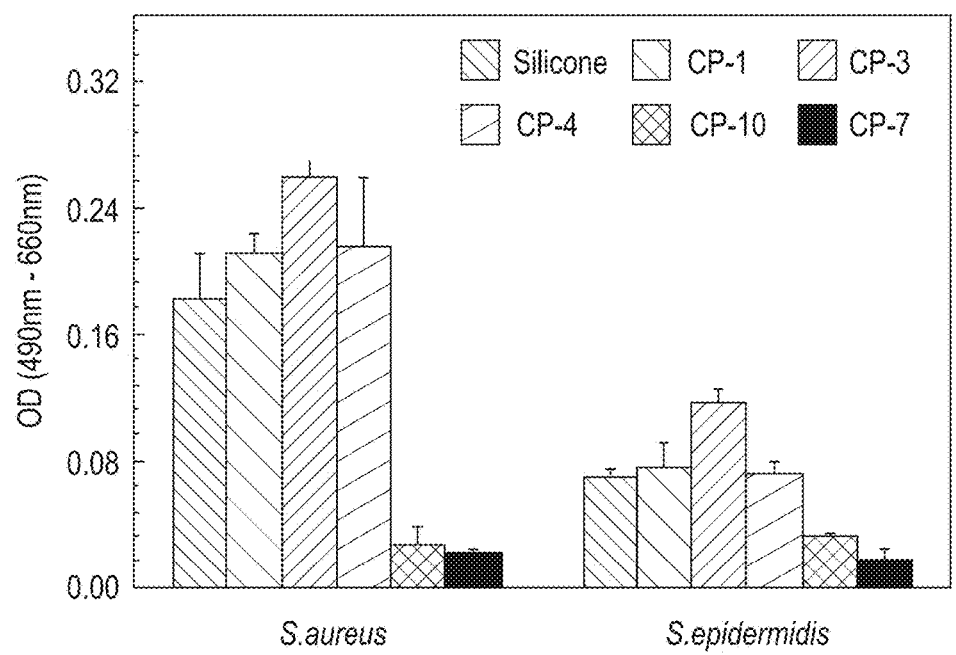
FIG. 7 is a bar graph showing viability (XTT reduction assay, where XTT is (2-methoxy-4-nitro-5-sulfo-phenyl)-2H-tetrazolium-5-carboxanilide) of *S. aureus* and *S. epidermidis* on untreated and treated silicone rubber surfaces (polymer concentration: 0.5 mM).

The CP-7 coating not only eradicated *S. aureus* and *S. epidermidis* in solution (FIG. 6, bar graph), but it also prevented fouling on the silicone rubber surface (FIG. 7, bar graph, XTT results). By comparison, the silicone rubber treated with CP-1, CP-3, and CP-4 did not have effective antibacterial (FIG. 6) or antifouling properties (FIG. 7). Although the silicone rubber treated with CP-10 showed an antifouling effect against both types of bacteria (FIG. 7), it was ineffective (i.e., did not kill) the bacteria in solution (FIG. 6). The results demonstrate that the coating on silicone rubber prepared with brush-like polymer CP-7 containing side chain PEG groups was more effective than coatings prepared with the random copolymers without side chain PEG groups (CP-1, CP-3, and CP-4) and was more effective than the coating prepared with the diblock copolymer having a PEG block (CP-10). The brush-like polymer coating of CP-7 killed the bacteria and prevented bacterial fouling effectively.

Figure 8:
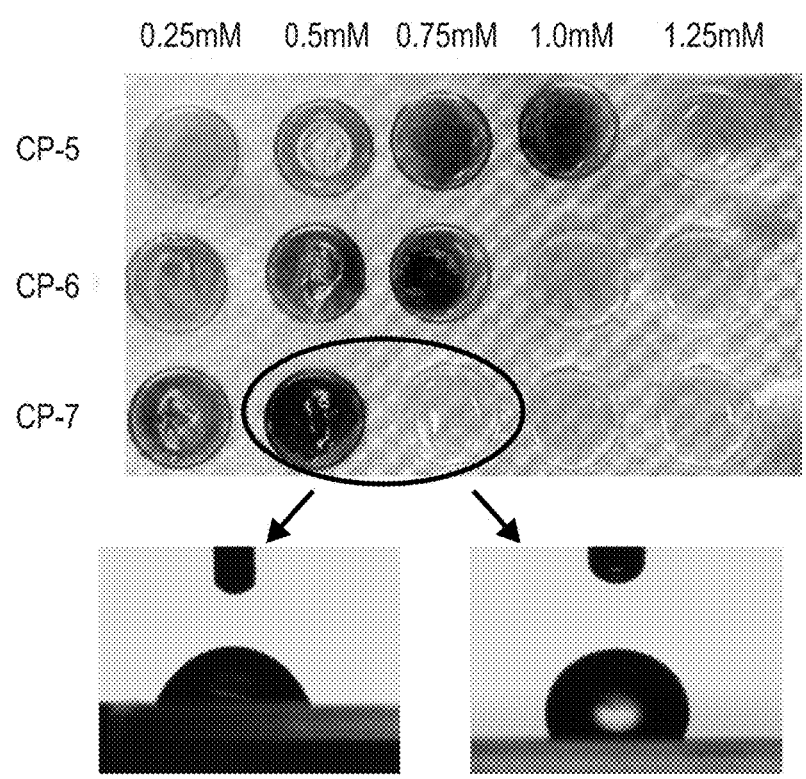
FIG. 8 is a black and white photograph of coatings on silicone rubber that were formed in a 96-well plate at various cationic polymer (CP-5, CP-6, and CP-7) concentrations (0.25 mM to 1.25 mM). The cationic polymers have different amounts of side chain catechol groups and similar amounts of side chain cationic groups and side chain PEG groups. The images below the photograph show contact angle results of silicone rubber surfaces treated with cationic polymer CP-7 at 0.5 and 0.75 mM, respectively.

The effect of the side chain dopamine group on antibacterial and antifouling activities of brush-like polymer coating was further studied by varying the dopamine content in the cationic polymer while maintaining similar content of cationic groups and side chain PEG groups (CP-5, CP-6 and CP-7). The properties of these coatings were both dopamine and polymer concentration-dependent. As shown in photograph of FIG. 8, the cationic polymers formed a uniform coating only below a critical concentration. The critical concentration was 1.0, 0.75 and 0.50 mM for CP-5, CP-6 and CP-7, respectively. FIG. 8 shows the critical concentration decreased as the content of side chain dopamine increased in this cationic polymer series. For example, polymer CP-7, which contains ten dopamine-containing subunits, formed a uniform dark coating at 0.5 mM as demonstrated by a reduced contact angle in the bottom left image of FIG. 8, whereas a coating prepared at a CP-7 concentration below 0.5 mM was less densely colored (FIG. 8). When the polymer concentration increased to 0.75 mM or above, the contact angle of the silicone rubber surface treated with the polymer was similar to that of the surface before the treatment, indicating that the cationic polymer was unable to coat the silicone surface (FIG. 8) at concentrations above 0.5 mM. Without being bound by theory, this behavior at higher concentration could be related to polymerization of the side chain catechol groups between polymer chains in solution before they can interact with the silicone rubber surface. Increasing the dopamine content of the polymer resulted in self-polymerization in solution at lower polymer concentration. This finding indicates that each polymer has an optimal polymer concentration for effectively coating the surface of the silicone rubber.

Figure 9:
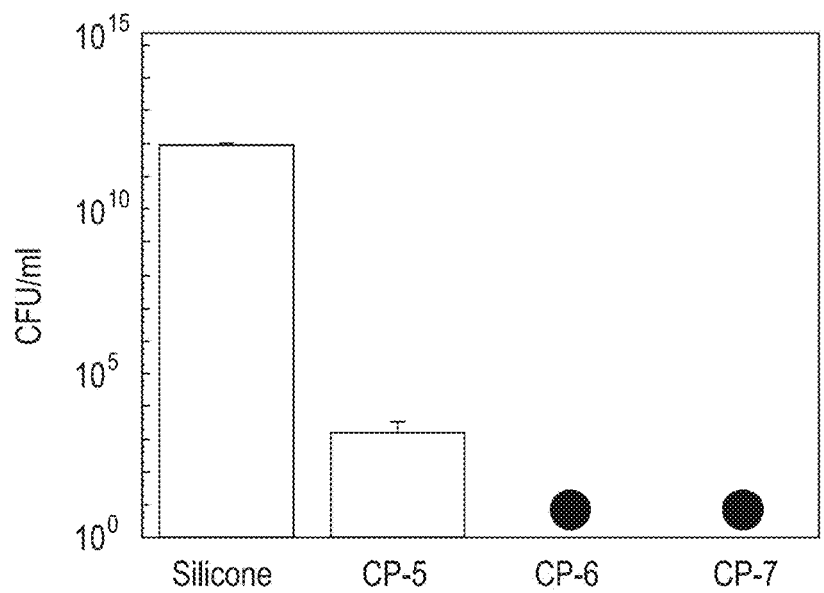
FIG. 9 is a bar graph showing colony forming units of *S. aureus* in the solution after 24 hours of contact with untreated and polymer-treated silicone rubber (CP-5, CP-6, and CP-7) at the optimal concentration of each cationic polymer (i.e., 1.0, 0.75 and 0.5 mM, respectively). A solid circle indicates no colony found. All coatings killed *S. aureus* in solution effectively.
Figure 10:
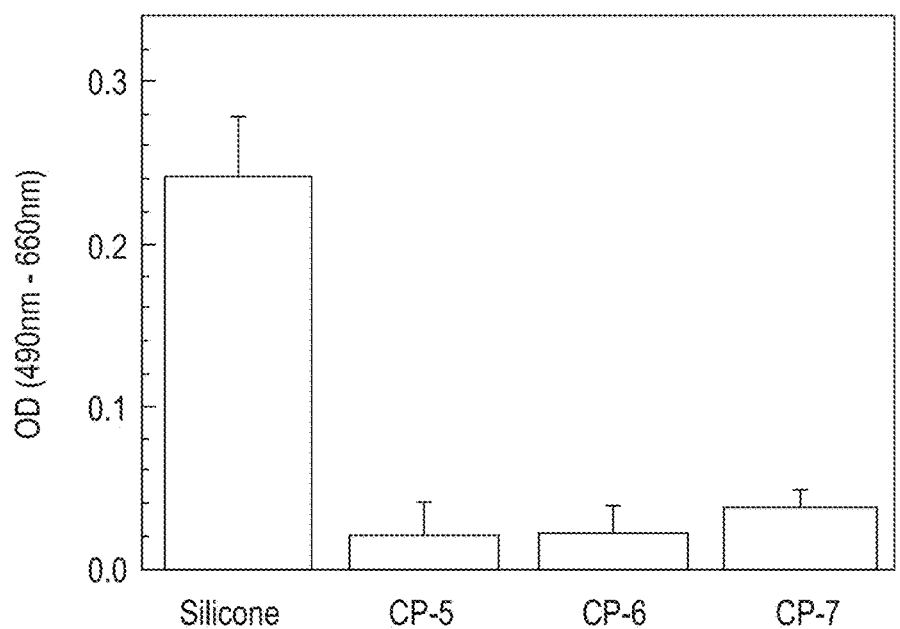
FIG. 10 is a bar graph showing viability (XTT reduction assay) of *S. aureus* on untreated and treated silicone rubber surfaces (CP-5, CP-6, and CP-7) at the optimal concentration of each cationic polymer (i.e., 1.0, 0.75 and 0.5 mM, respectively). Excellent antifouling activity was observed for each coating against the Gram-positive bacteria.

To compare the antibacterial and antifouling activities of CP-5, CP-6 and CP-7 coatings, silicone rubber surfaces were coated with these polymers at their optimal concentrations (i.e., 1.0, 0.75 and 0.5 mM, respectively). As shown in FIG. 9, each coating killed *S. aureus* in solution effectively. Viability tests (XTT results) also indicated excellent antifouling activity for each of the coatings against the Gram-positive bacteria (FIG. 10).

Figure 11:
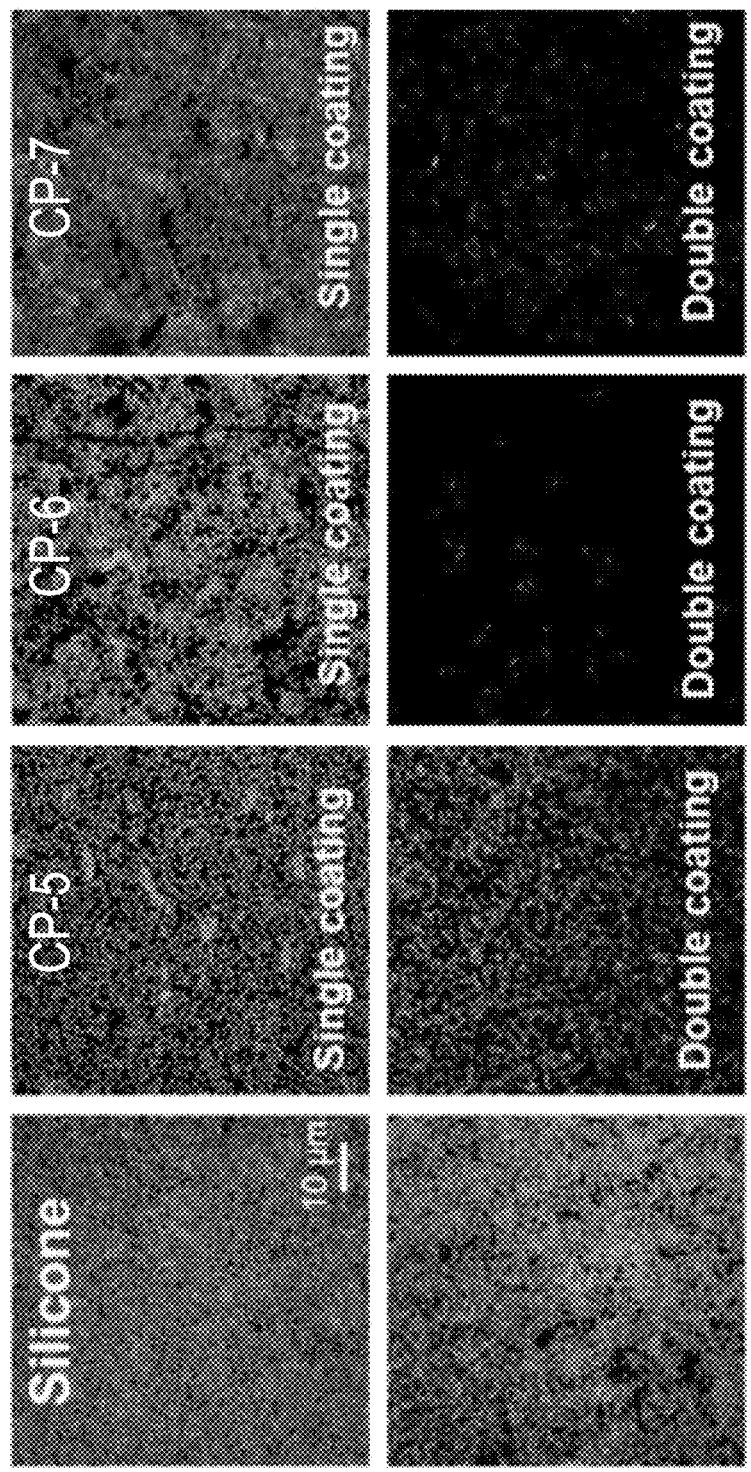
FIG. 11 is a series of grayscaled confocal images of *Escherichia coli* (*E. coli*) cells after 24 hours of incubation with untreated and polymer-treated silicone rubber surfaces prepared at the optimal concentration of each cationic polymer (i.e., 1.0, 0.75 and 0.5 mM of CP-5, CP-6, and CP-7, respectively). *E. coli* cells were stained using LIVE/DEAD BacLight™ Bacterial Viability Kits. The green (lighter gray) and red regions (darker gray) represent live and dead cells, respectively. The top images show results for single coatings of the cationic polymers. The bottom images show results for double coatings of cationic polymers, where the double coatings were prepared using the same coating conditions. The live/dead cell counts are shown in the bar graph of FIG. 13 for the double coatings.
Figure 12:
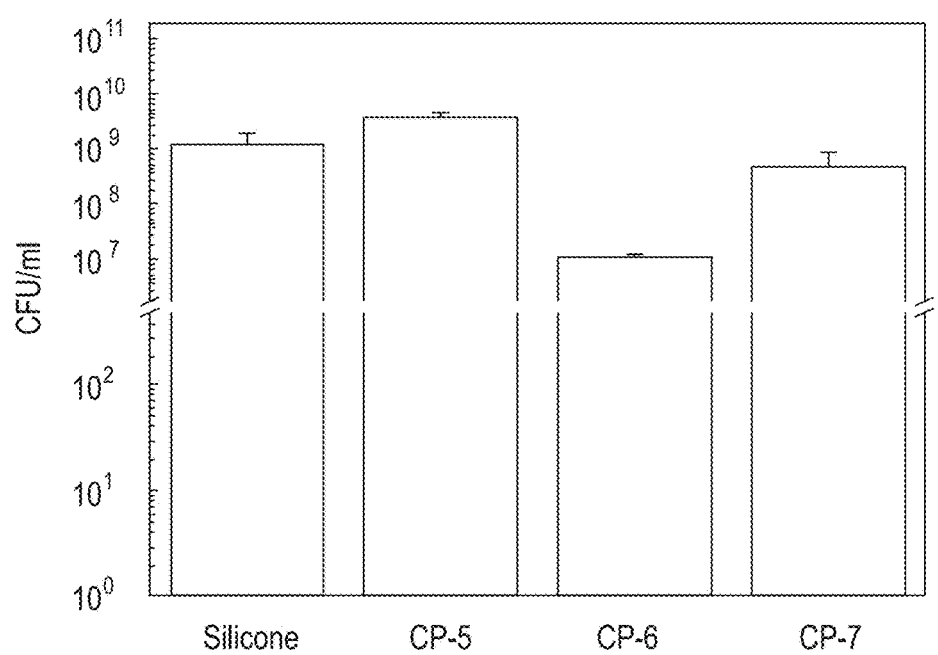
FIG. 12 is a bar graph showing colony forming units of *E. coli* in solution after 24 hours contact of an *E. coli* solution with untreated and polymer-treated silicone rubber (double coatings) prepared at the optimal concentration of each cationic polymer (i.e., 1.0, 0.75 and 0.5 mM of CP-5, CP-6, and CP-7, respectively).
Figure 13:
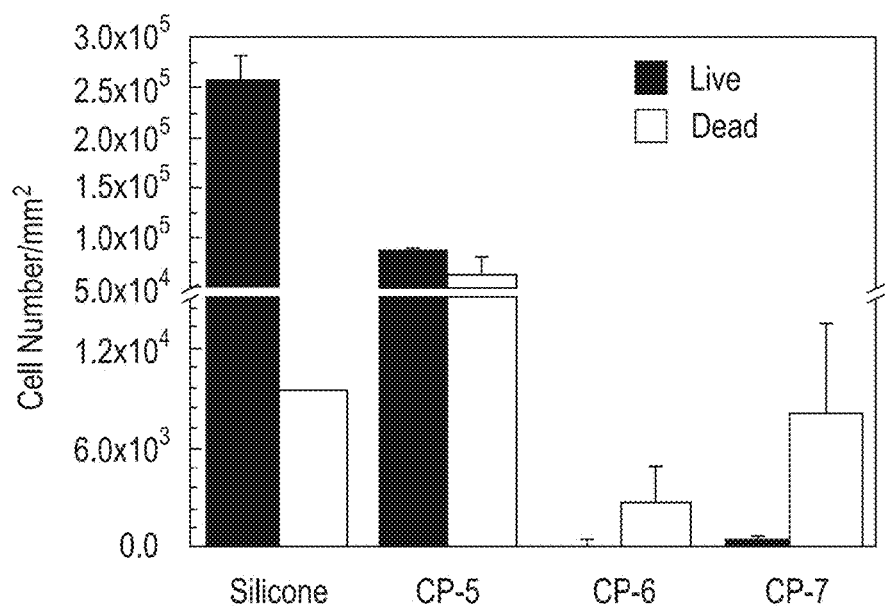
FIG. 13 is a bar graph showing the number of live and dead *E. coli* cells after 24 hours of contact of an *E. coli* solution with the untreated and polymer-treated silicone rubber surfaces (double coatings) prepared at the optimal concentration of each cationic polymer (i.e., 1.0, 0.75 and 0.5 mM of CP-5, CP-6, and CP-7, respectively).

The antibacterial and antifouling activities of the polymer coatings were further tested against Gram-negative bacteria *E. coli*. A single coating of these polymers was not effective in killing *E. coli* in solution and failed to prevent *E. coli* from fouling on the surfaces (FIG. 11, a series of confocal images). To improve coating performance, two coating steps were performed under the same conditions. A significant reduction in *E. coli* colonies in solution was observed for double coatings of CP-6 and CP-7 on silicone rubber (FIG. 12, bar graph). In particular, the number of colonies decreased from $10^9$ CFU/mL on the untreated silicone surface to $10^7$ CFU/ml for the CP-6 double coating. The double coatings of CP-6 and CP-7 possessed excellent antifouling activities against *E. coli* as shown in FIG. 11 and the bar graph of FIG. 13. As seen in FIG. 13, there were about $2.5 \times 10^5$ cells/mm$^2$ live cells on the untreated silicone surface after 24 hours of incubation with *E. coli* solution ($10^5$ cells/mL), while less than 500 live cells on the surfaces with double coating of CP-6 and CP-7. These results indicate that for CP-6 and CP-7, a double coating is antibacterial and antifouling against Gram-negative bacteria.

Figure 14:
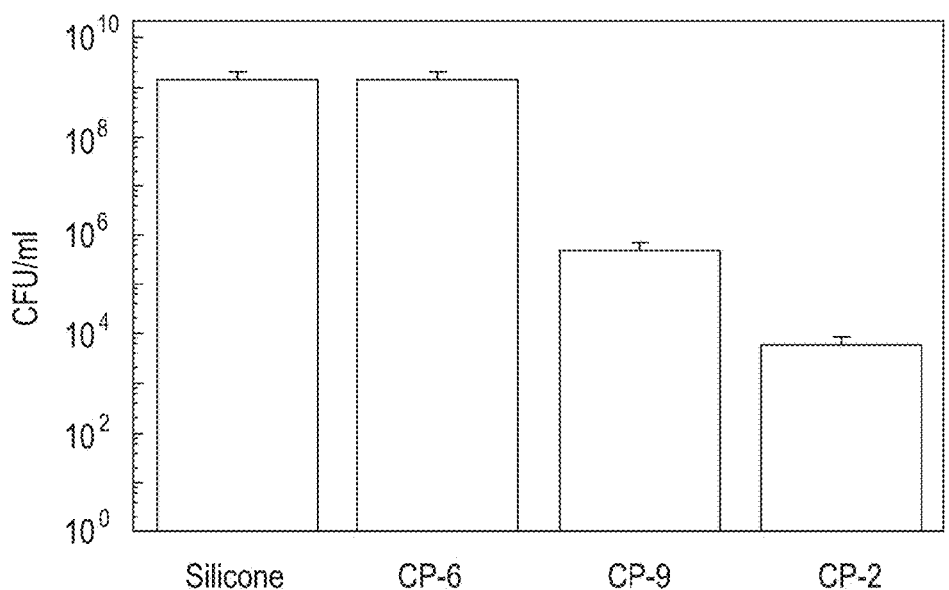
FIG. 14 is a bar graph showing colony forming units of *E. coli* in solution after 24 hours of contact of an *E. coli* solution with untreated and polymer-treated silicone rubber (single coating) prepared with cationic polymers CP-6, CP-9 and CP-2, each at 1.5 mM. CP-6 has quaternary groups formed with trimethylamine. CP-9 and CP-2 have quaternary groups formed from dimethylbutylamine and N,N-dimethylbenzylamine, respectively.
Figure 15:
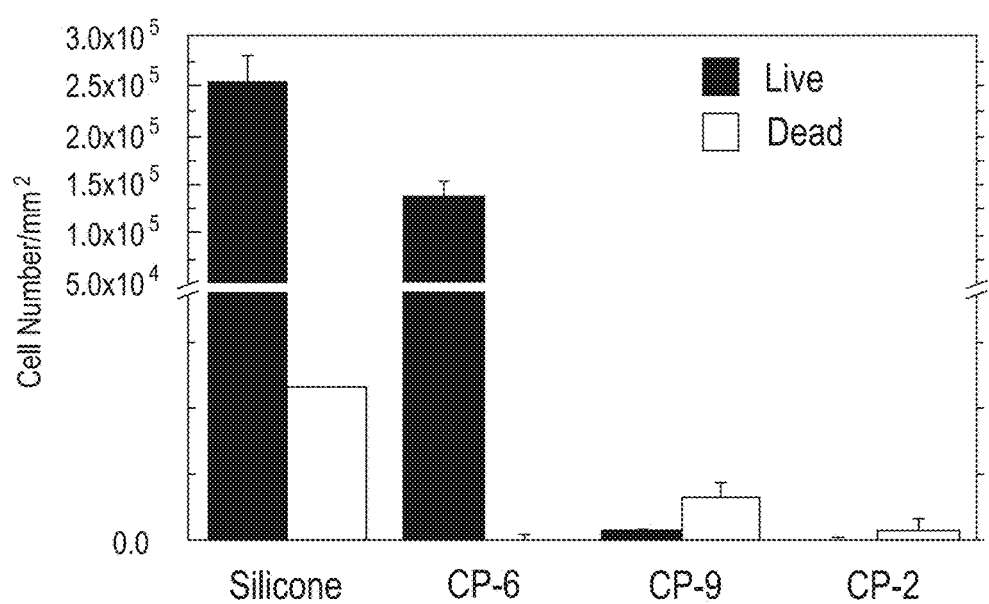
FIG. 15 is a bar graph showing the number of live and dead *E. coli* cells on the untreated and polymer-treated silicone rubber surfaces (single coatings) prepared with cationic polymers CP-6, CP-9 and CP-2, each at 1.5 mM.
Figure 16:
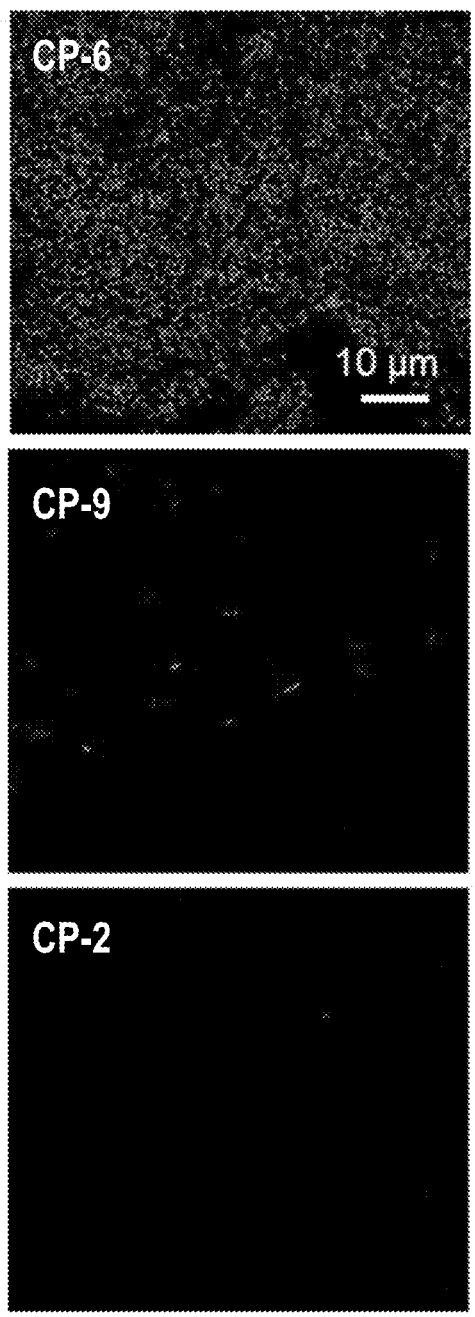
FIG. 16 is series of grayscaled confocal images after 24 hour incubation showing the number of live and dead *E. coli* cells on the untreated and polymer-treated silicone rubber surfaces (single coatings) prepared with cationic polymers CP-6, CP-9 and CP-2, each at 1.5 mM. *E. coli* cells were stained using LIVE/DEAD BacLight™ Bacterial Viability Kits. The green (lighter gray) and red regions (darker gray) represent live and dead cells, respectively. The live/dead cell counts are shown in the bar graph of FIG. 12.

Cationic polymers having more hydrophobic quaternizing agents such as N,N-dimethylbutylamine (CP-9) and N,N-dimethyl benzylamine (CP-2) were synthesized and coated once onto silicone rubber surfaces using a polymer concentration of 1.5 mM. As shown in the bar graph of FIG. 14, the single coating of either CP-9 or CP-2 killed *E. coli* in solution more effectively than a coating prepared with CP-6 that was prepared with trimethylamine. The coating prepared with CP-6 utilized a CP-6 concentration of 0.75 mM. The coating prepared from N,N-dimethyl benzylamine-quaternized polymer CP-2 was the most effective among the three polymer coatings. Compared to the untreated silicone rubber surface, more than 99.999% and 99.9% *E. coli* cells were killed in solution after 24 hours of contact with the CP-2 and CP-9 coatings, respectively, whereas there was no apparent bacterial killing in solution for the CP-6 coating (FIG. 15, bar graph). From the confocal images of FIG. 16, there were barely live cells on the CP-2 and CP-9 coatings. In contrast, a large number of live cells (about $1.4 \times 10^5$ cells/mm$^2$) were observed on the coating of CP-6 coating that was quaternized using trimethylamine. These findings demonstrated that the antibacterial and antifouling activities against the Gram-negative bacteria E. coli were enhanced with the use of more hydrophobic quaternizing agents.

Simulated Blood Flow Condition Using X-Ray Photoelectron Spectroscopy (XPS)

Since the indwelling time of intravascular catheters can be as long as 5 days or more, the stability and long-term activities of the best polymer coating (i.e., CP-2 coating) were examined. The polymer coated catheter segment was connected to a pump (Heidolph, Germany) and flushed using this pump with phosphate-buffered saline (pH 7.4) at the flow rate of 250 ml/min at 37° C. to mimic the blood flow condition. After flushing in PBS for 7 days, the surface chemistry of the inner lumen of the polymer coated catheter segment was tested using x-ray photoelectron spectroscopy (XPS) (Kratos Axis HSi, Kratos Analytical, Shimadzu, Japan) with an Al Kα source (hv=1486.71 eV) and compared with the uncoated catheter and polymer-coated catheter before the PBS flushing experiment. The angle between the lumen surface and detector was kept at 90°. The survey spectrum ranging from 1100-0 eV was acquired with pass energy of 80 eV. All binding energies were referenced to the C is (C—C bond) at 284.5 eV.

Figure 17:
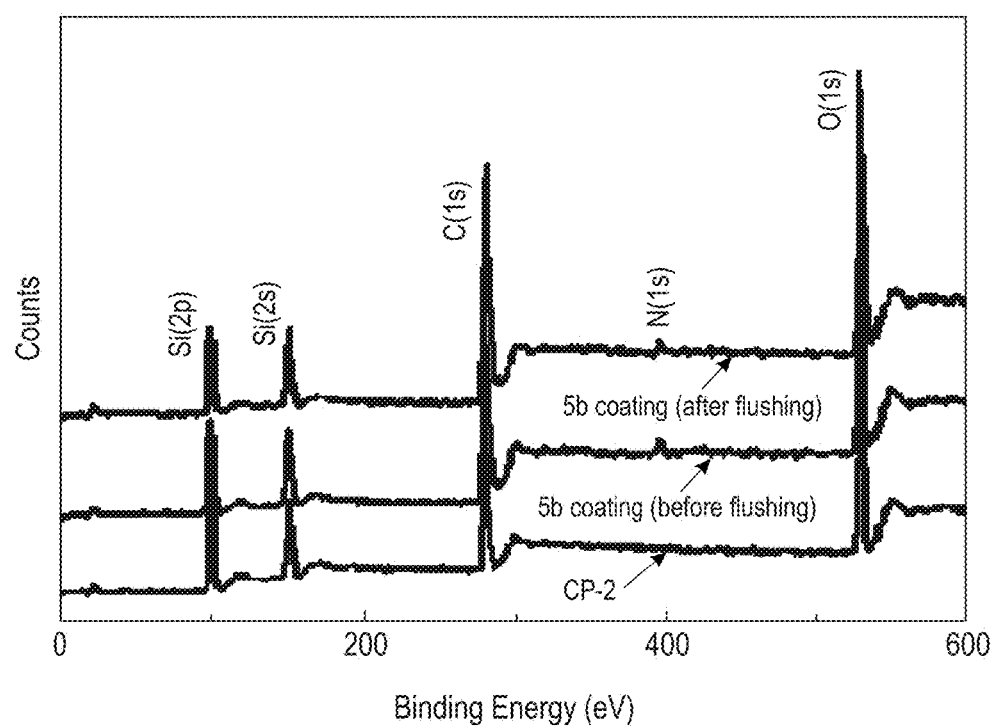
FIG. 17 is a series of XPS spectra obtained for the untreated and polymer-treated silicone rubber surfaces prepared with CP-2 (single coating) before and after flushing the samples for one week with phosphate-buffered saline (pH 7.4) at the flow rate of 250 ml/min at 37° C. to mimic the blood flow condition.

From the XPS spectra shown in FIG. 17, the nitrogen peak at 396 eV from the polymer was still seen even after flushing for one week. In addition, the composition of each element on the CP-2 coated rubber surface was similar before and after flushing with PBS (Table 8).

TABLE 8

| Element (%) | Catheter (%) | CP-2 Coating before flushing (%) | CP-2 Coating after flushing (%) |
|---|---|---|---|
| C (1s) | 36.26 | 59.12 | 58.88 |
| N (1s) | 0.0 | 2.01 | 1.75 |
| O (1s) | 23.88 | 24.03 | 22.53 |
| Si (2p) | 39.86 | 14.85 | 16.84 |

Figure 18:
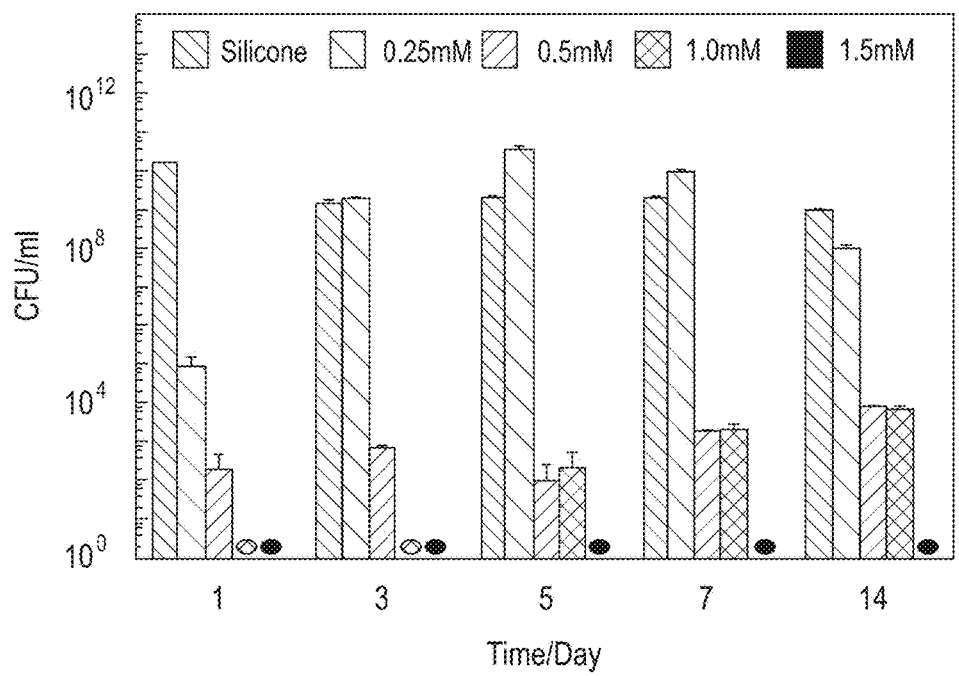
FIG. 18 is a bar graph showing *S. aureus* colony forming units over a two week period after contact with untreated and polymer-treated silicone rubber (single coating) prepared with cationic polymer CP-2 at various concentrations. Fresh bacterial solution ($10^5$ CFU/mL) was added to the CP-2 coated silicone rubber every 24 hours for two weeks. Solid circles indicate no colony found.
Figure 19:
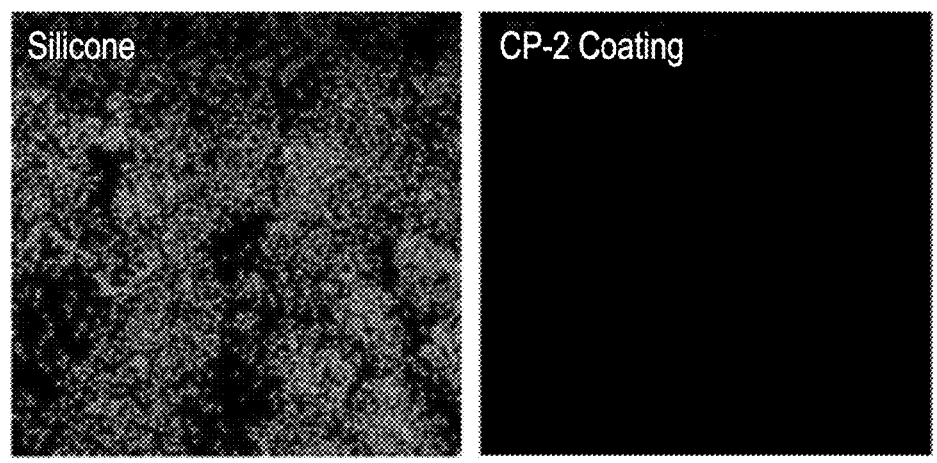
FIG. 19 is series of grayscaled confocal images after 14 days of *S. aureus* contact with untreated and polymer-treated silicone rubber (single coating) prepared with CP-2 at 1.5 mM. A fresh bacterial solution ($10^5$ CFU/mL) was added to the surfaces every 24 hours. *S. aureus* cells were stained using LIVE/DEAD BacLight™ Bacterial Viability Kits. The green (lighter gray) and red (darker gray) regions represent live and dead cells, respectively. No bacterial cells were found on the CP-2 coated surface.

These results indicated the presence of the polymer coating even after 7 days of PBS flushing. The long-term antibacterial and antifouling activities of the CP-2 coating were evaluated over 2 weeks by adding a fresh bacterial solution ($10^5$ CFU/mL) to the CP-2 coated rubber surface every 24 hours. As shown in the bar graph of FIG. 18, the CP-2 coating that was formed at a higher concentration (i.e., 1.5 mM) was able to eradicate S. aureus in the solution even after 14 days of incubation. Importantly, no bacterial cells were found on the CP-2 coated surface (FIG. 19, confocal images).

Hemolysis Assay

As the coating of medical devices, the biocompatibility of the coating with the blood is important. Therefore, the hemolysis of CP-2 coating was evaluated. Fresh rat blood was diluted to 4% (by volume) with PBS. Diluted rat blood 100 microliters of was placed on the uncoated and polymer-coated silicone rubber surfaces in each well of a 96-well plate, and 100 microliters of PBS was then added to each well. To allow hemolysis to occur, the plate was incubated for one hour at 37° C. Then the 96-well plate was centrifuged at 2200 rpm for 5 minutes. Aliquots of 100 microliters supernatant from each well were transferred to a new 96-well plate, and OD readings were recorded at 576 nm to assess hemoglobin release using a microplate reader (TECAN, Sweden). In this assay, red blood cells treated with 0.2% TRITON-X were used as a positive control, and the red blood cells in PBS were used as a negative control. Hemolysis percentage was calculated using the following formula: Hemolysis (%)=[($OD_{576nm}$ of the sample–$OD_{576nm}$ of the negative control)/($OD_{576nm}$ of the positive control–$OD_{576nm}$ of the negative control)]×100, where $OD_{576nm}$ is the optical density at 576 nm. The data shown in the figures are expressed as mean and standard deviation of three replicates.

Figure 20:
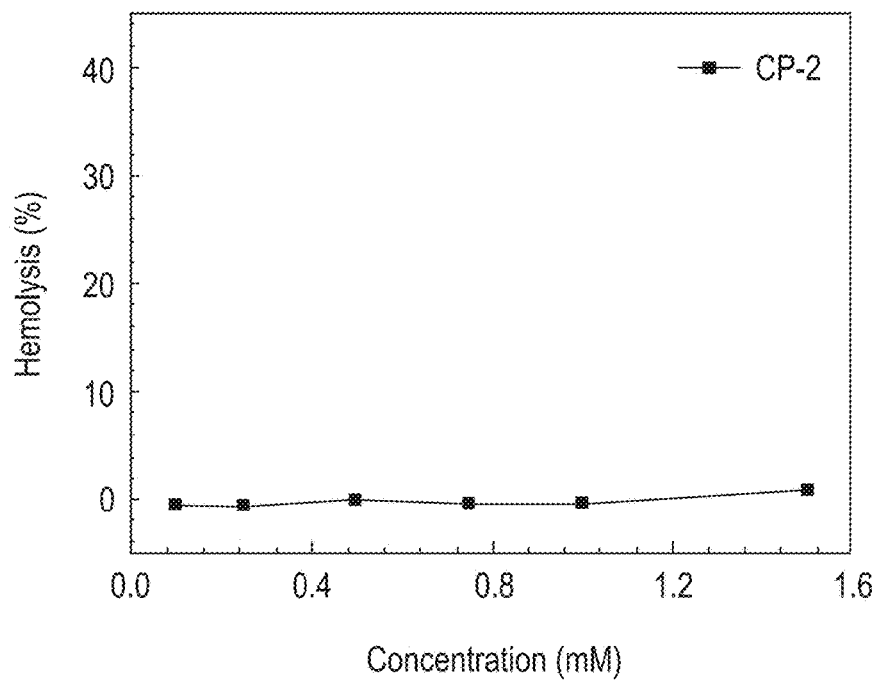
FIG. 20 is a graph showing the % hemolysis rat blood cells observed with CP-2 coated silicone rubber samples prepared using different CP-2 concentrations. No significant hemolysis was observed for any CP-2 concentration.
Figure 21:
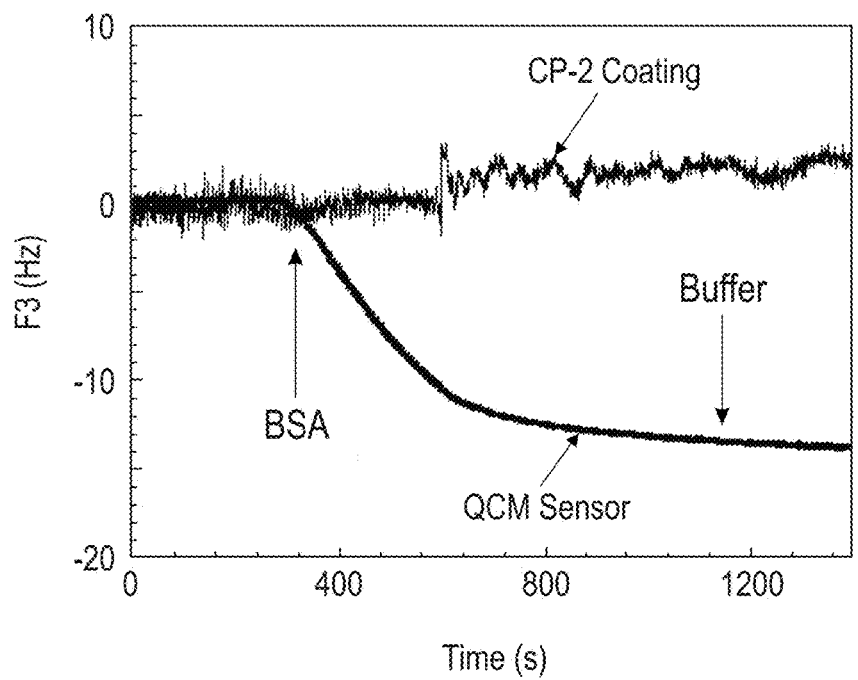
FIG. 21 is a graph showing the Quartz Crystal Microbalance (QCM) analysis showing the real-time frequency shift (F) of the QCM as a function of time for a CP-2 coated silicone rubber sample in the presence of the protein BSA (bovine serum albumen). No significant protein adsorption was observed on the CP-2 coated surface.

As shown in the graph of FIG. 20, the polymer coating at various concentrations induced no significant hemolysis, due to the presence of PEG components in CP-2. In addition, protein adsorption on the CP-2 coated surface prepared with a CP-2 concentration of 1.5 mM was also assessed by quartz crystal microbalance (QCM) under a flow condition because there is a large amount of proteins existing in the blood, and protein adsorption may mask the antibacterial and antifouling activities of polymer coatings. In the graph of FIG. 21, the decrease in the frequency of the $3^{rd}$ overtone of untreated QCM sensor suggested protein (BSA, bovine serum albumen) adsorption on the surface of the sensor. In contrast, no significant BSA adsorption was observed on the CP-2 coated surface.

In conclusion, the brush-like polycarbonates having a first subunit comprising a side chain PEG oligomer, a second subunit comprising a side chain catechol, and a third subunit comprising a side chain cationic group (e.g., quaternary amine group) have been successfully synthesized and coated onto silicone rubber surfaces by a one-step immersion process. A small number of the catechol groups is sufficient to facilitate the polycarbonate adhering to the silicone rubber surface. The coated silicone rubber is able to kill both Gram-positive and Gram-negative bacteria in solution and can prevent bacterial fouling on the coated silicone rubber surface. In addition, the coated polymer layer is stable under a simulated blood flow, and its antibacterial and antifouling activities remain unchanged even after being in contact with bacterial solution over a two week period. Moreover, the coated polymer layer is hemocompatible, and is able to prevent protein adsorption. This brush-like polymer coating on silicone rubber has great potential for use in intravascular catheters to prevent bacterial infections.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A polycarbonate, comprising:
   a catechol repeat unit comprising i) an aliphatic carbonate backbone portion and ii) a side chain linked to the backbone portion, the side chain comprising a catechol group of formula (A-1):

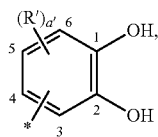
(A-1)

wherein
the side chain of the catechol repeat unit further comprises a secondary amine group,
a' is an integer of 0 to 3, and
each R' is an independent monovalent radical selected from the group consisting of halogens, methyl, and ethyl.

2. The polycarbonate of claim 1, wherein a' is 0.

3. The polycarbonate of claim 1, wherein the catechol repeat unit has a structure in accordance with formula (A-2):

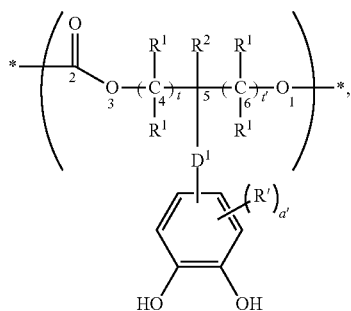
(A-2)

wherein
$D^1$ is a divalent linking group comprising at least 1 carbon and the secondary amine group,
each $R^1$ is an independent monovalent radical selected from the group consisting of hydrogen, halogens, methyl, and ethyl,
$R^2$ is a monovalent radical selected from the group consisting of hydrogen, halogens, and alkyl groups comprising 1 to 6 carbons,
each R' is an independent monovalent radical selected from the group consisting of halogens, methyl, and ethyl,
a' is an integer of 0 to 3,
t is a positive integer having a value of 0 to 2,
t' is a positive integer having a value of 0 to 2, and
t and t' cannot both be zero.

4. A polycarbonate comprising a catechol repeat unit, the catechol repeat unit comprising i) an aliphatic carbonate backbone portion and ii) a side chain linked to the backbone portion, the side chain comprising a catechol group, the catechol repeat unit having a structure in accordance with formula (A-4):

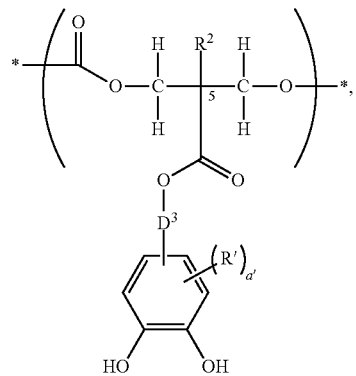
(A-4)

wherein
$D^3$ is a divalent linking group comprising at least 1 carbon,
each R' is an independent monovalent radical selected from the group consisting of halogens, methyl, and ethyl,
a' is an integer of 0 to 3, and
$R^2$ is a monovalent radical selected from the group consisting of hydrogen, halogens, and alkyl groups comprising 1 to 6 carbons.

5. The polycarbonate of claim 1, wherein the catechol repeat unit has a structure in accordance with formula (A-5):

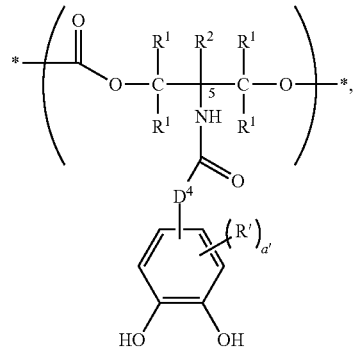
(A-5)

wherein
$D^4$ is a divalent linking group comprising at least 1 carbon and the secondary amine group,
each R' is an independent monovalent radical selected from the group consisting of halogens, methyl, and ethyl,
each $R^1$ is an independent monovalent radical selected from the group consisting of hydrogen, halogens, methyl, and ethyl,
a' is an integer of 0 to 3, and
$R^2$ is a monovalent radical selected from the group consisting of hydrogen, halogens, and alkyl groups comprising 1 to 6 carbons.

6. The polycarbonate of claim 1, wherein the catechol repeat unit has a structure in accordance with formula (A-6):

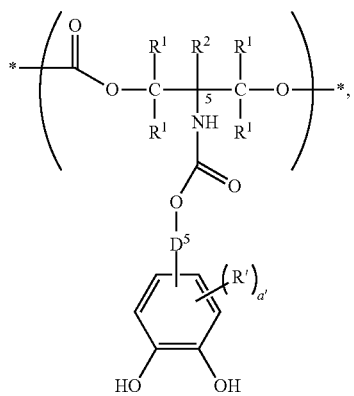

(A-6)

wherein
- $D^5$ is a divalent linking group comprising at least 1 carbon and the secondary amine group,
- each R' is an independent monovalent radical selected from the group consisting of halogens, methyl, and ethyl,
- each $R^1$ is an independent monovalent radical selected from the group consisting of hydrogen, halogens, methyl, and ethyl,
- a' is an integer of 0 to 3, and
- $R^2$ is a monovalent radical selected from the group consisting of hydrogen, halogens, and alkyl groups comprising 1 to 6 carbons.

7. The polycarbonate of claim 1, wherein the catechol repeat unit has a structure in accordance with formula (A-7):

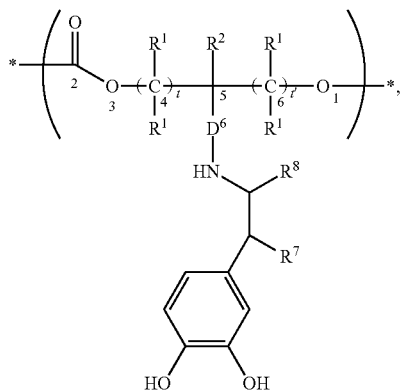

(A-7)

wherein
- $D^6$ is a divalent linking group comprising at least 1 carbon,
- each $R^1$ is an independent monovalent radical selected from the group consisting of hydrogen, halogens, methyl, and ethyl,
- $R^2$ is a monovalent radical selected from the group consisting of hydrogen, halogens, and alkyl groups comprising 1 to 6 carbons,
- $R^7$ is a monovalent radical selected from the group consisting of hydrogen and hydroxyl (OH),
- $R^8$ is a monovalent radical selected from the group consisting of hydrogen and carboxyl (COOH),
- t is a positive integer having a value of 0 to 2,
- t' is a positive integer having a value of 0 to 2, and
- t and t' cannot both be zero.

8. The polycarbonate of claim 1, wherein the catechol repeat unit has a structure in accordance with formula (A-8):

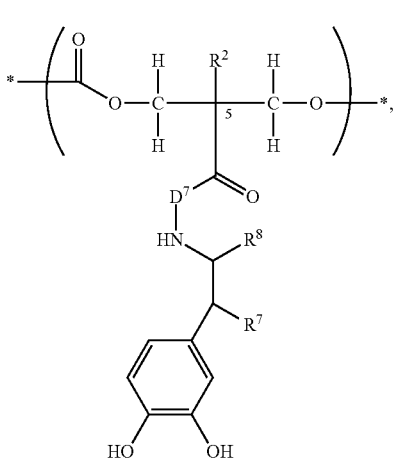

(A-8)

wherein
- $D^7$ is a divalent linking group comprising at least 1 carbon,
- $R^2$ is a monovalent radical selected from the group consisting of hydrogen, halogens, and alkyl groups comprising 1 to 6 carbons,
- $R^7$ is a monovalent radical selected from the group consisting of hydrogen and hydroxyl (OH), and
- $R^8$ is a monovalent radical selected from the group consisting of hydrogen and carboxyl (COOH).

9. The polycarbonate of claim 1, wherein the catechol repeat unit has a structure in accordance with formula (A-9):

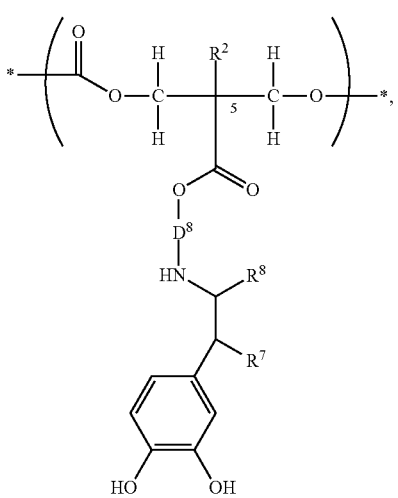

(A-9)

wherein
- $D^8$ is a divalent linking group comprising at least 1 carbon,
- $R^2$ is a monovalent radical selected from the group consisting of hydrogen, halogens, and alkyl groups comprising 1 to 6 carbons,
- $R^7$ is a monovalent radical selected from the group consisting of hydrogen and hydroxyl (OH), and
- $R^8$ is a monovalent radical selected from the group consisting of hydrogen and carboxyl (COOH).

10. The polycarbonate of claim 9, wherein R² is methyl, R⁷ and R⁸ are hydrogen, and D⁸ is

11. The polycarbonate of claim 1, wherein the catechol repeat unit has a structure in accordance with formula (A-10):

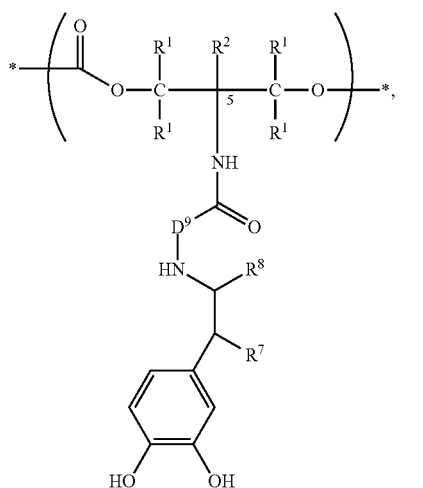

wherein
- D⁹ is a divalent linking group comprising at least 1 carbon,
- each R¹ is an independent monovalent radical selected from the group consisting of hydrogen, halogens, methyl, and ethyl,
- R² is a monovalent radical selected from the group consisting of hydrogen, halogens, and alkyl groups comprising 1 to 6 carbons,
- R⁷ is a monovalent radical selected from the group consisting of hydrogen and hydroxyl (OH), and
- R⁸ is a monovalent radical selected from the group consisting of hydrogen and carboxyl (COOH).

12. The polycarbonate of claim 1, wherein the catechol repeat unit has a structure in accordance with formula (A-11):

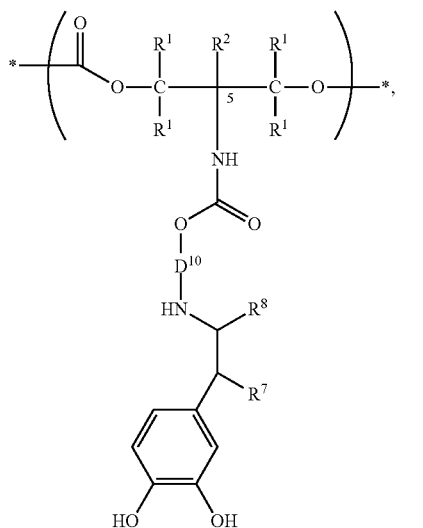

wherein
- D¹⁰ is a divalent linking group comprising at least 1 carbon,
- each R¹ is an independent monovalent radical selected from the group consisting of hydrogen, halogens, methyl, and ethyl,
- R² is a monovalent radical selected from the group consisting of hydrogen, halogens, and alkyl groups comprising 1 to 6 carbons,
- R⁷ is a monovalent radical selected from the group consisting of hydrogen and hydroxyl (OH), and
- R⁸ is a monovalent radical selected from the group consisting of hydrogen and carboxyl (COOH).

13. A polycarbonate, comprising:
- a catechol repeat unit comprising i) an aliphatic carbonate backbone portion and ii) a side chain linked to the backbone portion, the side chain comprising a catechol group of formula (A-1):

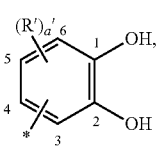

wherein a' is an integer of 0 to 3, and each R' is an independent monovalent radical selected from the group consisting of halogens, methyl, and ethyl;

- a cationic repeat unit comprising i) an aliphatic carbonate backbone portion and ii) a side chain linked to the carbonate backbone, the side chain comprising a cationic group selected from the group consisting of quaternary amine groups, quaternary phosphine groups, and combinations thereof; and
- a PEG repeat unit comprising i) an aliphatic carbonate backbone portion and ii) a side chain linked to the carbonate backbone portion, the side chain comprising a poly(ethylene oxide) chain (PEG chain) having a degree of polymerization of about 5 to about 30;

wherein
the catechol repeat unit, the cationic repeat unit, and the PEG repeat unit are bound in a polycarbonate chain, and
the side chain of the catechol repeat unit further comprises a secondary amine group.

14. The polycarbonate of claim 13, wherein a' is 0.

15. The polycarbonate of claim 13, wherein the cationic repeat unit has a structure in accordance with formula (B-1):

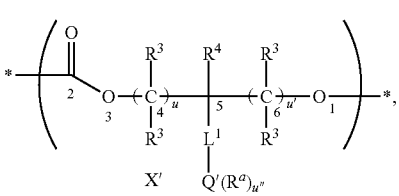

wherein
$L^1$-$Q'(R^a)_{u''}$ is a $C_6$-$C_{25}$ cationic side chain comprising a quaternary ammonium group and/or quaternary phosphonium group, wherein $L^1$ is a divalent linking group comprising at least 3 carbons, Q' is a tetravalent positive-charged nitrogen or phosphorus, u" has a value of 1 to 3, each $R^a$ is an independent radical having a valency of 1 to 3, and each $R^a$ comprises at least 1 carbon, each $R^3$ is an independent monovalent radical selected from the group consisting of hydrogen, halogens, methyl, and ethyl, $R^4$ is a monovalent radical selected from the group consisting of hydrogen, halogens, and alkyl groups comprising 1 to 6 carbons, u is a positive integer having a value of 0 to 2, u' is a positive integer having a value of 0 to 2, u and u' cannot both be zero, and X' is a negative-charged ion.

16. The polycarbonate of claim 13, wherein the cationic repeat unit has a structure in accordance with formula (B-3):

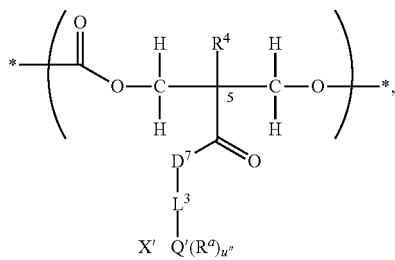

(B-3)

wherein $L^3$-$Q'(R^a)_{u''}$ is a $C_5$-$C_{24}$ cationic moiety comprising a quaternary ammonium group and/or quaternary phosphonium group, wherein $L^3$ is a divalent linking group comprising at least 2 carbons, Q' is a tetravalent positive-charged nitrogen or phosphorus, u" has a value of 1 to 3, each $R^a$ is an independent radical having a valency of 1 to 3, and each $R^a$ comprises at least 1 carbon, $R^4$ is a monovalent radical selected from the group consisting of hydrogen, halogens, and alkyl groups comprising 1 to 6 carbons, and X' is a negative-charged ion.

17. The polycarbonate of claim 13, wherein the cationic repeat unit has a structure in accordance with formula (B-4):

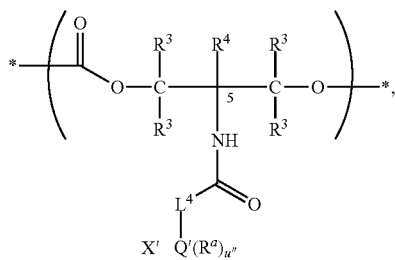

(B-4)

wherein $L^4$-$Q'(R^a)_{u''}$ is a $C_5$-$C_{24}$ cationic moiety comprising a quaternary ammonium group and/or quaternary phosphonium group, wherein $L^4$ is a divalent linking group comprising at least 2 carbons, Q' is a tetravalent positive-charged nitrogen or phosphorus, u" has a value of 1 to 3, and each $R^a$ is an independent radical having a valency of 1 to 3, wherein each $R^a$ comprises at least 1 carbon, each $R^3$ is an independent monovalent radical selected from the group consisting of hydrogen, halogens, methyl, and ethyl, $R^4$ is a monovalent radical selected from the group consisting of hydrogen, halogens, and alkyl groups comprising 1 to 6 carbons, and X' is a negative-charged ion.

18. The polycarbonate of claim 13, wherein the PEG repeat unit has a structure in accordance with formula (C-1):

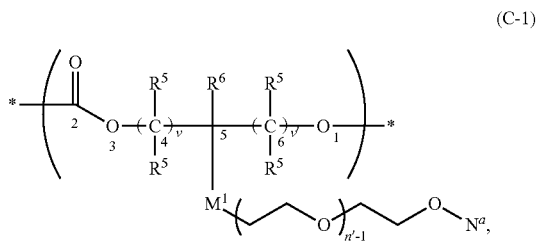

(C-1)

wherein n' is an integer of about 5 to about 30, $M^1$ is a divalent linking group comprising at least 1 carbon, $N^a$ is a monovalent end group selected from the group consisting of hydrogen and radicals comprising at least 1 carbon, each $R^5$ is an independent monovalent radical selected from the group consisting of hydrogen, halogens, methyl, and ethyl, $R^6$ is a monovalent radical selected from the group consisting of hydrogen, halogens, and alkyl groups comprising 1 to 6 carbons, v is a positive integer having a value of 0 to 2, v' is a positive integer having a value of 0 to 2, and v and v' cannot both be zero.

19. The polycarbonate of claim 13, wherein the PEG repeat unit has a structure in accordance with formula (C-2):

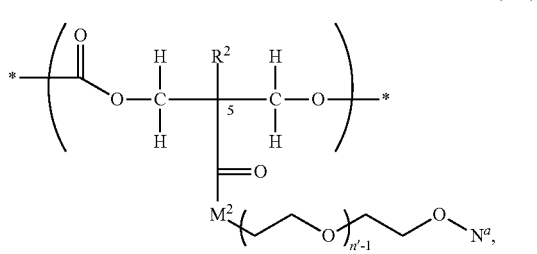

(C-2)

wherein n' is an integer of about 5 to about 30, $M^2$ is a divalent linking group, $N^a$ is a monovalent radical selected from the group consisting of hydrogen and groups comprising at least 1 carbon, and $R^6$ is a monovalent radical selected from the group consisting of hydrogen, halogens, and alkyl groups comprising 1 to 6 carbons.

20. A method of forming the polycarbonate of claim 4, which is a catechol polymer, comprising:

forming by an organocatalyzed ring opening polymerization of one or more cyclic carbonate monomers a first polycarbonate comprising an electrophilic repeat unit, wherein the electrophilic repeat unit comprises i) a carbonate backbone portion and ii) a side chain linked to the carbonate backbone portion, the side chain comprising a leaving group capable of displacement by a nucleophilic group; and treating a mixture of the first polycarbonate in a solvent with a catechol compound comprising the nucleophilic group, thereby forming the catechol polymer.

21. The method of claim 20, wherein the solvent comprises dimethylsulfoxide, acetonitrile, and an alcohol.

22. The method of claim 20, wherein the first polycarbonate and the catechol polymer have substantially the same degree of polymerization.

23. The method of claim 20, wherein the electrophilic repeat unit has a structure in accordance with formula (E-2):

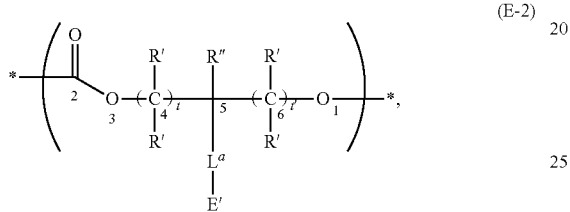

wherein
backbone atoms are shown numbered 1 to 6,
$L^a$ is a divalent linking group comprising at least 1 carbon,
E' is an electrophilic group capable of reacting with a nucleophile to form a moiety comprising a member of the group consisting of quaternary amine groups, quaternary phosphonium groups, and catechol groups,
each R' is an independent monovalent radical selected from the group consisting of hydrogen, halogens, methyl, and ethyl,
R" is a monovalent radical selected from the group consisting of hydrogen, halogens, and alkyl groups comprising 1 to 6 carbons,
t is a positive integer having a value of 0 to 2,
t' is a positive integer having a value of 0 to 2, and
t and t' cannot both be zero.

24. The method of claim 20, wherein the catechol compound is a catecholamine selected from the group consisting of dopamine, epinephrine, norepinephrine, and/or L-dihydroxyphenylalanine (L-DOPA), derivatives of any of the foregoing, and combinations thereof.

25. The method of claim 23, wherein t is 1 and t' is 1.

26. A method, comprising:
forming by an organocatalyzed ring opening polymerization of one or more cyclic carbonate monomers a first polycarbonate comprising an electrophilic repeat unit, wherein the electrophilic repeat unit comprises i) a carbonate backbone portion and ii) a side chain portion linked to the carbonate backbone portion, the side chain comprising a leaving group capable of displacement by a nucleophilic group; and treating the first polycarbonate with a mixture comprising i) a solvent, ii) a first compound comprising a first nucleophilic group and a catechol group, and iii) a second compound comprising a second nucleophilic group, the second nucleophilic group capable of forming a quaternary amine group and/or a quaternary phosphine group, thereby forming an antimicrobial cationic polycarbonate;

wherein
the antimicrobial cationic polycarbonate comprises
i) a first carbonate repeat unit, which is a catechol repeat unit, comprising a first carbonate backbone portion and a first side chain portion linked to the first carbonate backbone portion, the first side chain portion comprising a catechol group of formula (A-1):

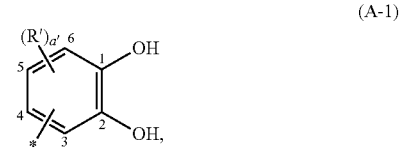

wherein
the first side chain portion of the catechol repeat unit further comprises a secondary amine group,
a' is an integer of 0 to 3, and
each R' is an independent monovalent radical selected from the group consisting of halogens, methyl, and ethyl, and
ii) a second carbonate repeat unit (cationic repeat unit) comprising a second carbonate backbone portion and a second side chain portion linked to the second carbonate backbone portion, the second side chain portion comprising the quaternary amine group and/or the quaternary phosphine group, and
the catechol repeat unit and the cationic repeat unit are derived from the electrophilic repeat unit.

27. A method, comprising:
disposing on a surface of a substrate a mixture comprising a solvent and a catechol polymer, thereby forming an initial film layer, wherein the catechol polymer comprises
i) a first carbonate repeat unit, which is a catechol repeat unit, comprising a first carbonate backbone portion and a first side chain catechol group of formula (A-1):

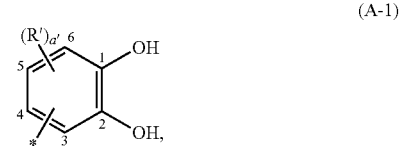

wherein
the first side chain portion of the catechol repeat unit further comprises a secondary amine group,
a' is an integer of 0 to 3, and
each R' is an independent monovalent radical selected from the group consisting of halogens, methyl, and ethyl,
ii) a second carbonate repeat unit, which is a cationic repeat unit, comprising an aliphatic carbonate backbone portion and a side chain cationic group selected from the group consisting quaternary amines, quaternary phosphines, and combinations thereof, and
iii) a third carbonate repeat unit, which is a PEG repeat unit, comprising an aliphatic carbonate backbone portion and a side chain poly(ethylene oxide) group; and
removing the solvent from the initial film layer, thereby forming a treated substrate comprising a catechol layer, the catechol layer comprising the catechol polymer disposed on the surface of the substrate;
wherein the catechol layer is antimicrobial and/or antifouling with respect to at least one Gram-negative and/or Gram-Positive microbe.

28. The method of claim 27, wherein the substrate comprises silicone rubber.

29. The method of claim 27, wherein the substrate is a medical device.

30. The method of claim 29, wherein the medical device is a catheter.

31. The method of claim 27, wherein the catechol polymer is a random copolymer having a structure in accordance with formula (D-3):

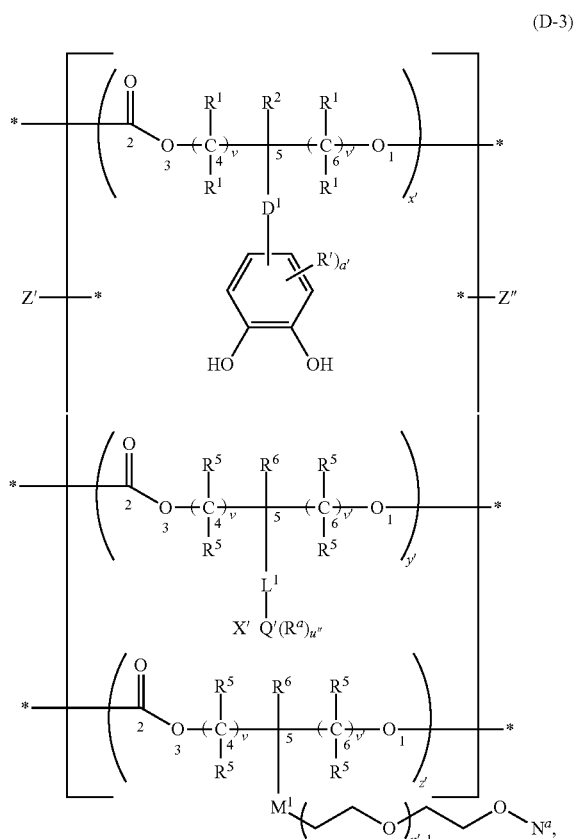

(D-3)

wherein
A) Z' is a monovalent first end group, wherein Z' comprises at least 1 carbon and a heteroatom selected from the group consisting of N, O, and S, wherein the heteroatom is linked to a backbone carbonyl group of the catechol polymer,
B) Z" is a monovalent second end group selected from the group consisting of hydrogen and moieties comprising at least 1 carbon,
C) with respect to catechol repeat units comprising linking group $D^1$:
x' is a positive number having a value of 1 or more,
each $D^1$ is an independent divalent linking group comprising at least 1 carbon,
each $R^1$ is an independent monovalent radical selected from the group consisting of hydrogen, halogens, methyl, and ethyl, each $R^2$ is an independent monovalent radical selected from the group consisting of hydrogen, halogens, and alkyl groups comprising 1 to 6 carbons,
each R' is an independent monovalent radical selected from the group consisting of halogens, methyl, and ethyl,
a' is an integer of 0 to 3,
each t is an independent positive integer having a value of 0 to 2,
each t' is an independent positive integer having a value of 0 to 2, and
t and t' cannot both be zero in any catechol repeat unit,
D) with respect to cationic repeat units comprising linking group $L^1$:
y' is a number having a value greater than or equal to 1,
each $L^1Q'(R^a)_{u''}$ is an independent $C_6$-$C_{25}$ cationic side chain comprising a quaternary ammonium group and/or quaternary phosphonium group, wherein $L^1$ is an independent divalent linking group comprising at least 3 carbons, Q' is a tetravalent positive-charged nitrogen or phosphorus, u" has a value of 1 to 3, each Ra is an independent radical having a valency of 1 to 3, and each $R^a$ comprises at least 1 carbon,
each $R^3$ is an independent monovalent radical selected from the group consisting of hydrogen, halogens, methyl, and ethyl,
each $R^4$ is an independent monovalent radical selected from the group consisting of hydrogen, halogens, and alkyl groups comprising 1 to 6 carbons,
each u is an independent positive integer having a value of 0 to 2,
each u' is an independent positive integer having a value of 0 to 2,
u and u' cannot both be zero in any cationic repeat unit, and
each X' is an independent negative-charged ion, and
E) with respect to PEG repeat units comprising linking group $M^1$:
z' is a number having a value greater than or equal to 1,
n' is a positive integer of about 5 to about 30,
each $M^1$ is an independent divalent linking group comprising at least 1 carbon,
each $N^a$ is an independent monovalent radical selected from the group consisting of hydrogen and groups comprising at least 1 carbon,
each $R^5$ is an independent monovalent radical selected from the group consisting of hydrogen, halogens, methyl, and ethyl,
each $R^6$ is an independent monovalent radical selected from the group consisting of hydrogen, halogens, and alkyl groups comprising 1 to 6 carbons,
each v is an independent positive integer having a value of 0 to 2,
each v' is an independent positive integer having a value of 0 to 2, and
v and v' cannot both be zero in any PEG repeat unit.

32. The method of claim 27, wherein the catechol polymer is a random copolymer having a structure in accordance with formula (D-4):

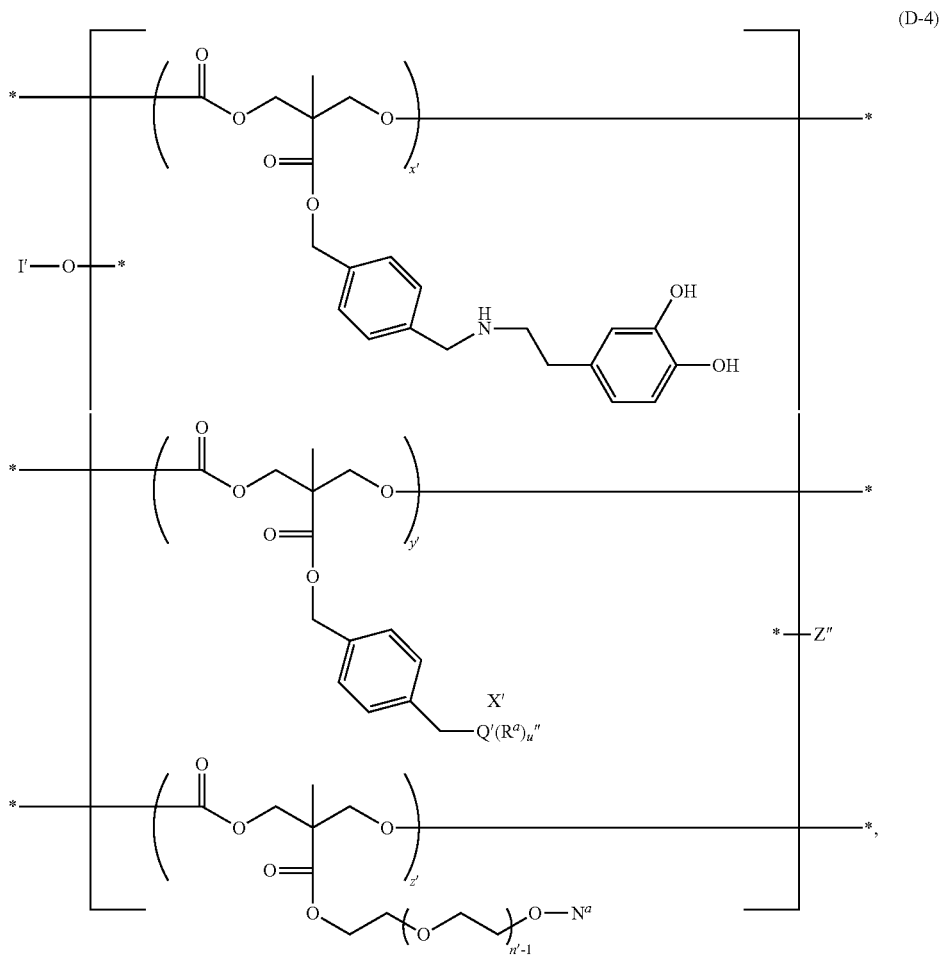

(D-4)

wherein
I'-O is a monovalent first end group, wherein I' comprises at least 1 carbon,
each Q' is an independent tetravalent positive-charged nitrogen or phosphorus,
each u" is an independent positive integer having a value of 1 to 3,
each $R^a$ is an independent radical having a valency of 1 to 3, wherein each $R^a$ comprises at least 1 carbon,
Z" is a monovalent second end group selected from the group consisting of hydrogen and moieties comprising at least 1 carbon,
each $N^a$ is an independent monovalent radical selected from the group consisting of hydrogen and groups comprising at least 1 carbon,
R is a monovalent radical having at least 1 carbon,
x' is a positive number having a value of 1 or more,
y' is a positive number having a value of 1 or more,
z' is a positive number having a value of 1 or more,
n' is a positive number of about 5 to about 30, and
$X^-$ is a negative charged ion.

33. An antimicrobial and/or antifouling silicone rubber, comprising:
a catechol layer disposed on a surface of a silicone rubber substrate, the catechol layer comprising the polycarbonate of claim 13.

34. The silicone rubber of claim 33, wherein the substrate is a silicone rubber tubing, and the catechol layer is disposed on an inner surface and an outer surface of the tubing.

* * * * *